United States Patent
Namir

(10) Patent No.: US 9,779,205 B2
(45) Date of Patent: Oct. 3, 2017

(54) SYSTEMS AND METHODS FOR RATIONAL SELECTION OF CONTEXT SEQUENCES AND SEQUENCE TEMPLATES

(71) Applicant: Yoav Namir, Tel Aviv (IL)

(72) Inventor: Yoav Namir, Tel Aviv (IL)

( * ) Notice: Subject to any disclaimer, the term of this patent is extended or adjusted under 35 U.S.C. 154(b) by 1172 days.

(21) Appl. No.: 13/764,894

(22) Filed: Feb. 12, 2013

(65) Prior Publication Data

US 2013/0230916 A1 Sep. 5, 2013

Related U.S. Application Data

(63) Continuation of application No. 12/733,256, filed as application No. PCT/IL2008/001140 on Aug. 20, 2008, now abandoned.

(60) Provisional application No. 60/935,592, filed on Aug. 21, 2007.

(51) Int. Cl.
| | |
|---|---|
| *G06F 19/22* | (2011.01) |
| *G06F 17/30* | (2006.01) |
| *G06F 19/24* | (2011.01) |
| *G06F 19/28* | (2011.01) |
| *G06F 19/18* | (2011.01) |

(52) U.S. Cl.
CPC ........ *G06F 19/22* (2013.01); *G06F 17/30286* (2013.01); *G06F 17/30327* (2013.01); *G06F 17/30598* (2013.01); *G06F 19/24* (2013.01); *G06F 19/28* (2013.01); *G06F 19/18* (2013.01)

(58) Field of Classification Search
None
See application file for complete search history.

(56) References Cited

U.S. PATENT DOCUMENTS

| | | | |
|---|---|---|---|
| 7,253,342 B2 | 8/2007 | Zhang et al. | |
| 2004/0142325 A1* | 7/2004 | Mintz | G06F 19/24 435/6.12 |

OTHER PUBLICATIONS

Bailey, T. L. & Elkan, C. The value of prior knowledge in discovering motifs with MEME. International Conference on Intelligent Systems for Molecular Biology 3, 21-29 (1995).*
Beißbarth, T. & Speed, T. P. GOstat: find statistically overrepresented Gene Ontologies within a group of genes. Bioinformatics 20, 1464-1465 (2004).*
FitzGerald, P. C., Shlyakhtenko, A., Mir, A. A. & Vinson, C. Clustering of DNA Sequences in Human Promoters. Genome Research 14, 1562-1574 (2004).*
Hughes, J. D., Esterp, P. W., Tavazoie, S. & Church, G. M. Computational identification of Cis-regulatory elements associated with groups of functionally related genes in *Saccharomyces cerevisiae*. Journal of Molecular Biology 296, 1205-1214 (2000).*
Joshi, C. P., Zhou, H., Huang, X. & Chiang, V. L. Context sequences of translation initiation codon in plants. Plant Molecular Biology 35, 993-1001 (1997).*

(Continued)

*Primary Examiner* — Soren Harward
(74) *Attorney, Agent, or Firm* — Browdy and Neimark, PLLC

(57) ABSTRACT

Provided are systems and methods for rational selection of context sequences and sequence templates including a computer implemented method for obtaining a repository of attributes sets where the attributes sets are statistically associated with a sequence template representing two or more context sequences.

10 Claims, 10 Drawing Sheets

(56) References Cited

OTHER PUBLICATIONS

Kozak, M. Compilation and analysis of sequences upstream from the translational start site in eukaryotic mRNAs. Nucleic Acids Research 12, 857-872 (1984).*

Molina, C. & Grotewold, E. Genome wide analysis of Arabidopsis core promoters. BMC Genomics 12, 1-12 (2005).*

Nakagawa, S., Niimura, Y., Gojobori, T., Tanaka, H. & Miura, K. ichiro. Diversity of preferred nucleotide sequences around the translation initiation codon in eukaryote genomes. Nucleic Acids Research 36, 861-871 (2008).*

Quandt, K., Frech, K., Karas, H., Wingender, E. & Werner, T. MatInd and MatInspector: new fast and versatile tools for detection of consensus matches in nucleotide sequence data. Nucleic Acids Research 23, 4878-4884 (1995).*

Roth, F. P., Hughes, J. D., Estep, P. W. & Church, G. M. Finding DNA regulatory motifs within unaligned noncoding sequences clustered by whole-genome mRNA quantitation. Nature Biotechnology 16, 939-945 (1998).*

Day, W. H. E. & Edelsbrunner, H. Efficient algorithms for agglomerative hierarchical clustering methods. Journal of Classification 1, 7-24 (1984).*

Fadel, R., Jakobsen, K. V., Katajainen, J. & Teuhola, J. Heaps and heapsort on secondary storage. Theoretical Computer Science 220, 345-362 (1999).*

Vitter, J. S. Efficient memory access in large-scale computation. In STACS 91 480, 26-41 (Springer-Verlag, 1991).*

Brengel, K., Crauser, A., Ferragina, P. & Meyer, U. An experimental study of priority queues in external memory. Journal of Experimental Algorithmics 5, 17:1-24 (2000).*

Brodal, G. S. & Katajainen, J. Worst-case efficient external-memory priority queues. In Algorithm Theory—SWAT'98 (eds. Arnborg, S. & Ivansson, L.) 107-118 (Springer Berlin Heidelberg, 1998).*

Corral, A., Manolopoulos, Y., Theodoridis, Y. & Vassilakopoulos, M. Closest pair queries in spatial databases. ACM SIGMOD Record 29, 189-200 (2000).*

Naor, D., Martel, C. U. & Matloff, N. S. Performance of Priority Queue Structures in a Virtual Memory Environment. The Computer Journal 34, 428-437 (1991).*

Pagh, R. Basic External Memory Data Structures. Chapter 2 of Algorithms for Memory Hierarchies (eds. Meyer, U., Sanders, P. & Sibeyn, J.) 14-35 (Springer Berlin Heidelberg, 2003).*

D. Arthur, S. Vassilvitskii., "How Slow is the k-Means Method?" (Stanford , yet unpublished) (2006).

Dennis et al., "David: Database for Annotation, Visualization, and Integrated Discovery" Genome Biology 4(5): R60-60.11 (2003).

Heidecker et al., "Structural analysis of plant genes" Annu. Rev. Plant Physiol. 37:439-466 (1986).

Hosack et al., "Identifying Biological Themes within Lists of Genes with EASE" Genome Biology 2003 4(6) (2003).

M. Jaiswal et al., "Context Sequence for Transcription Factors Surrounding Start Codon in Model Crops" Current Science, 93(2) Jul. 25, 2007.

Joshi et al., "An inspection of the domain between putative TATA box and translation start site in 79 plant genes" Nucleic Acids Research, 15(16) 6643-6653 (1987).

Joshi et al., "Context sequences of translation initiation codon in plants" Plant Molecular Biology 35: 993-1001 (1997).

Kozak M. "Nucleotide sequences of 5'-terminal ribosome-protected initiation regions from two reovirus messages" Nature 269:390-394 (1978).

Kozak M. "Possible role of flanking nucleotides in recognition of the AUG initiator condon by eukaryotic ribosomes" Nucleic Acids Res. Oct. 24, 1981;9(20):5233-52.

Kozak M. "Sequences of ribosome binding sites from the large size class of reovirus mRNA" J Virol. May;42(2):467-73 (1982).

Kozak M. "Compilation and analysis of sequences upstream from the translational start site in eukaryotic mRNAs" Nucleic Acids Res. Jan. 25;12(2):857-72 (1984).

Kozak M "An analysis of 5'-noncoding sequences from 699 vertebrate messenger RNAs" Nucl Acids Res 15:8125-8148 (1987).

Kozak M "At least six nucleotides preceding the AUG initiator codon enhance translation in mammalian cells" J Mol Biol 196: 947-950 (1987).

Q. Liu et al., "Comparative studies on sequence characteristics around translation initiation codon in four eukaryotes" Journal of Genetics, 84(3) Dec. 2005.

Samir V. S., et al., "Conserved nucleotide sequences in highly expressed genes in plants"Journal of Genetics, 78(2) 123-131 (1999).

Sleat D.E.,et al., "Characterization of the 5-leader Sequence of Tobacco Mosaic Virus RNA as a General Enhancer of Translation in vitro" Gene 217:217-225 (1987).

Taylor JL, et al., "Optimizing the Expression of Chimeric Genes in Plant Cells" Mol. Gen. Genet. 210:572-577 (1987).

W. Zhong et al., "Improved K-Means Clustering Algorithm for Exploring Local Protein Sequence Motifs, Representing Common Structural Property" IEEE Transactions on Nanobioscience 4(3) Sep. 2005.

Karen F. Han et al., "Recurring Local Sequence Motifs in Proteins", J. Mol. Biol. (1995) 251, pp. 176-187.

Thomas H. Cormen et al., "Introduction to Algorithms", Second Edition (2002), pp. 1-1203.

Rubab Zahra Naqvi et al., "Role of Plant Promoters and Their Cis Regulatory Elements in Gene Expression Regulation", European Journal of Pharmaceutical and Medical Research (2016), 3(1), pp. 347-352.

L. Rangan et al., "Analysis of Context Sequence Surrounding Translation Initiation Site from Complete Genome of Model Plants", Mol Biotechnol, (2008). pp. 207-213.

* cited by examiner

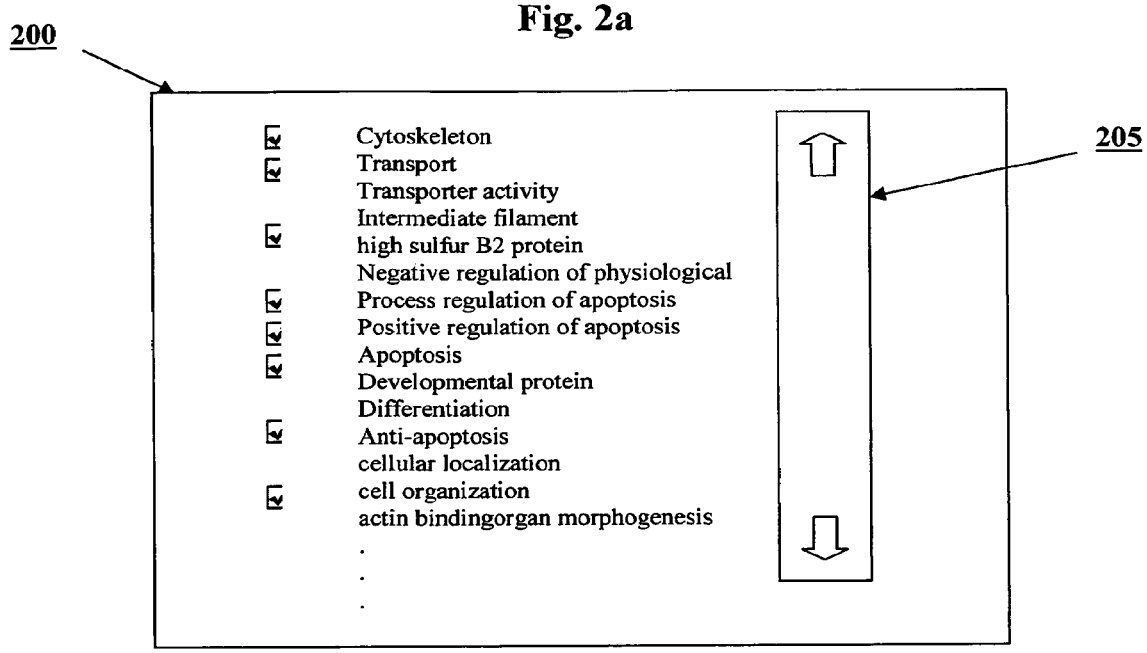

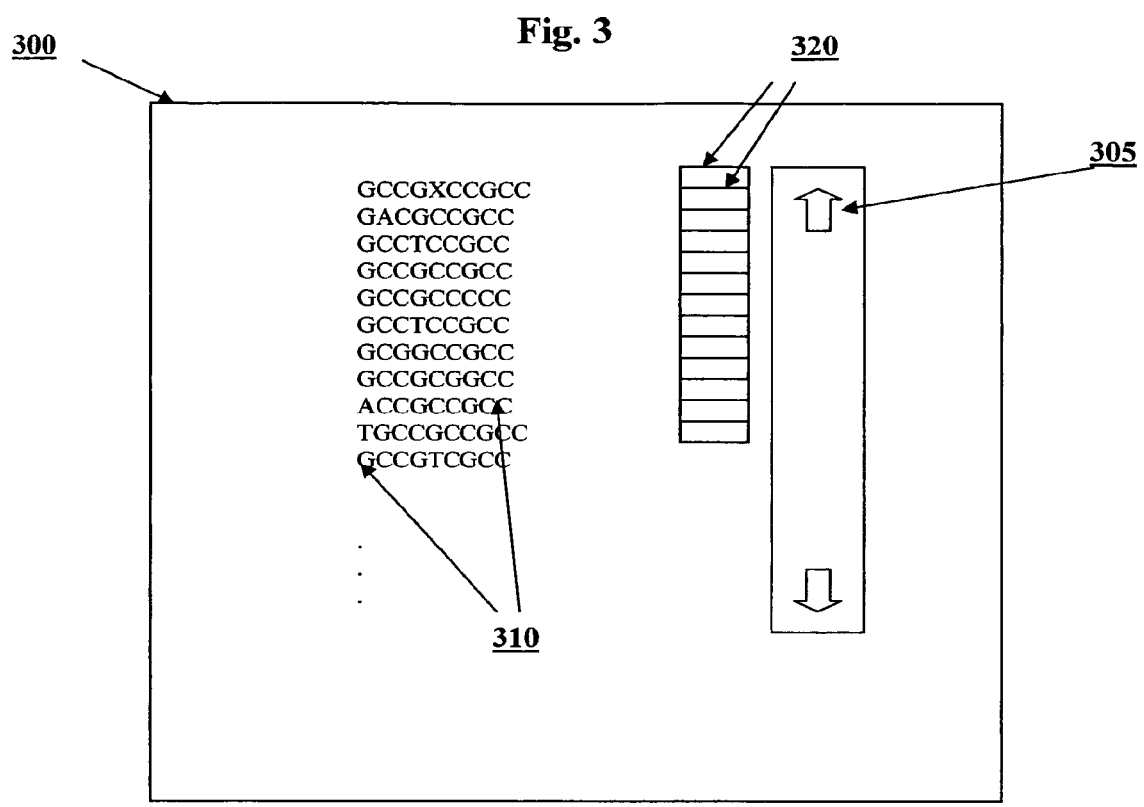

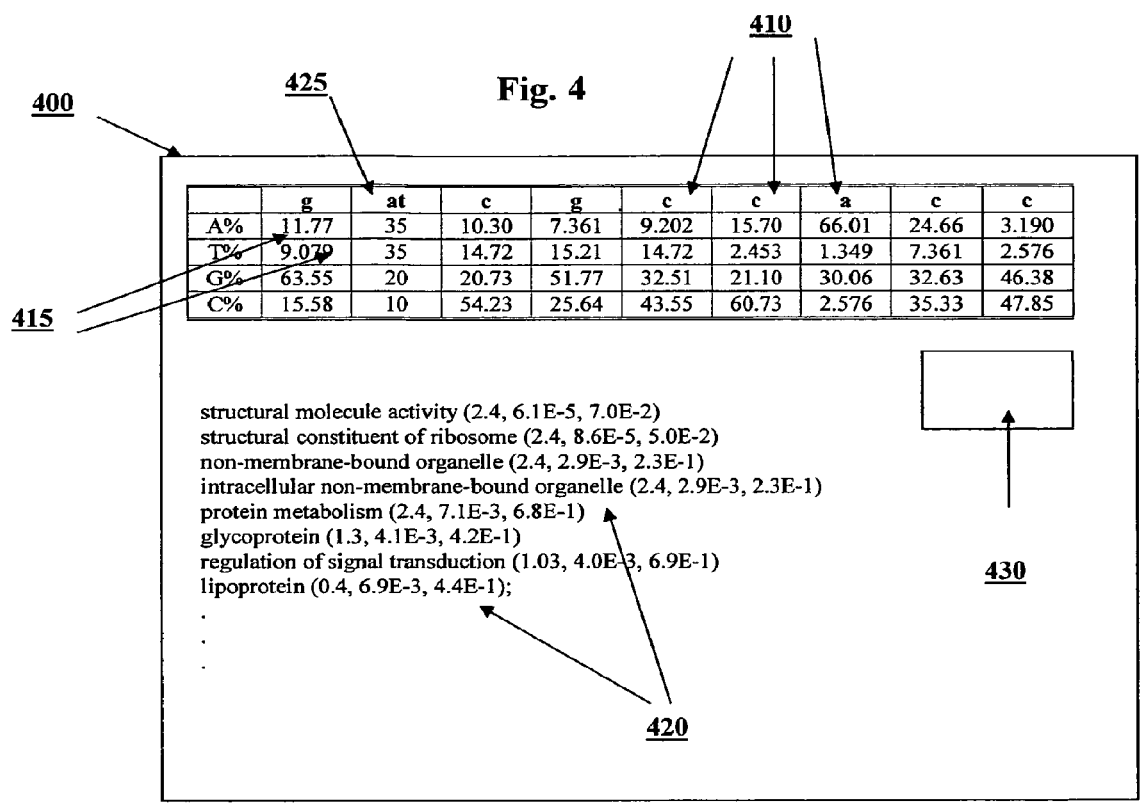

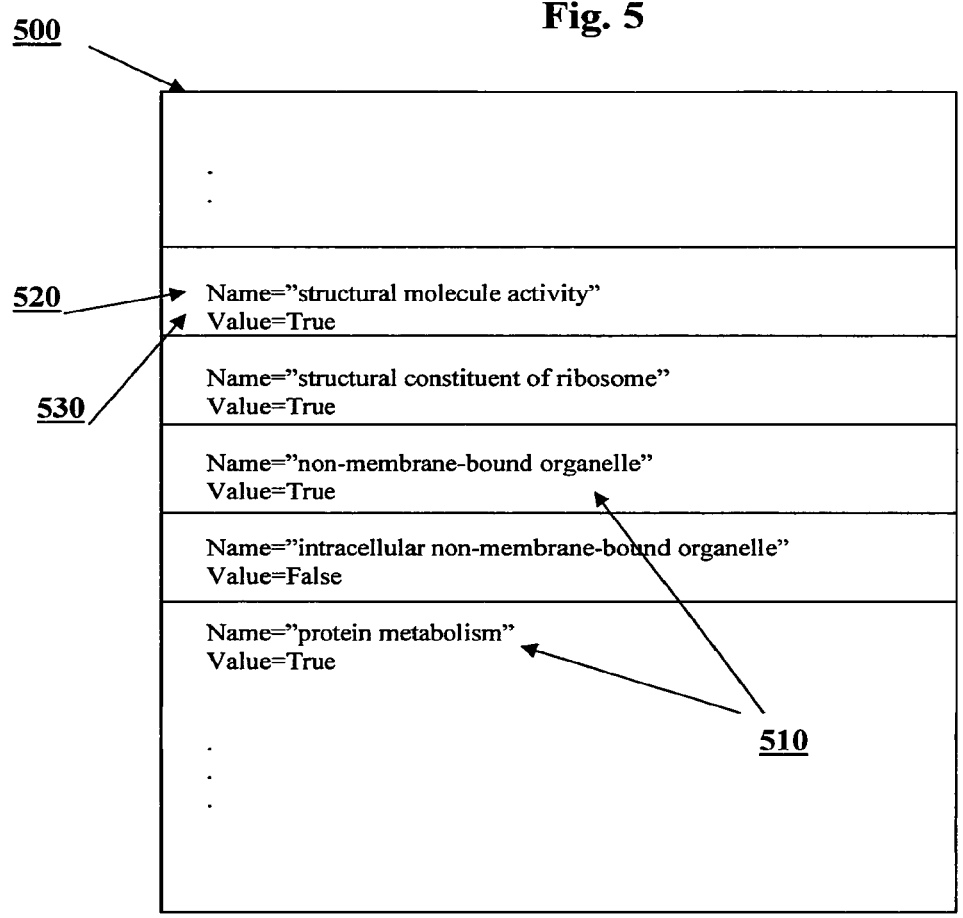

600

700

SYSTEMS AND METHODS FOR RATIONAL SELECTION OF CONTEXT SEQUENCES AND SEQUENCE TEMPLATES

This Application is a Continuation Application of U.S. patent application Ser. No. 12/733,256 filed on Feb. 19, 2010, which is a 371 of International Application No. PCT/IL2008/001140 filed on Aug. 20, 2008, which claims benefit from U.S. Provisional Patent Application No. 60/935,592 under 35 U.S.C. 119(e) filed on Aug. 21, 2007, the entire content of each of which is hereby incorporated by reference in its entirety.

FIELD OF INVENTION

The present invention relates to the analysis of polynucleotide sequence clusters, and in particular for the characterization of such sequence according to one or more parameters.

BACKGROUND OF THE INVENTION

I. Analyzing Polynucleotide Sequences by Clustering

The increasing amounts of polynucleotide sequence data present an analytical challenge. Such large amounts of data on the one hand provide an opportunity for extensive research, but on the other hand are difficult to analyze by conventional analytical methods. However, one method that has been found to be generally effective for analyzing such large amounts of sequence data is clustering.

Clustering may be performed in a variety of methods. Hierarchical clustering, for example, seeks to create by steps of either mergers or divisions, a hierarchy of segments or clusters. Agglomerative approaches build the hierarchy of clusters by steps of such mergers. Some approaches combine the above two[1].

In addition, there are also non-hierarchical methods, which do not seek to create a hierarchy of segments or clusters. The K-Means clustering algorithm is an example of such a clustering technique. It has been used in combination with other techniques, for example, for exploring protein structure[2]. It was also used to identify recurring local sequence motifs for proteins[3].

II. Context Polynucleotide Sequence Analysis

Heidecker and Messing[4] found the NNANNAUGGC (SEQ ID NO:1) motif in the AUG context. Joshi[5] identified the consensus sequence of AAAAACAA[A/C]AAUGGC (SEQ ID NO:2).
More recently, a survey which included 5074 plant genes demonstrated that higher plants have an AC-rich consensus sequence, aaaaacaA(A/C)aAUGGCg (SEQ ID NO:3)as a context of AUG[6]. These finding were recently supported[7].

Analysis of 5' untranslated region of mRNA of vertebrates were initially focused on conserved consensus sequence signals which accommodated translation initiation[8]. Studies which followed, attempted to analyze the consensus sequence about said translation initiation signal[9]. The later study has demonstrated conserved purines at position −3 and at position +4. The following conserved sequences were identified in the same study: (GCC)GCC(A/G)CCAUGG (SEQ ID NO:4).

Consensus sequences are useful in research for locating the translation initiator codon. The untranslated leader sequence may additionally influence gene expression levels[10]. It was previously appreciated that Kozak-Like elements in the context of the initiator codon indeed affect expression levels[11,12,13,14]. Therefore, in U.S. Pat. No. 7,253,342, leader sequence was used to directly influence the expression of the specifically attached gene by either increasing expression, or for maintaining stable mRNA levels[15].

SUMMARY OF THE INVENTION

In one aspect, the present invention is directed to a computer implemented method for obtaining a repository of attributes sets, wherein attributes sets are statistically associated with a sequence template representing two or more context sequences, comprising:

(a) obtaining a dataset of context sequences;

(b) transforming each context sequence to a sequence template, thereby obtaining a dataset of sequence templates;

(c) clustering said dataset of sequence templates into a plurality of clusters according to a distance formula; wherein at least one of said clusters is statistically associated with at least one attributes set;

(d) inserting into said repository each of said clusters and said attributes set which is statistically associated with said each of said clusters;

In one embodiment, the dataset of context sequences of step is further subjected to multiple sequence alignment. The later provides a solution in a particular instance, for example, where the context sequences in the data set are of different lengths or where the context sequences in the data were substantially affected by insertion/deletion regions.

In another aspect, the present invention is directed to repository obtained by the computer implemented method obtaining a repository of attributes sets as defined.

In a second aspect, the present invention is directed to a computer implemented method for identifying a sequence template as statistically associated with an attributes set of interest, comprising:

(a) providing a repository of attributes sets; wherein attributes sets are statistically associated with a sequence template representing two or more context sequences;

(b) selecting an attributes set; and (c) retrieving at least one sequence template statistically associated with said attributes set.

Optionally, the computer implemented for identifying a sequence template as statistically associated with an attributes set of interest, further comprises the step of merging at least two retrieved sequence templates.

In one embodiment, the attributes are selected from: the Gene Ontology Project (GO), Interpro annotation (European Molecular Biology Laboratory, EMBL), SMART (a Simple Modular Architecture Research Tool, found at (smart.embl-heidelberg.de, UniProt Knowledgebase (SwissProt), OMIM (by NCBI) PROSITE (by the Swiss Institute of Bioinformatics), Protein Information Resource (PER), GeneCards, and Kyoto Encyclopedia of Genes and Genomes (KEGG).

In a third aspect, the present invention is directed to a computer memory system comprising a plurality of tree topologies representing plurality of (k) heaps, wherein the plurality of tree topologies is managed through a common interface; and (k≥1).

In a one embodiment, the heaps are min heaps. In another embodiment, the heaps are max heaps.

In yet another embodiment, an active subset of heaps is held in Random Access Memory (RAM), while the rest of said heaps are maintained on a secondary storage.

In yet another aspect, the invention is directed to a computer implemented method for clustering a plurality of polynucleotide sequences, comprising: determining an attributes set for the plurality of polynucleotide sequences; and clustering the polynucleotide sequences into a plurality of clusters according to values of said attributes set.

In another aspect, the invention is further directed to a method of preparing a polynucleotide construct, comprising:

(a) identifying a sequence template as statistically associated with an attributes set of interest according to the method of the present invention;

(b) preparing a polynucleotide construct having at least one portion operably linked to a context sequence; wherein said context sequence is characterized as having either 80%-85%, 85%-90%, or 90%-100% homology with said sequence template.

In another embodiment, the preparing step comprises synthesizing said context sequence. In another embodiment, the preparing step comprises the preparing of an expression vector comprising said context sequence. In another embodiment, the preparing step comprises the preparing of a probe comprising said context sequence.

In another aspect, the present invention is directed to a computerized system configured for identifying a sequence template as statistically associated with an attributes set of interest, the computerized system comprising: context sequence clustering module, configured to cluster said sequences into a plurality of clusters; an enrichment analysis module, configured to provide enrichment appraisal, wherein context sequence clustering module being communicatively coupled to the enrichment analysis module.

Unless otherwise defined, all technical and scientific terms used herein have the same meaning as commonly understood by one of ordinary skill in the art to which this invention belongs. The materials, methods, and examples provided herein are illustrative only and not intended to be limiting.

Although the present invention is described with regard to a "computer" which may optionally be implemented on a "computer network", it should be noted that optionally any device featuring a data processor and/or the ability to execute one or more instructions may be described as a computer, including but not limited to a PC (personal computer), or a server. Any two or more of such devices in communication with each other, and/or any computer in communication with any other computer may optionally comprise a "computer network".

BRIEF DESCRIPTION OF THE DRAWINGS

The present invention is illustrated by way of example, and not by way of limitation, in the figures of the accompanying drawings and in which like reference numerals refer to similar elements and in which:

FIG. 2a illustrates, in accordance with one embodiment of the present invention, an exemplary user interface for obtaining a requested function array from a user.

FIG. 3 illustrates, in accordance with one embodiment of the present invention, an exemplary user interface for proposing the predicted context sequences for synthesis. Among the nucleotide sequences shown are GCCCGNC-CGCC (SEQ ID NO:5) and TGCCGCCGCC (SEQ ID NO:6).

FIG. 4 illustrates, in accordance with one embodiment of the present invention, an exemplary viewer application reproducing a context sequence, the cellular function annotations and the size of the context sequence cluster.

FIG. 5 illustrates, in accordance with one embodiment of the present invention, an exemplary data structure of a function attribute array or the cellular function annotations array.

DETAILED DESCRIPTION OF THE INVENTION

Figure 1:
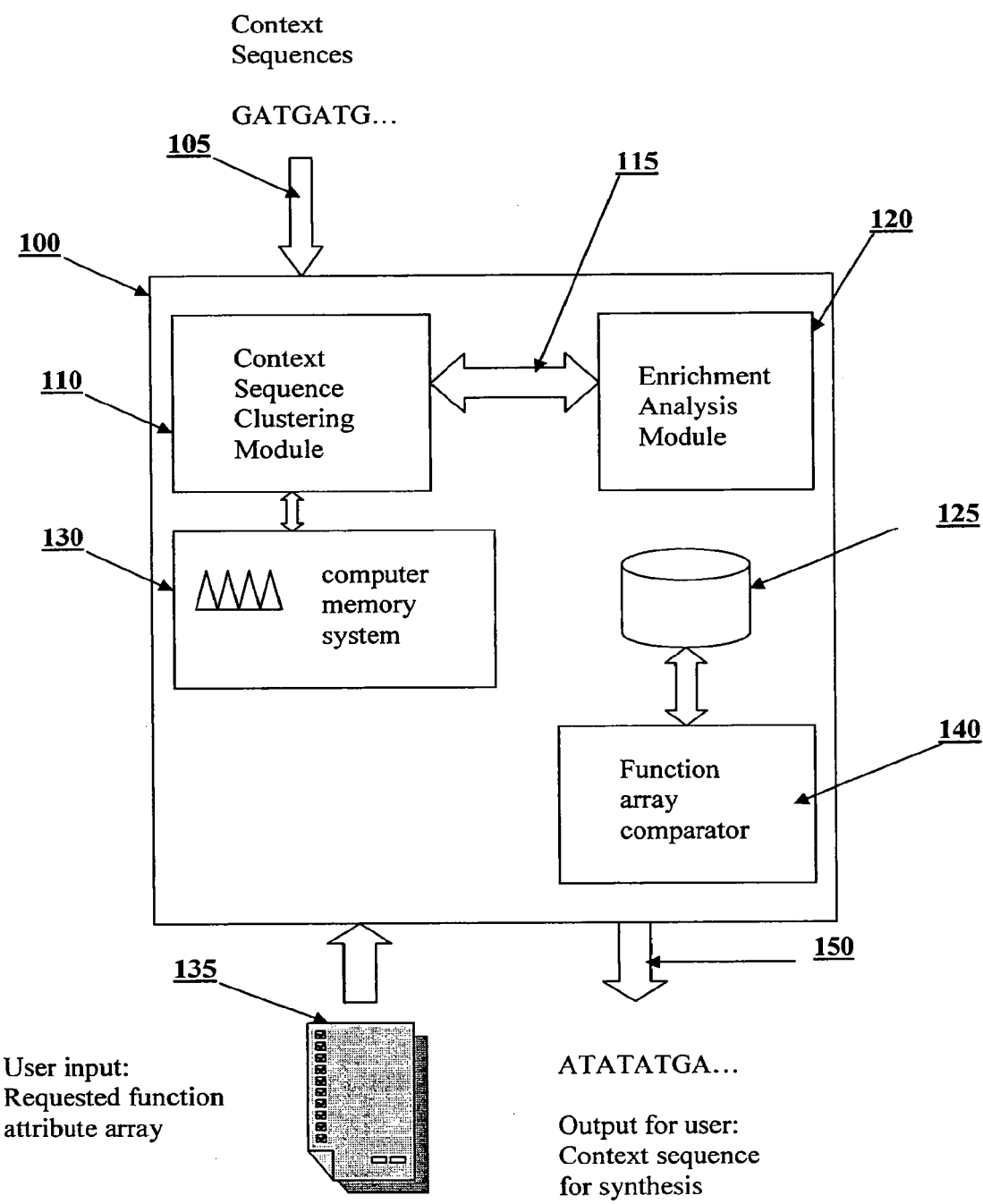
FIG. 1 illustrates, in accordance with one embodiment of the present invention, an exemplary computerized system on which the present invention may be implemented.

The present invention, in some embodiments, is of a system and method for analyzing a plurality of nucleotide or other sequences. In other embodiments, the present invention relates to a system and method which provide more efficient memory structures and computational processes. The later system and method may optionally be used with the former embodiments or may optionally be used independently.

For the sake of clarity only and without any intention of being limiting, the below description is divided into three sections. Section I relates to the system of the present invention; Section II relates to embodiment for obtaining of a repository of attributes sets, statistically associated with context sequences and/or a sequence template representing the them; Section III relates to embodiments which provide more efficient memory structures and computational processes; Section IV details embodiments of a computer implemented method for identifying a sequence template as statistically associated with an attributes set of interest; and Section V relates to experimental examples using such embodiments;

Nomenclature

For the purposes of the present invention, "cellular function annotation", "function attribute", and "attribute" of a given gene shall mean an attribute, term, characterization, molecular function annotation, or biological process annotation describing a gene or a gene product. The terms can be used interchangeably and synonymously herein. The cellular function annotation are typically reported in variety of sources such as, but not limited to, the Gene Ontology Project (GO), Interpro annotation (European Molecular Biology Laboratory, EMBL), SMART (a Simple Modular Architecture Research Tool, found at (smart.embl-heidelberg.de), UniProt Knowledgebase (SwissProt), OMIM (by NCBI) PROSITE (by the Swiss Institute of Bioinformatics), Protein Information Resource (PIR), GeneCards, Kyoto Encyclopedia of Genes and Genomes (KEGG). It should be emphasized that the above terms and attributes are continuously updated, and new versions are made available on a monthly basis and therefore the systems and methods of the present invention should be interpreted as limited by the gene annotation known at time of filing the application for the invention. Furthermore, it should be noted that the user may optionally operate the method or system of the present invention with any such function attributes, as long as they may be characterized according to a numerical grade; such a grade may optionally be Boolean ("1" or "0"), or alternatively may feature a plurality of discrete numbers or continuous numerical values.

By way of an illustrative example, the term or attribute "cell adhesion" associated to *Homo sapiens* discoidin domain receptor tyrosine kinase 1 (DDR1, RefSeq accession: NM_001954) is a cellular function annotation. This attribute is found, for example, in Gene Ontology under GO:0007155.

The term "complete function attributes set", and "complete attributes set" shall mean the complete set of function attributes i.e. all function attributes stored in a repository of the present invention. The terms can be used interchangeably and synonymously herein.

The term "function attributes set", "attributes set" and "function attributes array" shall mean a subset of the complete function attributes set. The terms can be used interchangeably and synonymously herein. Optionally, the function attributes array can be used to represent a specific user selection in which the user manifests particular function attributes of interest. The user can typically select an attributes set in order to perform the computer implemented method of the present invention for identifying a sequence template whish is statistically associated with the attributes set of interest.

Alternatively, by way of non-limiting example, the attributes set can be used to represent attributes set which is statistically associated with a sequence template. The later can be identified in functional appraisal performed by the methods and system of the present invention. The later is typically performed with respect to a cluster of context sequences or attributes associated with a gene operably linked to the context sequences of the cluster. The results of the functional appraisal performed can thus be represented by an attributes set.

The attributes set optionally feature an array of real numbers, with each of said numbers representing a level of association of a particular annotation or attribute. It can also feature an array of binary digits, where each of said binary digit representing association with a particular annotation or attribute. In this case, '0' can represent the absence of association of a particular function attribute and '1' can indicates statistical association of the particular function attribute.

The term "sequence" shall mean a polynucleotide sequence, continuous or otherwise, of nucleotides being selected from a group consisting of deoxyribonucleotides (DNA) and ribonucleotides (RNA), genomic or otherwise, coding or non-coding. Sequence does not encompass therefore gene order in general or genomic meta structures.

The term "context sequence" shall mean a sequence which regulate or affect a gene product (mRNA, polypeptide and alike). Context sequences consist of at least portion of un-translated sequence. By way of non-limiting example, a context sequence may comprise a sequence which is operably linked to a coding region, sequence affecting expression level of a gene product or otherwise a sequence regulating gene product (or activity). Therefore, a context sequence may comprise a stretch of nucleotides preceding the translation initiation codon of mRNA molecule. A context sequence may comprise a stretch of nucleotides downstream to the translation termination codon of mRNA molecule. In the above examples the context sequence was defined by its relative location to a coding region. However, a context sequence of the present invention may further comprise a promoter, enhancer, inhibitor or other regulatory region.

For the purposes of the present invention, "template" or "sequence template" shall include a matrix $T_{4 \times l}$, where (l) denotes the length of the context sequences or aligned context sequence which are represented by the template. The template can either represent the distribution of each nucleotide for each position along a context sequence. The template can further include a matrix (T) where T[a,i] holds the distribution of nucleotide (a) at position (i) in of the context sequences represented. The terms can be used interchangeably and synonymously herein.

As discussed below, at initiation of a clustering method each context sequence is transformed to a template. The skilled person in the art would appreciate that context sequence transformation into a template can typically be performed as an integral part of matrix allocation. By way of a non-limiting example, if a single context sequence has 'A' at position 3 then T['A',3]=1.0 (T['C',3]=0, for obvious reasons).

For example, the sequence 'AG' is represented by a template having the following distribution matrix:

Simplified example of distribution matrix held in a template, at initialization. At this stage, the template represents a single sequence having the prescribed distributions.

|      | Position = 0 | Position = 1 |
|------|--------------|--------------|
| P(A) | 1.0          | 0            |
| P(G) | 0            | 1.0          |
| P(T) | 0            | 0            |
| P(C) | 0            | 0            |

During the prosecution of the methods of the present invention a sequence template can represent a cluster of context sequences and the distribution matrix will thus reflect the distribution of nucleotides which characterizes the context sequences within the cluster. The sequence template can typically further comprise a set of gene names or unique identifiers which are operably linked or affected by the context sequences represented thereby.

The term "repository" and "database" shall mean a database or any system configured for insertion and retrieval of information of the present invention. The terms can be used interchangeably and synonymously herein.

The repository of the present invention is typically configured for insertion and retrieval of attributes, attributes set, and context sequences. The later are typically in a form of sequence of ASCII characters. The repository of the present invention can also be configured for insertion and retrieval of sequence templates which can typically comprise an array of numbers, or a 2D matrix of numbers. Moreover, a repository of the present invention is typically configured to insert and retrieve pointers or association between information elements stored therein. In particular, the repository of the present invention can insert and retrieve an attributes set, a sequence template, and to associate between them; so as to enable retrieval of a sequence template together with at least one respective attributes set. Moreover, it can be configured to enable retrieval of an attributes set together with at least one respective sequence template.

The term "multiple sequence alignment", "MSA" or "alignment" shall have the ordinary meaning as used by the skill person in the art of bioinformatics. CLUSTAL W is typical software package used for that purpose, and can be utilized by usage of default values and other values being adapted for the particular dataset in hand.

The term "synthetic context sequence" or "predicted context sequence" shall mean at least one context sequence or sequence template representing said context sequence that was identified by the systems and methods of the present invention, as statistically associated with an attributes set of interest.

Embodiments of the invention can be used in a general purpose computer system suitably adapted and designed for performing the extensive context sequences clustering, enrichment analysis and comparison.

Section I

FIG. 1 illustrates, in accordance with one embodiment of the present invention, an exemplary system on which the present invention may be implemented. In an embodiment, the computerized system 100 permits clients or users to provide an attributes set of interest for analysis 135. Typically, the attributes set can consist of two or more attributes of interest.

The clients or users can further provide a dataset of context sequences 105 as input information; thereby obtaining a dataset of context sequences for analysis. The context sequences can typically further comprise a set of gene names or unique identifiers which are operably linked or affected by the context sequences, respectively. The attributes set of interest 135 and context sequences 105 can be entered via a user interface specifically configured for that purpose. Where the system 100 is implemented on a computer network, the attributes set 135 and context sequences 105 can be provided through a browser application, such as, but not limited to web browsing application. Alternatively, the attributes set 135 or the context sequences 105 can be comprised in a file. The file can be uploaded to the system 100 though either a network or other information uploading methods known in the art for that purpose.

The context sequence clustering module 110 clusters the context sequences as described hereinafter. Typically, the dataset of context sequences 105 comprises a huge amount of sequence information. In turn, each context sequence is transformed into a sequence template. Clustering of the dataset of sequence templates is performed and results with plurality of clusters. In turn, each gene cluster or the genes which are regulated or affected by the context sequences within the cluster, is subjected to functional appraisal. The result of the functional appraisals is a plurality of clusters each statistically associated with their respective attributes set. The system and method of the present invention enables obtaining of heterogeneous clusters, as defined below.

The clustering procedures of the present invention are, inter alia, utilized in order to obtain a repository of attributes sets, statistically associated with a sequence template. Optionally, the sequence template represents two of more context sequences. The later may not be identical. Therefore, the clustering procedures of the present invention enable obtaining a heterogeneous repository, as defined hereinafter.

The clustering procedures of the present invention can use a 2-dimensional distance matrix to store and retrieve distance related information. However, in order to produce improved performance, distance related information is typically stored and retrieved from computer memory system comprising of plurality of heaps 130, or heap data structures. Data items which are stored and retrieved in the computer memory system 130 of the present invention typically comprise references pointing at two matrixes or templates and a real number. Each said templates represent a cluster of context sequences and the real number measures the distance between the clusters. Optionally, data items may further comprise information such as, but not limited to, gene names or unique identifiers of genes which were classified within the clusters. Alternatively, a template can further comprise information such as gene names or unique identifiers genes which were classified within the cluster which is represented by the template.

Clustering of the present invention is typically performed by the clustering module 110. The context sequence clustering module 110 stores and retrieves data items from the computer memory system (or memory module) 130. The structure of the computer memory system is described below. In essence, the memory system is based on plurality of Heap data structure which was restructured and remodeled, as described below, to improve performance especially where large data set are in hand. For the purpose of the present application, the memory systems shall also be referred to as "multiple-tree-array" the particulars of which are described below. The later typically comprises min heaps and adheres to the invariant according to which the top data item in the multiple-tree-array is a data item referencing a pair of templates having a minimal distance between them. The multiple-tree-array allows the system 100 to perform the clustering of the context sequences and enrichment analysis at an extremely efficient manner reducing the complexity by about one order in comparison to typical 2-dimensional distance matrixes.

The enrichment analysis module 120 performs enrichment appraisals or functional appraisals as described below. In an embodiment, the context sequence clustering module 110 sends a request to the enrichment analysis module 120. The request comprises a data set of context sequences or unique identifiers representing the context sequences within a cluster or unique identifiers of genes regulated or otherwise affected by context sequences. The request typically channeled through either a communication port, BUS or a computer network 115 to the enrichment analysis module 120.

In an embodiment, clusters of context sequences together with their respective enrichment appraisals can be stored in or retrieved from a repository or database 125. In an embodiment, the results of enrichment appraisals are represented by an attributes set or function attribute array being associated with respective cluster or clusters.

The function array comparator 140 is adapted to compare the attributes set of interest (typically provided by a user), with said stored enrichment appraisals retrieved from the repository 125.

Figure 2B:
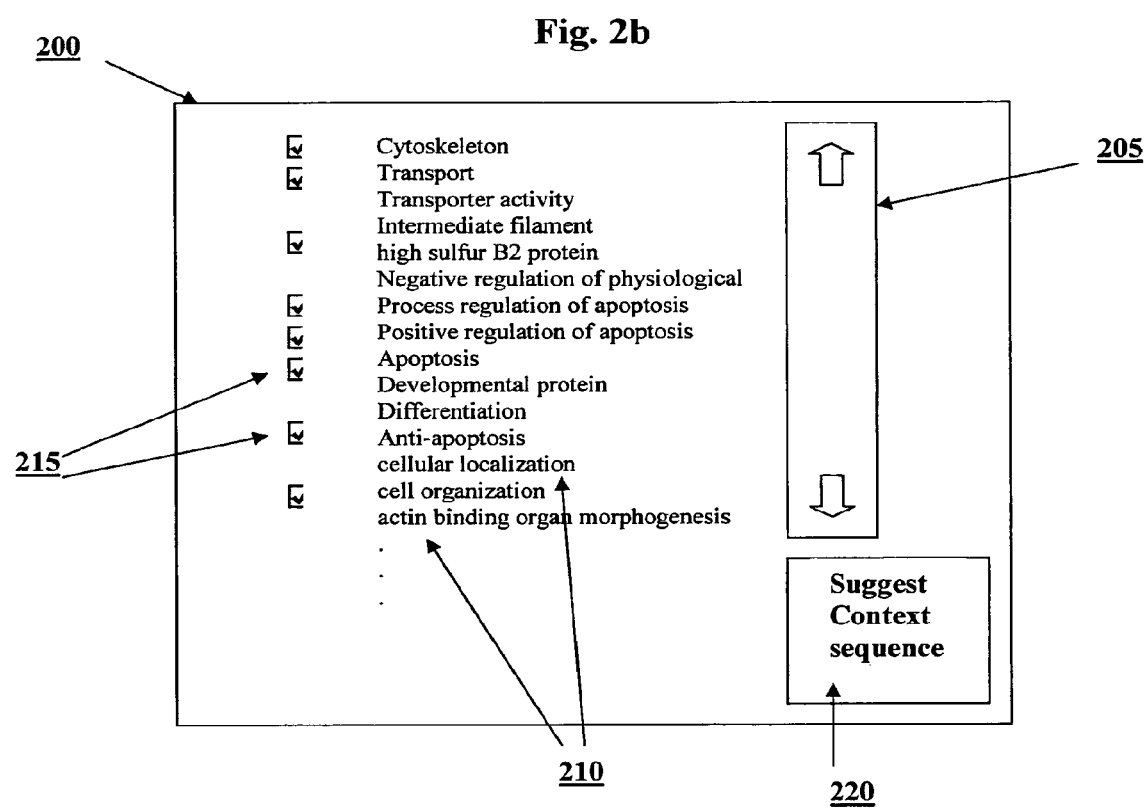
FIG. 2b illustrates, in accordance with one embodiment of the present invention, an exemplary user interface for obtaining a function array or attributes set of interest which is optionally provided by a user.

FIG. 2a and FIG. 2b illustrate, in accordance with one embodiment of the present invention, an exemplary user interface 200 for obtaining an attributes set of interest from a user. As an alternative, an attributes set is obtained from a client over the network (not shown). The client may be local or remote, either human or automated procedure performed on a computer system. Typically, the user select an attributes set from a list of function attributes 210. The list of function attributes contains at least a sub set of a complete function attributes set. In one embodiment, the user selects the function attributes of interest in order retrieve a sequence template statistically associated with his selection.

The sequence template retrieved can be used in order to design a context sequence for the purpose of either synthesis or manufacture of polynucleotide construct, or vector. In a one embodiment, the context sequence designed comprises the most dominant nucleotide in each position along the sequence template retrieved. In another embodiment, the context sequence designed comprises 80%-85%, 85%-90%, or 90%-100% homology with sequence template or the sequence comprising the most dominant nucleotide in each position along the sequence template.

The subset of function attributes selected by the user can be represented by a function attribute array or the attributes set. The manual selection can be performed with checkboxes 215 which indicate whether a particular function attribute was selected. As the complete function attributes set stored in the computerized system 100 may exceed the page size, page scroller 205 can provide means for navigating through the entire list of function attribute. The list of function attributes can be organized by several techniques, such as but not limited to, lexicographical order, classification, or source of the function attribute. In another embodiment, the user interface includes textboxes 220 in which a user enters the importance degree or confidence level associate with a particular function attribute.

The system of the present invention is adapted to retrieve an enrichment appraisal previously stored in the repository. The enrichment appraisal typically shares a similarity with an attributes set of interest. In another embodiment, the system of the present invention is adapted to retrieve an enrichment appraisal which shares similarity with an attributes set of interest at a predetermined threshold. Alternatively, the system of the present invention is adapted to retrieve an enrichment appraisal which shares maximal similarity with an attributes set of interest.

The output 150 comprises a cluster of context sequences or a sequence template representation thereof, which is statistically associated with said retrieved enrichment appraisal(s). In an embodiment, the output 150 comprises a cluster of context sequences or sequence template representation thereof which are statistically associated with said retrieved enrichment appraisal(s).

Those skilled in the art would appreciate that the invention may be practiced with other computer based system configurations, including network PCs, or hardware specifically designed to perform the procedures and functionalities contemplated hereinafter. The invention may also be practiced in distributed computing environments where procedure of the present invention is performed by remote dedicated processing devices that are linked through a communications network. In a distributed computing environment, for example, program modules such as 110, 120, 125, 130, and 140 may be located in both local and remote apparatus.

The components shown in FIG. 1 are only examples, and are not intended to suggest any limitation as to the scope of the functionality of the invention; the invention is not necessarily dependent on the features shown in FIG. 1.

FIG. 3 illustrates, in accordance with one embodiment of the present invention, an exemplary user interface 300 providing an identified context sequence 310 or a sequence template representing a cluster of context sequences statistically associated with the attributes set of interest. Typically, the identified context sequence or the sequence template consists of those which are statistically associated with stored attributes sets sharing maximal similarity with the attributes set of interest. Similarity or similarity degree is determined by the method described below.

In an embodiment, the user interface 300 includes a textbox, label, or information box 320. Each context sequence 310 or sequence template (not shown) can be associated with textbox, label, or information box 320. The textbox, label, or information box may include statistical confidence level of the context sequence such as p_value or a false discovery rate (FDR) or other enrichment estimator. The page scroller 305 can provide means for navigating through the entire list of context sequences where, for example, the predicted context sequences exceed the window size of the user interface 300.

FIG. 4 illustrates, in accordance with one embodiment of the present invention, another exemplary user interface 400 consists of a sequence template 410 representing a cluster of context sequences, said statistically associated attributes set 420 and the size of the cluster 430. Typically, the user interface 400 can be reached be double clicking on a predicted context sequences 310. The distribution table 415 can comprises a matrix representing the probability of a given nucleotide at a particular position along the context sequences of the current cluster viewed. Each column can represent a position along a predicted context sequence. The most dominant nucleotide at a particular position along the identified context sequences can appear at the top of the respective column 410. Where two nucleotides share similar of identical dominance level both can appear at the top of the respective column 425.

In another embodiment, the user interface 400 is utilized for viewing the clustered context sequences 410 comprising polypeptide sequences. In such an embodiment, the distribution table 415 can comprise a matrix representing the probability of a given amino acid at a particular position along the predicted context sequence. Each column can represent a position along a predicted context sequence. The most dominant amino acid at a particular position along the predicted context sequence can appear at the top of the respective column 410, while two amino acids sharing similar or identical dominance levels both can appear at the top of the respective column 425.

FIG. 5 illustrates, in accordance with one embodiment of the present invention, an exemplary data structure of a function attribute array or the attributes set 500. The attributes set 500 typically features a matrix of cells or items 510. Each of the cells in the matrix can comprise several fields or objects. In an embodiment, the first field of object is a function name/attribute 520 and the second is a value 530 associated therewith. The value 530 may optionally represent a Boolean variable. In an embodiment, where a Boolean variable in a cell holds #true, for example 530, the attributes set includes the particular attribute 520. On the other hand, where a Boolean variable in a cell holds #false the attributes set does not include the particular attribute. In another embodiment, value 530 can be represented a Real variable which represents the statistical confidence level of the particular attribute. By way of non-limiting example, where value 530 hold "1.0E-17", the function attribute array highly likely to include a particular attribute 520. On the other hand, if value 530 hold "1.0", the function attribute array most likely does not include the particular attribute 520.

One of ordinary skill in the art would appreciate that the data structure of the attributes set can be varied almost indefinitely. Many other data structures can be employed for storing a subset of attribute. By way of non limiting examples, the attributes set may optionally be stored as a Dictionary or hash table. Other one limiting examples: array of pair <string, boolean>, or indeed a 2D matrix where one dimension is the function attribute and the other dimension is a value.

The attributes set of interest 135 can be represented by the function attribute array 500.

As a mere illustration of the functionality of the present invention, the user may seek to identify one or more sequence templates associated with an attributes set of interest. Assume that the user wishes to consider immunoglobulin and transcription regulation with respect to humans. The user selection of interest is transformed into an attributes set 135 which are typically represented by the function attribute array 500. The function array comparator 140 compares the attributes set received comprising the user selection with said stored enrichment appraisals. The later are retrieved from the repository 125, with respect to humans. Typically, the user can request retrieval of a stored sequence template which is statistically associated with the specific function attributes chosen by the user. Alternatively, the user can retrieve the context sequences which were clustered together, and represented by the template. The user may find it advantageous to design or synthesize polynucleotide or polypeptide sequences on the basis of their functional association.

Therefore, the system and methods of the present invention can thus be used in preparing a polynucleotide construct, comprising: identifying a sequence template as statistically associated with an attributes set of interest by a user or client; and preparing a polynucleotide construct having at least one portion operably linked to a context sequence; wherein said context sequence is characterized as having either 80%-85%, 85%-90%, or 90%-100% homology with said sequence template. The user may wish to synthesize said context sequence, by utilizing any synthesis method known in the art for that purpose. Alternatively, the user may construct an expression vector comprising said context sequence or prepare a probe comprising the identified context sequence.

Homology in the range of X %-Y % shall be defined as identity score in the percentage range of X %-Y %. Said identity score is typically provided by an alignment analysis program. The alignment analysis can be performed using a numerous commercial sequence analysis packages, such as, but not limited to WATER (Smith-Waterman local alignment) provided by EMBOSS (European Molecular Biology Open Software Suite) operated with either default values or open gap penalty: 11, extended gap penalty: 0.5, and the default EDNAFULL or BLOSUM62 similarity matrix. Therefore, Homology in the range of %80-%100, as an example, shall mean that an identity score which ranges between 80%-100% using WATER according to the parameters set above.

Without limiting the applications of the presently described, the system described above is further adapted to execute the methods described hereinafter. In particular, the method for obtaining a repository of attributes sets, wherein attributes sets are statistically associated with a sequence template representing two or more context sequences, and the method for identifying a sequence template as statistically associated with an attributes set of interest.

Section II

The K-Means algorithm and its derivatives require the initial input of k-criterion from the user. For some clustering purposes, as the present purposes, the initial input of k-criterion is simply not known. For example, the user might not know how many clusters (k) will achieve well separated clusters enriched with functional attributes. It may well be any of $1 \geq k \geq N$ possibilities; for example where N=16,000 there are 16,000 possibilities.

Furthermore, the results of the K-Means algorithm are extremely sensitive to the initial random selection of cluster representatives. It was recently demonstrated that the worst-case running time of K-Means is super-polynomial i.e. $2^{\Omega(\sqrt{n})}16$.

Therefore in one of its embodiments, the present invention utilizes a different computer implemented method (hereinafter: "LBDL (Lower Bound Distance Limit) clustering method"). The LBDL is preferably used for large datasets e.g. N>16000 context sequences, and/or where no prior information relating to the suitable number of clusters is available i.e. k is unknown. While LBDL is preferred over K-means for example, the present invention is not limited to a particular clustering algorithm and may in fact optionally be implemented with any type of clustering.

Accordingly, the LBDL clustering method of the present invention does not require k-criterion at all. Instead, it requires a lower bound distance limit (LBDL) between clusters, as detailed below. This lower bound criterion is advantageous because it encapsulates actual practical meaning to the person skilled in the art i.e. distance between clusters of nucleic or peptide sequences.

The LBDL Clustering Method and Implementation Considerations

For the purposes of the present invention, "lower bound distance limit" shall mean a predetermined real number representing the lower bound distance limit.

For the purposes of the present invention, "lower bound distance limit invariant" shall mean the following invariant (hereafter: the LDBL-invariant): during the execution of the computer implemented LBDL clustering method, clusters will not merge where the distance between them is greater than a given distance limit.

In the present invention "data item", "heap item", or "(i,j,d(i,j))" shall mean a data item in a memory structure comprising (i) representing a first template, (j) representing a second template, and d(i,j) the distance between the templates. One of ordinary skill in the art would appreciate that the data item can be presented be other means such as, but not limited to, other data items, or differently ordered data items, all which essentially hold the template information and distance information relating thereto.

The LBDL method is provided hereinafter. In essence, each sequence under analysis is transformed to an information node or, as exemplified below, a sequence template. The algorithm efficiently performs merger operations, until satisfaction of the LBDL criteria. Each unraveled cluster is in turn subjected statistical functional appraisal. Each sequence template representing a cluster of context sequences is stored together with the associated results of the functional appraisal in a repository:

---

For the purposes of the present application '//' shall mean a comment or remark.
1.   for each context sequence in dataset allocate a template
// representing the distribution of nucleotides along the sequence.

-continued

```
This step is an initialization step in which each context sequence respectively
represented by a template. A particular embodiment or template representation is
detailed below.
        2.      for each pair (i,j), i ≠ j,i,j ∈ {Context - sequences - in - dataset}
        3.              insert (i,j,d(i,j)) into a multiple-tree-array.
// In steps 2-3 the distance between each pair of templates is measured. Each pair
of templates is then inserted into a multiple-tree-array together with the distance
between them. For clarification (a,b,c) of step 3 represents an abstract data
structure or data item typically comprising 3 numbers, two of which are
identifying a pair of templates and the third is a distance measurement between
them.
        4.      prevMin = −1: List CurMin= Empty List;
// initialization of variables
        5.      While ( ! multiple-tree-array.empty( ) ) {// This is the main loop
        6.              min = multiple-tree-array.DeleteMin( );
// current minimal data item stored in 'min'. Retrieval of the minimal data item is
typically performed by executing DeleteMin( ) procedure on a multiple-tree-array
data structure. Multiple-tree-arrays are defined below and by definition the
minimal data item is an item having minimum distance held therein i.e. the data
item represents a pair of templates sharing the highest similarity.
        7.                      CurMin.Insert(min);
// Insert the minimal data item stored in the multiple-tree-array into CurMin (the
List data structure defined in step 4).
        8.                      if (min.distance > lower_bound_distance_limit) Break; }
// The main loop continues until the lower_bound_distance_limit criterion is
satisifed. The Lower Bound Distance limit is defined below. 'Break' shall mean
end loop i.e. continue to step 12.
        9.                      if (min.distance != prevMin) {
// '!=' means not equal. Therefore, where the condition of step 9 is satisfied, the
previously handled distance stored in 'prevMin' is not equal the distance of
current minimum distance i.e. 'min.distance'. CurMin holds all items which were
retrieved from the multiple-tree-array and are having same distance. This is done
to ensure concurrent and equal treatment of data items which share the same
distance.
        10.                     HandleCurrentTemplates(CurMin);
// As previously noted, CurMin stores all items which were retrieved from the
multiple-tree-array and are having same distance. HandleCurrentTemplates( ) is a
procedure which is defined below, and in essence this procedure which handles
the merger operation(s) of the currently handled cluster(s).
        11.                     prevMin = min.distance ; CurMin.Empty( );}
// As all items of CurMin were handled by HandleCurrentTemplates, initialization
of the variables is required to verify that CurMin is empty. 'Empty( )' is typically a
procedure which empties the CurMin List. 'prevMin = min.distance' updates the
"previous" minimal distance with the current one (in turn the "current" is the
"previous" in the next steps).
        12.     Subject each remaining template to a functional appraisal.
// each cluster of context sequences which is represented by a sequence template
are subjected to a functional appraisal. This is typically performed by first
retrieving the names or unique identifiers of genes regulated or affected by the
context sequence within a cluster; and secondly, executing functional appraisal on
the names or unique identifiers retrieved.
        13.     Store <Cluster, functional appraisal results> in a repository;}}
```

In an embodiment, each sequence template(s) or context sequence(s) clusters are stored in a repository together with the associated functional appraisal result. The functional appraisal result can be stored or represented as an attributes set or a list. In an embodiment, the associated functional appraisal is represented by the function attributes array 500. The method therefore obtains a repository of attributes sets, where the attributes set is statistically associated with a sequence template or cluster of context sequences represented thereby.

Typically, a sequence template represents a cluster of two or more context sequences. The later may be either identical context sequences or typically context sequence consisting of different sequences. Moreover, the attributes set associated with a cluster of context sequence(s) can consist of two or more attributes.

A given cluster may also be associated with a particular attribute even where at least one of the context sequence (or gene affected thereby) is not characterized by the attribute. In other words, a cluster may be deemed as statistically associated with an attribute by functional appraisal even where a specific context sequence within the cluster is not particularly characterized by that attribute.

Therefore, a cluster in the present invention may therefore be deemed as a heterogeneous cluster. For the purpose of the present invention "homogeneous cluster" shall mean a context sequence cluster (or sequence template representing said cluster) wherein all context sequences in the cluster are of identical sequence. Alternatively, the term homogeneous cluster shall encompass a context sequence cluster (or sequence template representing said cluster) wherein all genes/context sequences in the cluster are characterized by an attribute. A "heterogeneous cluster" shall mean a sequence context (or sequence template representing said cluster) which is not a homogeneous cluster. In other words, a cluster exhibiting either: (1) at least one pair of non identical context sequences, or (2) statistical association to an attribute wherein at least one gene/context sequence is not characterized by the attribute.

A "heterogeneous repository" shall refer to a repository comprising at least one heterogeneous cluster. Examples 1 to 4 exemplifies numerous heterogeneous clusters detailed in Tables 1 to 4.

In an embodiment, either steps step 12 or 13 further comprise the step of discarding those attributes where the functional appraisal resulted with P_value greater than 0.3, 0.2, 0.1, and preferably greater than 0.05. The person skilled in the art would appreciate that other P_values can be selected for a particular data set in hand.

The lower bound_distance_limit (LBDL) can be set to various values depending on the distance formula used and the sought degree of separation between the clusters. Where the distance formula used is d(V,W) (defined below) and (l) denotes the length of the context sequences, the LBDL can range between 2%×(2 l) to 5%×(2 l), 5%×(2 l) to 20%×(2 l), or 20%×(2 l) to 55%×(2 l). The later is the most preferable as an initial configuration for analysis.

In a one embodiment, the dataset of context sequences is further subjected to multiple sequence alignment. The person skilled in the art would understand multiple sequence alignment can result in gap insertions which in turn may lengthen the length (l) of the context sequences.

By way of an illustration of LBDL invariant, observe the following aligned sequence population (N=2540):
I) 2000 sequences comprising: "AAAAA"
II) 500 sequences comprising: "GGGGG"
III) 30 sequences comprising: "TTTTT"
IV) 5 sequences comprising: "TATAT"
V) 5 sequences: "GTGTG"

With the knowledge that the size of the population is 2540, it is difficult to predict that k=5 (i.e. 5 clusters) will produce well separated clusters of gene sequences (why not try k=6, 7, . . . 1001 and so forth). This is, of course, an exemplary instance. In reality, it may well be that k=1001 will be produce reasonably separated clusters in the vector space.

If the user would enforce k=2 (i.e. two clusters), the K-Means algorithm will cluster the population as follows:
A) 2000 sequences having "AAAAA" as central representative.
B) 540 sequences having effectively "GGGGG" as central representative.

Groups III-V are therefore completely ignored. This might be an unacceptable result. The LBDL clustering method of the present invention avoids this problem. In this regard, ignoring clusters of genes simply because they are relatively small in size is inappropriate and unacceptable because even clusters consisting of even just a few genes may well have great value.

With respect to the above clustering example, assume that the invariant ensures that LBDL=ϵ>0, ϵ represent a real number having a positive and almost zero value. For that Lower Bound Distance Limit, the only possible sequence mergers occur among identical sequences i.e. where the distance is 0≤ϵ. Merging the identical sequences together will result in the original clusters I-V.

In order to perform the clustering of the context sequences, parameterization of each context sequence is required. For that end, at the initialization stage of the clustering method, each context sequence typically requires transformation into a corresponding sequence template.

Distance measurements (d) between any pair of templates V and W can be performed as follows:
d←0
for each i: 0 to l−1
  for each a∈{A,T,G,C}
  {d+=|V[a,i]−W[a,i]|$^2$}
Wherein: (l) denotes the length of the context sequences or alternatively the length or the aligned context sequences.

One of ordinary skill in the art would appreciate that these different distance formulas can be used for the purposes of the present invention. By way of non-limiting example, the distance calculation procedure can be varied such that the fourth step would comprise d+=|V[a,i]−W[a,i]|. Alternatively, the distance calculation procedure can be varied such that the fourth step would comprise d+=|V[a,i]−W[a,i]|$^t$, t∈N.

Merger of a pair of context sequence clusters V' and W', which are respectively represented by sequence templates V and W, can be defined as follows: The function Merge/Cluster creates and/or returns a sequence template T, representing the cluster T' consisting of both the context sequences of V' and W' (i.e. T'=V'∪W'). The sequence template T would hold the following matrix $T_{4 \times l}$ as follows:
for each i: 0 to l−1
  for each a∈{A, T, G, C} perform:

$$\left\{ T[a, p] = \frac{|A| \cdot V[a, p] + |B| \cdot W[a, p]}{|C|} \right\}$$

This merger procedure can be referred to as "merge", or "merger".

In an embodiment, the above merger procedures can handle a merger of more than two context sequence clusters by using sequential merger procedures. By way of non-limiting example, merger of 3 templates may typically require 2 merger operations. As an illustration, the first merger can take place with respect to templates 1 and 2, the product of which can be denoted as new template 12'. A second merger can merge the new template 12' with template 3 thereby producing a single template 123' representing all the context sequences which were previously represented by the separate templates 1, 2 and 3.

Memory Allocation of Sequence Templates

Sequence templates as defined above may be designed as a data structure or object. The sequence template essentially represents a subset of context sequences from the dataset i.e. a cluster. The sequence template would, therefore, hold distribution information of each nucleotide at each position in the cluster. The sequence template will typically hold the specific sequences which are grouped together in the cluster represented thereby. Optionally, a sequence template further holds gene name(s) or unique gene IDs which are regulated or otherwise affected by the context sequences within the respective cluster.

At initialization, each sequence in the dataset is transformed to a sequence template.

Order of Merging Operations

For the purposes of the present invention "handling current templates", "HandleCurrentTemplate( )" and "HandleCurrentTemplates( )" shall have the following meaning. Before the algorithm handles the current templates, any pair of templates (or indeed the clusters represented thereby) having equal distances measured between them are preferably stored in CurMin List. The order of merger the clusters or templates representing them will take place according to the order-invariant as explained and exemplified below.

As described above, the order of merger operations according to the LBDL clustering method is dominated by the distance between the clusters. However, the context sequence dataset might include subsets of numerous clusters having equal or substantially equal distances. The initial order of these clusters or the order of the context sequence may affect to final results of the algorithm. Therefore, in an embodiment, the clustering method of the present invention aims at reducing the sensitivity of the algorithm to the initial order.

Figure 6:
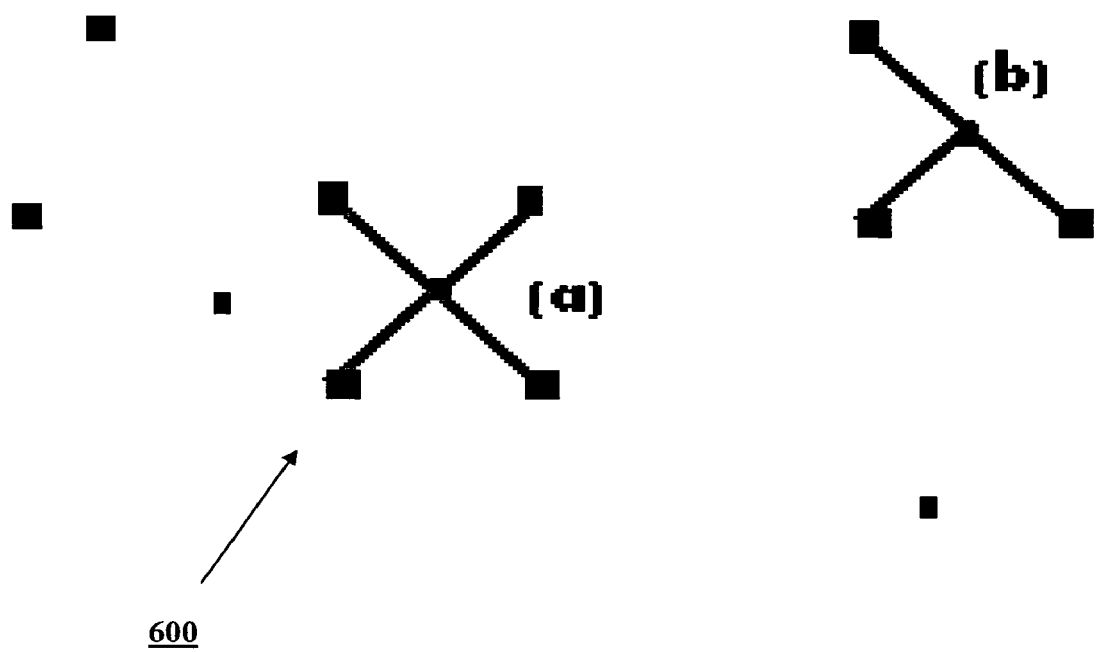
FIG. 6 illustrates, in accordance with one embodiment of the present invention, a simplified example of ascertaining the processing order of templates. (a) and (b) are two clusters of templates having equal minimum distances to a common template.

To that end, the cluster of context sequences which share equal are handled together without preferring arbitrarily any particular cluster. In particular, where pairs of clusters (or templates representing them) shares a common cluster and the distance between the pair clusters is equal, as illustrated in FIG. 6, they are handled together, as explained below. More formally: given the pair (i,j), and the pair (l,m), (i, j, l, and m are clusters), said pairs will thus be defined as sharing a common cluster if and only if i=l or i=m or j=l or j=m.

The following invariant will therefore apply (henceforth: the order-invariant): As any stage of the execution of a clustering method, the common template having maximum number of neighboring clusters will be the first to merge or be handle i.e. the largest "cluster" of clusters currently (held in CurMin List) will be merged first. Subsequently, the algorithm merges the rest of the currently handled templates according to the order-invariant.

FIG. 6 illustrates, in accordance with one embodiment of the present invention, a simplified example of ascertaining the processing order of templates. (a) and (b), for example, are two clusters of templates having equal distances to a common cluster.

Figure 7:
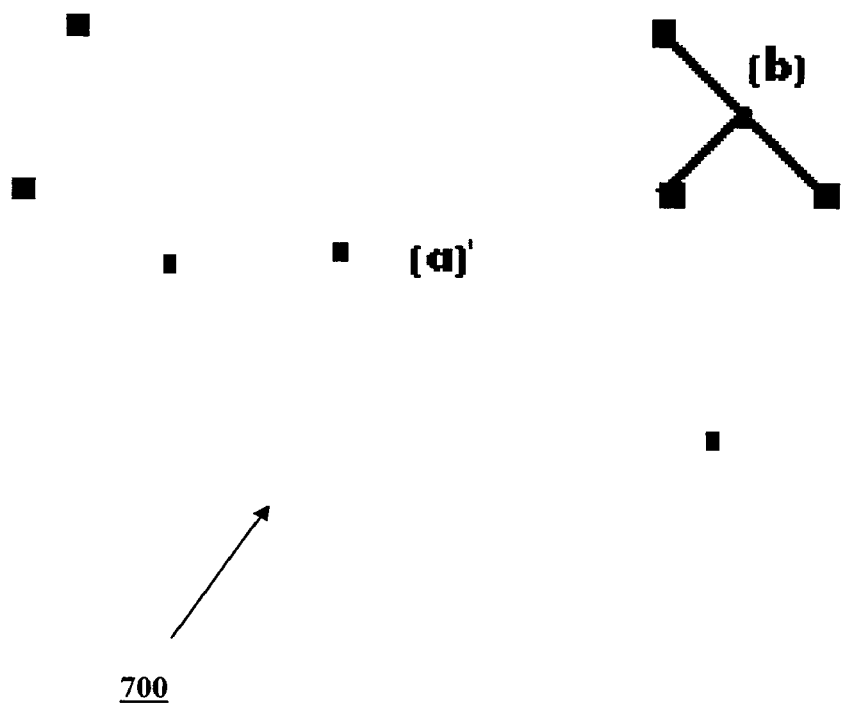
FIG. 7 illustrates, in accordance with one embodiment of the present invention, a Simplified example of ascertaining the processing order of clusters. (a') is a new cluster representing a merger of closest neighbors of (a) which was shown in FIG. 6, and (b) is to be handled subsequently.

Observe that common template (a) has 4 neighbors and while the central representative of cluster (b) has only 3 neighbors. Therefore, cluster (a) will be processed first. FIG. 7 illustrates the application of the order-invariant according to which cluster (a), previously shown in FIG. 6, was merged prior to handling of cluster (b). As a result, (a') is a new cluster representing the merger, and (b) is to be handled subsequently according to the order-invariant.

Following the merger operation, the multiple-tree-array is typically updated with all new distances between the pre-existing cluster (or templates representing them) and the newly merged templates.

For each pair of templates (i,j) where the d(i,j)>LBDL, the newly created (i,j,d(i,j)) need not be stored in the multiple-tree-array and can be totally ignored as explained before.

Otherwise, new heap item (i,j,d(i,j)) is inserted into the multiple-tree-array, with a single proviso. Said insertion should takes place unless the distance d(i,j) is lower than min.distance, defined above. In that case, the handling of data items which are held in. CurMin List is temporarily suspended and these data items are re-inserted to the multiple-tree-array.

For example, assume the following data items are held in multiple-tree-array, as follows: (1,5, 120), (5,3, 120), (4,6, 120), (7,4, 125), (1,7, 126), (8,2, 130). Only the first 3 data items will be currently retrieved. These data items share equal distances (120) which is the minimal in the dataset. At a given stage in the execution of the method, these three data items will be held in CurMin List and will be handled together. As the rest of the heap items encapsulate greater distances i.e. 125, 126, and 130, they will be processed later on.

In an embodiment, sorted dictionary data structure is utilized in order to provide fast identification of a common template having the maximal number of neighboring templates. By way of non-limiting example, assume the sorted histogram data structure has the follow data structure: <number of template appearances, sequence template reference>. In the above exemplification, the 3 retrieved data items will generate the following histogram in Sorted dictionary: <2,5>,<1,1>,<1,3>,<1,4>, and <1,6>. The neighbors of template 5 will merge first, under the order-invariant (template referenced as '5'; is the common template having maximum number of neighboring clusters).

Complexity Considerations

Utilization of the LDBL-invariant exhibited impressive complexity improvements:

(1) As LBDL based clustering method, by definition, does not require to merge clusters i, and j where the d(i,j)>LBDL, then (i,j,d(i,j)) need not be stored at all i.e. because the cluster pair i and j will never be merged or clustered together. Reduction of memory usage is therefore apparent.

(2) At any stage of the execution, if DeleteMin( ) procedure retrieves the global minimum which is greater (>) than the LBDL, it directly entails that the rest of the data items in the multiple-tree-array also exceed the LBDL. Therefore, the algorithm can be immediately terminated.

In another embodiment, the present invention utilizes a computer implemented method (hereinafter: "Vector Space clustering method"). Alternatively, the VS clustering method is used for performing clustering which is a variant of LBDL method shown above. This VS method is particularly useful where the length of the context sequences is in the range of 3-17 characters. The skilled person in the art would recognize that range is largely affected by computation time, which is associated with the length, and the computer system employed. Computer systems having high computation capabilities may process context sequences of greater length, including but not limited to the range of 10-15, or even 10-20 characters.

The VS clustering method:

1.     for each $c = (a_1 a_2 a_3 ... a_l), a_i \in \{A,T,G,C\}, 1 \geq i \geq l$ {
    // for each possible sequence in the vector space of length (l).
2.     List Cluster = null;
3.     for each i ∈ {Context - sequence - in - dataset} {
4.         double distance = d(c,i);
    // calculate the distance between c and i
5.         if (distance <= lower_bound_distance_limit) {
    // cluster together context sequences, if the distance between them fall within the lower_bound_distance_limit
6.             Cluster.Insert(i);}
7.         Subject Cluster to a functional appraisal;
// each cluster of context sequences which is represented by a sequence template are subjected to a functional appraisal. This is typically performed by first retrieving the names or unique identifiers of genes regulated or affected by the context sequence within a cluster; and secondly, executing functional appraisal on the names or unique identifiers retrieved.
8.         Store <Cluster, significant functional appraisal results> in repository;}}

In a one embodiment, step 1 is replaced with: "for a given sub set of each $c=(a_1 a_2 a_3 \ldots a_l), a_i \in \{A, T, G, C\}, 1 \geq i \geq l$;". In this manner, the method is utilized for a particular subset of context sequences of interest. The latter embodiment can be used to loop through a subset of possible sequences instead of looping through the entire vector space of possible sequences. This may be advantageous for achieving more efficient execution time in cases, for example, that some sequences are known not to feature substantial sequence patterns or important functional characteristics.

The VS differs from the LBDL in several aspects. For example, each context sequence in LBDL is classified into a single cluster. On the other hand, VS may classify each context sequence is several clusters. In that respect CVS is a "softer" classifier which sometimes can be advantageous because a single context sequence may be associated with multiplicity of functional attributes or attributes set. Another difference lies in the fact that VS typically spans thorough the entire vector space of all possible sequences i.e. even sequences which are absent from the context sequences of the data set. This is especially advantageous where synthetic or predicted sequences cannot be found in vivo. This is exemplified in the Step 1, where the analysis is performed for each (c) representing a possible sequence (not necessarily a context sequence of the data set).

Section III

The present invention, in some embodiments, relates to an implementation of specialized memory structures and processes for computations. These structures and processes may optionally be implemented with the embodiments described above and/or may also optionally be used independently.

Memory Module for Holding Parameterized Information

Traditionally, the easiest and most straight forward approach to manage distance information of a dataset is a "distance matrix". The later typically comprises 2D matrix of distances, such that each cell in said matrix holds the distance between a pair points of a set. A distance matrix is typically a symmetric N×N matrix containing real numbers as elements, given N points in a set. However, in large data sets, as might occur in the present case, the distance matrix performance is unacceptable. The performance time of retrieving the minimal or maximal element stored in the distance matrix is impractical for large data sets i.e. time for retrieving minimal/maximal element stored in the distance matrix.

Consider an exemplary size of the context sequences data set having N=16,000 i.e 16,000 context sequences. The matrix size would supposedly be $O(N^2)$ because the distance information represents all pair of said context sequences data set. Utilizing distance matrix would entail a typical retrieval time of a single minimal (or maximal) element in time complexity of $O(N^2)$. This renders the 2D distance matrix as unfavorable for use in the present invention, especially in case of large datasets.

In the present invention, "key" is a parameter within a data field comprising a value stored within a data item, or node. Preferably, key is a parameter capable of at least semi-order. By way of non-limiting example, a key may comprise a real number stored in a data item. Where (A) is data item, "KEY(A)" shall mean the parameter within a data field of data item (A). As an example, the key in a data item (i,j,d(i,j)) of the present invention can be the field consisting the distance between the pair of clusters i and j.

"heap" is a data structure based of tree topology that satisfies a general heap invariant as follows: For each pair of elements, items or child nodes in a heap, X and Y: where X is a child node of Y, then KEY(Y)≥KEY(X) i.e. The node having the maximum value as key ("greatest element") is the top node (or root node) of the heap. This heap is typically referred to a max-heap. Where KEY(Y)≥KEY(X), the smallest element is always the top node, and the heap is referred to as a min heap. "DeleteMin( )" or "deletion" shall mean removing and retrieving the root node of a min-heap. "Insert( )" or "insertion" shall mean adding a new element to a min heap. Heap shall further mean as defined in Corman et al[17] which is incorporated herein by reference.

A min heap provides an efficient data structure in which retrieving a minimal element is performed at O(log N). The latter is clearly more efficient in comparison to the traditional distance matrix at about 2 orders in magnitude.

For large data sets, however, a min heap is utterly inappropriate. To hold the complete distance dataset in a min heap is impractical. A PC having 1 GB available RAM and equipped with 3 GHz Intel Pentium processor can handle a min heap of about 300,000 data elements which means that data set cannot be greater than about N=600.

Therefore, in one of its aspects, the present invention provides a "multiple-tree-array" as defined and exemplified below. For the purpose of the present invention, "multiple-tree-array" shall mean memory module or data structure comprised therein employing plurality of tree topologies representing plurality of min-heaps, wherein the plurality of tree topology is managed through a common interface. There the present invention is directed to a computer memory system comprising a plurality of tree topologies representing plurality of (k) heaps, wherein the plurality of tree topologies is managed through a common interface; such that (k≥1).

Figure 8:
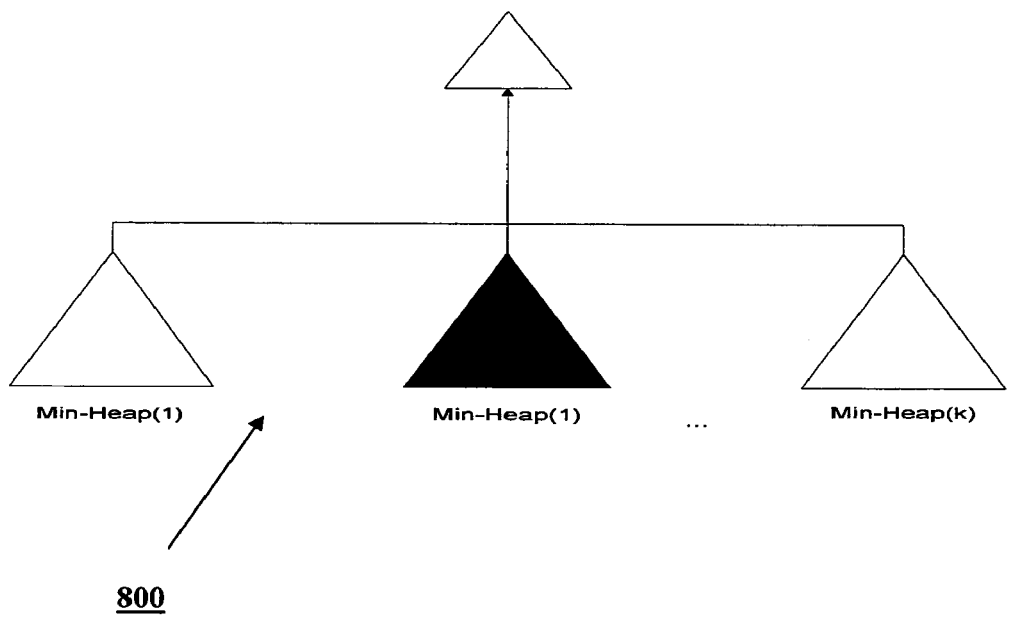
FIG. 8 illustrates, in accordance with one embodiment of the present invention, a multiple-tree-array topology within a memory module. The top item is defined as the element having the minimal key value amongst the (k) specific min heaps as shown.

FIG. 8 illustrates, in accordance with one embodiment of the present invention, a multiple-tree-array topology within a memory module. The top item, the item having the minimum distance, is the element having the minimal key value amongst the (k) min heaps as shown. Therefore, in one embodiment the computer memory system comprises min heaps.

The global minimum in the multiple-tree-array is defined as the minimal element (or minimal root element) amongst the min heaps comprising the multiple-tree-array. In other words, the minimal element is holding the minimal key value in comparison to all (k) min heaps which comprises the multiple-tree-array (hereafter: min-heap invariant). In one embodiment, the global minimum is the minimal distance between a pair of context sequences or sequence templates.

Figure 8A:
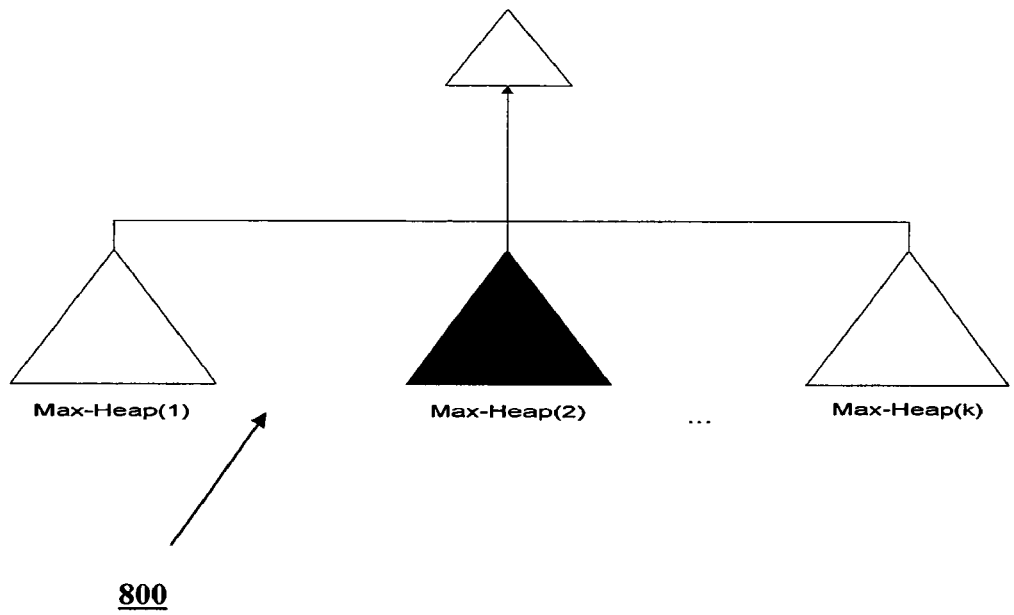
FIG. 8a illustrates, in accordance with one embodiment of the present invention, a multiple-tree-array topology within a memory module. The top item is defined as the element having the maximal key value amongst the (k) specific heaps as shown.

FIG. 8a illustrates similarly, in accordance with another embodiment of the present invention, a multiple-tree-array topology within a memory module. The root element, in this embodiment, is the element having the maximal key value amongst the (k) max heaps as shown. One of ordinary skill in the art would appreciate that while the multiple-tree-array is exemplified herein as a multiple-tree-array comprising min heaps and having a global minimal element, the present invention similarly relates to multiple-tree-array comprising max heaps and having a global maximal element.

In another embodiment, therefore the computer memory system comprises max heaps.

For the purposes of the present invention, "secondary storage" shall mean any data storage system performing slower than typical. RAM (Random Access Memory). Secondary Storage typically includes the non-volatile or semi-permanent storage in a computer environment. Common secondary storage devices are diskettes, hard drives, or tapes.

In an embodiment, each specific heap comprising the multiple-tree-array can be configured to operate as a conventional heap, either min- or max-heap. Insertion of a data item into the multiple-tree-array can be performed by invoking an Insert( ) procedure upon a specific min heap in the multiple-tree-array with one proviso. If the size of the specific min heap reaches a certain predetermined size threshold, another min heap which is selected for the insertion procedure. In the case where all min heaps reached the predetermined size threshold, additional memory comprising min-heap or max-heap is allocated to the multiple-tree-array memory module.

In one embodiment, said size threshold is in the range of 100-1000 elements, 1000-50000 elements, 50000-100000 elements, or 100000-350000 elements. In one embodiment, the element is a data item as defined above.

Deletion of a data item from the multiple-tree-array which comprises min-heaps can be performed by deleting the global minimum of the multiple-tree-array. As defined, global minimum is the minimal top element which holds the minimal key value in comparison to all (k) min heaps comprising in the multiple-tree-array. Following the deletion of the global minimum, the deleted element is replaced by an element from a specific min heap ensuring the heap invariant. That is ensuring that global minimum is the element which holds the minimal key value in comparison to all (k) min heaps comprising in the multiple-tree-array. Where the last element in a min heap is removed the min heap can be released from the multiple-tree-array memory module. Where all the min heaps in the multiple-tree-array memory module have removed their respective last top element, the entire multiple-tree-array memory module is deemed to be empty or null.

The multiple-tree-array provides storage and retrieval performed at the worst case time of O(k log n), where (k) in the number of heaps managed therein.

An "active min heap" and "active subset of min heaps" shall mean the min heaps which are stored in RAM, and at least one of the min heaps stores the global minimum of the multiple-tree-array. A "passive min heap" and "passive subset of min heaps" shall mean the min heaps which are held in secondary storage.

An "active max heap" and "active subset of max heaps" shall mean the max heaps which are stored in RAM, and at least one of the heaps holds the global maximum of the multiple-tree-array. A "passive max heap" and "passive subset of heaps" shall mean the max heaps which are held in secondary storage.

In another embodiment, an active subset of heaps is held in RAM, while the rest of the heaps are maintained on a secondary storage. In another embodiment, a subset of passive min heaps is maintained on secondary storage. In another embodiment, an active subset of max heaps is held in RAM, while the rest of the heaps are maintained on a secondary storage. In another embodiment, a subset of passive max heaps is maintained on secondary storage.

Special attention should be made for ensuring the dominance of the min heap invariant. Where DeleteMin( ) procedure retrieved and erased the global minimum from the multiple-tree-array, the next global minimum may be located at a passive min heap on secondary storage. Therefore, the min heap invariant cannot be ensured with a current active subset of min heaps. The multiple-tree-array is configured to replace or switch at least one of the active min-heap with at least one passive min heap (one of which is storing the current global minimum).

In one embodiment, a data item in a min heap array shall have at least the following members (i,j,d(i,j)) whereby i and j are pointers to respective templates (of the template matrixes) and the third member is a real number representing the distance between the templates i.e. the $3^{rd}$ field in the data item is the key, the common field as defined above.

In another embodiment, a template (or a context sequence represented thereby) can be erased or invalidated from the data set during the "life time" of the multiple-tree-array. The invalidation may occur upon merger of templates, as described in the present invention. The merger procedure typically entails invalidation of the merged templates. In such a case, at least one existing data item in the multiple-tree-array (i,j,d(i,j)) may be holding distance information relating to the invalidated template. Therefore, said existing data item requires in turn its invalidation or deletion. Typically, such invalidation would require O(2N) deletions of data items from the multiple-tree-array (N be the number of the cluster).

Therefore, in yet another aspect, the present invention is directed to a postponed deletion procedure or postponed invalidation procedure. The deletion is postponed until the operation of DeleteMin( ). The postponed deletion or invalidation of the data item is delayed until their respective deletion by the operation of DeleteMin( ). In other word, instead of searching for the data item for deletion, the multiple-tree-array "awaits" until the invalidated data item is retrieved, by operation of DeleteMin( ). Following the operation of DeleteMin( ), the retrieved data item (i,j,d(i,j)) is verified to be comprising valid data or valid templates (i) and (j).

By way of non-limiting example, validation procedure utilizes a one dimensional array of Boolean values (B) such that B[i] holds #true if and only if template (i) is of valid status. Alternatively, the validation procedure can utilize an array of other validation information such as but not limited to: a time stamp or a string representing a status.

Section IV

The computer implemented method of the present invention for identifying a sequence template as statistically associated with an attributes set of interest typically comprises: (a) providing a repository of attributes sets, said attributes set is statistically associated with a sequence template; (b) selecting an attributes set of interest; and (c) retrieving at least one sequence template statistically associated with said, attributes set. Typically, a sequence template represents two or more context sequences. Moreover, the attributes set can consist of two or more attributes of interest selected by a user or client. The retrieved sequence template of step (c) typically also represents two or more context sequences. Optionally, retrieved sequence template or cluster represented thereby is a heterogeneous cluster.

In an embodiment, the repository was obtained according to any method of the present invention. In particular, the repository can be obtained by utilization of the LBDL clustering method. In another embodiment, the repository was obtained by utilization of the VS clustering method. Optionally, the repository is a heterogeneous repository.

Attributes or function attributes of interest can be selected for from the group consisting: the Gene Ontology Project (GO), Interpro annotation (European Molecular Biology Laboratory, EMBL), SMART (a Simple Modular Architecture Research Tool, found at (smart.embl-heidelberg.de), UniProt Knowledgebase (SwissProt), OMIM (by NCBI) PROSITE (by the Swiss Institute of Bioinformatics), Protein Information Resource (PIR), GeneCards, and Kyoto Encyclopedia of Genes and Genomes (KEGG).

For the purposes of the present invention, "similarity", "similarity degree", or "sd" between any pair of function attributes arrays V, and W can be determined by the following procedure:

```
sd ← 0
For each a ∈ {complete - function - attributes - set} {
// for each attribute in the complete function attributes array,
sum up the differences or divergence between the respective
real values
if (V[a].value == #true and W[a].value == #false) {sd++;}
// as different increase the distance by 1
if (V[a].value==false and W[a].value==true) {sd++;}
}
```

Wherein:

(a)—represents a particular function attribute name; and V[a]·value—represents a value associated to particular function (a).

V and W comprises binary digits as values;

Where V and W comprises real numbers as values, "similarity" between any pair of function attributes arrays V, and W can be determined by the following procedure:

```
sd ← 0
For each a ∈ {complete - function - attributes - set}{
// for each attributes in the function attribute array, sum up
the differences or divergence between the respective real
values
sd+=| V[a].value − W[a].value |
}
```

Wherein:

(a)—represents a particular function attribute name; and V[a]·value—represents a value associated to particular function (a).

One of ordinary skill in the art would understand that either V and/or W may not comprise a particular function attribute. This scenario can be represented as: V[a]·value=null i.e. particular function attribute 'a' is not associated with V. In such a case, the value may be deemed to have a default value or another symbol which represent a null value.

In an embodiment, where the attributes array features an array of real numbers as values, '0.0' may be deemed to represents a non inclusion of a particular function.

In an embodiment, the above step of (sd+=|V[a]·value−W[a]·value|) can be performed if and only if (V[a]·value !=null and W[a]·value !=null). Thus, null valued attributes are ignored.

One of ordinary skill in the art would understand that similarity degree can be determined by the above distance measurement between a pair of function attribute arrays. However, many alternative approaches may be adopted to provide a measure of similarity between function attribute arrays.

For the purposes of the present invention, "functional significance appraisal", "functional appraisal", "attribute appraisal" and "functional significance test" shall mean refer to a computational method comprising a statistical test yielding confidence-level or probability, P_value that at least one function attribute is associated with a given gene cluster or gene cluster regulated or otherwise affected by context sequence(s).

The typical input for this computational method is the names or unique identifiers of genes regulated or otherwise affected by the context sequence within a cluster.

The typical result (or output) of functional appraisal is typically a list of attributes which can be deemed as statistically over represented within said input cluster. The list of attributes can further comprise the P_value or confidence level of an attribute within the list.

By way of another non-limiting example, the statistical test can be based on Fisher exact probability test, or hypergeometric (HG) probability distribution pertaining the sampling without replacement from finite population as explained hereinafter. By way of illustration, N typically denotes the entire size of the gene population (i.e. population size); n denotes the size of context sequence cluster under analysis (i.e. sample size); m denotes the number of genes in the entire population characterized by at least one function attribute (i.e. the "unique" group size); k denotes the number of unique items found in the cluster under analysis. For example, assume N=16,231, n=197, m=678, and k=20 the P_value is therefore 0.0001467. The hypergeometric distribution with parameters N, m and n, and k, can therefore define the probability of getting exactly k genes characterized by said function attribute in a cluster of input genes (or context sequence cluster regulating or affecting them).

Jackknife methodologies and other confidence assisting procedures can be added to increase the confidence level of the enrichment results. Functional appraisal tools can be purchased in, for example, (david.abcc.ncifcrf.gov)[18,19].

In one embodiment, the retrieval of a sequence template statistically associated with an attributes set of interest comprises: determining similarity between the attributes set of interest and each attributes set previously inserted into repository; and retrieving from the repository a sequence template associated with at least one attributes set previously inserted into said repository.

The repository can typically comprise (N) pair(s) of sequence templates and their associated attributes set: $<T_i, AS_i>$, $1 \geq i \geq N$, where $T_i$, and $AS_i$ are a sequence template and attributes set of the i-th record in the repository, respectively. The method of retrieval of a sequence template statistically associated with an attributes set (AS) of interest, can therefore be performed by: (a) determining similarity, by utilizing similarity formula such as, but not limited to $ds(AS, AS_i)$, as defined above; and (b) retrieval of $<T_i, AS_i>$, $1 \geq i \geq N$ from the repository together with the respective, $ds(AS, AS_i)$.

The order of retrieved records is preferably in descending order according to the similarity degree. The retrieved sequence template typically also represents two or more context sequences. The later may be either identical context sequences or typically context sequence consisting of different sequences.

Moreover, the attributes set associated with the context sequence(s) or sequence template can consist of two or more attributes. Optionally, the context sequence(s) or sequence template may be statistically associated with a particular attribute even where at least one of the context sequence (or gene affected thereby) is not characterized by the attribute. In other words, the retrieval procedures of the present invention therefore enable retrieval of heterogeneous clusters, as defined above.

The retrieval of a sequence template statistically associated with said attributes set, may comprises the steps of: determining similarity between the attributes set of interest and at least one attributes set previously inserted into repository; and retrieving from the repository a sequence template associated with the at least one attributes set previously inserted into said repository.

The repository can therefore typically comprise (N) of pair(s) of sequence templates and their associated attributes set: $<T_i, AS_i>$, $1 \geq i \geq N$, where $T_i$, and $AS_i$ are a sequence template and attributes set of the i-th record in the repository, respectively. The method of retrieval of a sequence template statistically associated with an attributes set (AS) of interest, can therefore be performed by: (a) determining similarity, by utilizing similarity formula such as, but not limited to $ds(AS, AS_i)$, as defined above; and (b) retrieval at least one of $<T_i, AS_i>$, $1 \geq i \geq N$ from the repository together with respective $ds(AS, AS_i)$. The order of retrieved records is preferably in descending order according to the similarity degree.

The retrieved sequence template typically also represents two or more context sequences. The later may be either identical context sequences or typically context sequence consisting of different sequences.

In the above embodiments, the method typically retrieves at least one sequence template together with a degree of similarity between the attributes set of interest and the attributes set statistically associated with the sequence template. However, filtering of at least one sequence template is typically required.

To that end, in another optional embodiment, the retrieving includes discarding a sequence template associated with said at least one attributes set, where the similarity between said at least one attributes set and the attributes set is above a predefined threshold (L). In that respect therefore, the retrieval further comprises discarding (or filtering out) records having $ds(AS, AS_i) \geq (L)$.

The threshold (L) can be set to various values depending on the number of results sought by the user or the client. As an alternative, the user or client may wish to retrieve the best result alone.

To that end, the retrieving step includes discarding a sequence template associated with said at least one attributes set, where the similarity between said at least one attributes set and the attributes set of interest is above the global minimum. In that respect therefore, the retrieval further comprises discarding (or filtering out) records having $ds(AS, AS_i) > \min_{1 \leq j \leq N}(ds(AS, AS_j))$.

In an embodiment, said retrieving includes discarding attributes (i.e. members of the attributes set) where the functional appraisal resulted with a respective P_value greater than 0.3, 0.2, 0.1, or preferably greater than 0.05. The person skilled in the art would appreciate that other P_values ranges can be selected for a particular data set in hand.

Following retrieval of the two or more sequence template statistically associated with said attributes set of interest, the method can further comprise merging at least two of retrieved sequence template (or clusters represented thereby). Merger procedure is detailed above.

Section V—Experimental Examples

This Section relates to experimental examples, illustrating the above embodiments of the present invention. These examples are provided for the purpose of illustration only and without any intention of being limiting in any way.

Example 1: *Arabidopsis Thaliana*

A. Dataset

The complete RefSeq sequences of plants mRNA was downloaded (www.ncbi.nlm.nih.gov/RefSeq). The database was filtered in order to exclusively include mRNA sequences of *Arabidopsis Thaliana*. The dataset was thereafter cleaned of duplicate genes to reduce over representation of identical genes. The translation initiator codon was identified using the Reveq CDS. Sequence in the length of 9 nucleotides preceding translation initiator codon were parsed, and indexed. The dataset thereafter included the total of 16,491 short sequences of 9 successive nucleotides. The complete dataset was aligned.

B. Application of the LBDL Clustering Method

The LBDL clustering method was applied on the mRNA dataset in 8 separate phases. In each phase the algorithm was provided with a different Lower Bound Distance Limit so as to cluster with varying degree of stringency (0.01; 2.01; 3.01; 4.01; 5.01; 6.01; and 7.01). The separate phase analysis provides an opportunity to investigate smaller more exotic clusters of genes before they merge into larger cluster and lose some significant functional properties along the way.

C. Significant Functional Enrichments of Plant Gene Clusters

Table 1 prescribes the emerging gene clusters which were identified by LBDL clustering method. This table includes selected clusters which demonstrated significant functional attributes.

The clusters in Table 1 are arranged according to size i.e. number of different genes in each cluster. For each cluster, said table provides a template comprising matrix $T_{4 \times 9}$, where the distribution of nucleotides for each position preceding the translation initiation codon. For convenience, the most frequent sequence of successive nucleotides, is disclosed i.e. the dominant context sequence.

The translation initiation codon is at position '0' and does not appear in the table. Table 1 includes a portion of results due the amount of information the LBDL clustering method extracted and collected.

For each template disclosed, the table provides the significant functions or functional attributes set associated with the template. The largest gene cluster includes some 1613 distinct genes. The second largest cluster has 1433 distinct genes. These clusters seem to support previous work which stipulated the A-rich conserved region in higher plants[20]. The large clusters were enriched, inter alia, with genes encoding nuclear and transcription related proteins, partially in contradiction to previous speculations[21]. Another observation is that the smaller clusters tend to be quite distant from the largest gene clusters. Smaller clusters tend also to include non-A nucleotides with distribution above 80%. For easier reference these nucleotides were highlighted in the body of the table.

As now shown in Table 1, the dominant context sequence 'tttttaaaa' is clearly associated for the first time with response to abiotic stimulus and further chemical stimulus. Moreover, a plurality of dominant context sequences are now associated with transcription regulation and transcription in general. For example, templates associated with transcription regulation consists, inter alia, of: 'aaaaaaaaa', 'gttaagaaa', 'ttttcttca' and 'gagagagaa'. Photosynthesis is associated with 'acaaaaaca', and also 'gaagaagaa'. This unravels the fact that as many as a single function can be associated to a plurality of context sequences or dominant context sequences with strong statistical significance. Table 1 illustrates plurality of other templates and their association with significant functional attributes.

The statistically supported association of functional attribute arrays with a template can be used both in research and genetic engineering.

Example 2: *Homo sapiens*

A. Dataset

The complete RefSeq sequences of Human mRNA were downloaded (www.ncbi.nlm.nih.gov/RefSeq). The database was filtered in order to exclusively include mRNA sequences of *Homo sapiens*. The dataset was thereafter cleaned of duplicate genes to reduce over representation of identical genes. The translation-initiator codon was identified using the RefSeq CDS. Sequence in the length of 9 nucleotides preceding translation initiator codon were parsed, and indexed. The dataset thereafter included the total of 17,053 short sequences of 9 successive nucleotides. The complete dataset was aligned.

B. Application of the LBDL Clustering Method

The LBDL clustering method was applied on the mRNA dataset in 3 separate phases. In each phase the algorithm was provided with a different Lower Bound Distance Limit so as to cluster with varying degree of stringency (5.01; 6.01; and 7.01). The separate phase analysis provides an opportunity to investigate smaller more exotic clusters of genes before they merge into larger cluster and lose some significant functional properties along the way.

C. Significant Functional Enrichments of Human Gene Clusters

Table 2 prescribes the emerging gene clusters which were identified by LBDL clustering method. This table includes selected clusters which demonstrated significant functional attributes.

The clusters in Table 2 are arranged according to size i.e. number of different genes in each cluster. For each cluster, said table provides a template comprising matrix $T_{4\times9}$ where the distribution of nucleotides for each position preceding the translation initiation codon. For convenience, the most frequent sequence of successive nucleotides, is disclosed i.e. the dominant context sequence.

The translation initiation codon is at position '0' and does not appear in the table. Table 2 includes only a portion of the results due the amount of information the LBDL clustering method extracted and collected.

The most significant functional enrichment of each cluster appears as well. The largest gene cluster includes some 1562 distinct genes. The second largest cluster has 987 distinct genes.

Another observation is that the smaller clusters tend to be quite distant from the largest gene clusters.

As now shown in Table 2, the context sequence 'gccagcacc' can be associated with response to pest, or pathogen. Importantly the same context sequence is statistically associated with immunoglobulin and the immune system. Moreover, plurality of context sequences are now associated with transcription regulation and transcription in general. For example, templates associated with transcription regulation consists, inter alia, of: 'cgcgggaag, 'ggaggaaaa', and 'ctgaagaaa'. Metabolism is statistically associated with 'cccgccgcg', 'agcctagaa' and also 'ctgaagaaa'. Again, as many as a single function can be associated to a plurality of context sequences with strong statistical significance. Table 2 illustrates plurality of other templates and their association with a significant functional attributes.

The statistically supported associating functional attribute arrays with a template can be used both in research and genetic engineering.

Example 3: Mus Musculus

A. Dataset

The complete RefSeq sequences of Mus Musculus mRNA was downloaded (www.ncbi.nlm.nih.gov/RefSeq). The database was filtered in order to exclusively include mRNA sequences of Mus Musculus. The dataset was thereafter cleaned of duplicate genes to reduce over representation of identical genes. The translation initiator codon was identified using the RefSeq CDS. Sequence in the length of 9 nucleotides preceding translation initiator codon were parsed, and indexed. The dataset thereafter included the total of 15,312 short sequences of 9 successive nucleotides. The complete dataset was aligned.

B. Application of the LBDL Clustering Method

The LBDL clustering method was applied on the mRNA dataset in 3 separate phases. In each phase the algorithm was provided with a different Lower Bound Distance Limit so as to cluster with varying degree of stringency (5.01; 6.01; and 7.01). The separate phase analysis provides an opportunity to investigate smaller more exotic clusters of genes before they merge into larger cluster and lose some significant functional properties along the way.

C. Significant Functional Enrichments of Plant Gene Clusters

Table 3 prescribes the emerging gene clusters which were identified by LBDL clustering method. This table includes selected clusters which demonstrated significant functional attributes.

The clusters in Table 3 are arranged according to size i.e. number of different genes in each cluster. For each cluster, said table provides a template comprising matrix $T_{4\times9}$, where the distribution of nucleotides for each position preceding the translation initiation codon. For convenience, the most frequent sequence of successive nucleotides, is disclosed i.e. the dominant context sequence.

The translation initiation codon is at position '0' and does not appear in the table. Table 3 includes only a portion of the results due the amount of information the LBDL clustering method extracted and collected.

The most significant functional enrichment of each cluster appears as well. The largest gene cluster includes some 1197 distinct genes. The second largest cluster has 710 distinct genes.

As now shown in Table 3, the context sequence 'gccgccgcc' can be associated with sh3 domain. Moreover, plurality of context sequences are now associated with metabolism in general. For example, templates associated with metabolism consists, inter alia, of: 'ccccgcgcc, and 'cggaggaag'. Metal ion binding is statistically associated with both 'gccgccgcc', and 'ccccgcgcc'. Again, as many as a single function can be associated to a plurality of context sequences with strong statistical significance. Table 3 illustrates plurality of other templates and their association with a significant functional attributes.

The statistically supported associating functional attribute arrays with a template can be used both in research and genetic engineering.

Example 4: Bos Tauros

A. Dataset

The complete RefSeq sequences of Bos Tauros mRNA was downloaded (www.ncbi.nlm.nih.gov/RefSeq). The database was filtered in order to exclusively include mRNA sequences of Bos Tauros. The dataset was thereafter cleaned of duplicate genes to reduce over representation of identical genes. The translation initiator codon was identified using the RefSeq CDS. Sequence in the length of 9 nucleotides preceding translation initiator codon were parsed, and indexed. The dataset thereafter included the total of 9,723 short sequences of 9 successive nucleotides. The complete dataset was aligned.

B. Application of the LBDL Clustering Method

The LBDL clustering method was applied on the mRNA dataset in 3 separate phases. In each phase the algorithm was provided with a different Lower Bound Distance Limit so as to cluster with varying degree of stringency (5.01; 6.01; and 7.01). The separate phase analysis provides an opportunity to investigate smaller more exotic clusters of genes before they merge into larger cluster and lose some significant functional properties along the way.

C. Significant Functional Enrichments of Plant Gene Clusters

Table 4 prescribes the emerging gene clusters which were identified by LBDL clustering method. This table includes selected clusters which demonstrated significant functional attributes.

The clusters in Table 4 are arranged according to size i.e. number of different genes in each cluster. For each cluster, said table depicts the distribution of nucleotides for each position preceding the translation initiation codon. For convenience, the most frequent sequence of successive nucleotides, is disclosed i.e. the dominant context sequence.

The clusters in Table 4 are arranged according to size i.e. number of different genes in each cluster. For each cluster, said table provides a template comprising matrix $T_{4 \times 9}$, where the distribution of nucleotides for each position preceding the translation initiation codon together with the most frequent sequence of successive nucleotides, is disclosed. Table 4 illustrates plurality of other templates and their association with a significant functional attributes.

The most significant functional enrichment of each cluster appears as well. The largest gene cluster includes some 815 distinct genes. The second largest cluster has 583 distinct genes.

Example 1-4 exemplify numerous heterogeneous clusters detailed in Tables 1-4 which were identified by the method and systems of the present invention.

TABLE 1

Emerging gene clusters which were identified by the clustering algorithm pertaining *Arabidopsis Thaliana*. The below clusters are arranged according to declining size. For each cluster, the table depicts the distribution of nucleotides for each position along the context sequence.

| Size of Cluster (number of context sequences) | Function attributes set (Enrichment score/P_value/Benjamini) | | Distribution of nucleotides per position along the context sequence (%) | | |
|---|---|---|---|---|---|
| | | Pos: | −9 | −8 | −7 |
| 1613 | membrane (9.88, 7.0E−17, 4.1E−14); transmembrane (9.88, 9.0E−14, 2.2E−11); transit peptide (6.7, 5.5E−12, 6.7E−10); chloroplast (6.7, 4.5E−9, 3.0E−7); plastid (6.7, 1.7E−6, 7.7E−5); signal (6.14, 4.7E−12, 6.9E−10); glycoprotein (6.14, 3.7E−11, 3.0E−9); response to abiotic stimulus (3.54, 3.3E−6, 3.3E−3); response to chemical stimulus (3.54, 1.1E−5, 7.1E−3); response to hormone stimulus (3.54, 2.2E−3, 4.7E−1); response to endogenous stimulus (3.54, 4.8E−3, 5.9E−1); metal-binding (3.54, 4.6E−12, 8.5E−10); iron (3.54, 8.0E−12, 8.4E−10); oxidoreductase (3.54, 1.1E−11, 1.0E−9); heme (3.54, 2.5E−8, 1.5E−6); monooxygenase (3.54, 3.6E−6, 1.5E−4); E-class P450, group I (3.54, 1.7E−4, 4.9E−1); dna-binding (2.77, 3.4E−4, 1.0E−2); nuclear protein (2.77, 1.4E−3, 3.5E−2); transcription (2.77, 3.4E−3, 6.8E−2); transcription regulation (2.77, 5.2E−3, 9.1E−2); ribonucleoprotein (2.26, 1.2E−9, 8.9E−8); ribosomal protein (2.26, 6.9E−8, 3.9E−6); structural molecule activity (2.26, 4.0E−5, 3.3E−2); structural constituent of ribosome (2.26, 8.9E−4, 3.9E−1); zinc (0.23, 8.8E−2, 5.8E−1); | A % T % G % C % | a 46.12 10.78 33.84 9.237 | a 71.60 9.051 13.63 5.703 | a 67.45 1.921 26.10 4.525 |
| 1433 | transit peptide (5.12, 2.7E−9, 5.0E−7); plastid (5.12, 1.9E−6, 1.7E−4); chloroplast (5.12, 9.5E−6, 5.8E−4); metal-binding (3.84, 2.9E−13, 2.2E−10); zinc (3.84, 8.4E−9, 1.2E−6); zinc-finger (3.84, 3.2E−8, 3.9E−6); response to abiotic stimulus (3.73, 7.1E−6, 7.2E−3); response to chemical stimulus (3.73, 6.4E−5, 4.2E−2); response to stimulus (3.73, 3.8E−4, 1.4E−1); response to endogenous stimulus (3.73, 7.2E−4, 1.9E−1); response to hormone stimulus (3.73, 1.9E−3, 3.5E−1); nuclear protein (3.5, 3.4E−11, 8.2E−9); dna-binding (3.5, 5.4E−6, 3.6E−4); transcription (3.5, 4.2E−4, 1.3E−2); transcription regulation (3.5, 1.5E−3, 3.6E−2); membrane (3.42, 3.4E−6, 2.5E−4); transmembrane (3.42, 1.7E−5, 9.4E−4); signal (2.61, 1.6E−7, 1.6E−5); glycoprotein (2.61, 3.6E−5, 1.8E−3); translation regulator activity (2.43, 1.5E−4, 1.2E−1); translation factor activity, nucleic acid binding (2.43, 1.5E−4, 1.2E−1); protein biosynthesis (2.43, 2.8E−4, 1.1E−2); response to external stimulus (2.31, 3.3E−4, 1.5E−1); defense response to pathogen, incompatible interaction (2.31, 4.9E−4, 1.5E−1); response to wounding (2.31, 2.5E−3, 3.7E−1); response to abscisic acid stimulus (2.17, 3.3E−3, 4.3E−1); response to water (2.17, 8.6E−3, 6.9E−1); peroxisome (2.05, 4.1E−4, 1.3E−2); gibberellin signaling pathway (1.97, 7.5E−4, 2.2E−2); zinc (1.89, 8.4E−9, 1.2E−6); zinc-finger (1.89, 3.2E−8, 3.9E−6); Nuclear protein (1.89, 7.5E−2, 5.5E−1); meristem development (1.81, 1.6E−3, 3.3E−1); elongation factor (1.8, 1.6E−3, 3.9E−2); translation elongation factor activity (1.8, 2.0E−3, 5.7E−1); developmental protein (1.74, 3.2E−4, 1.2E−2); defense response to pathogen, incompatible interaction (1.71, 4.9E−4, 1.5E−1); golgi stack (1.69, 5.4E−3, 1.1E−1); protein transport (1.69, 9.7E−3, 1.8E−1); ribosomal protein (1.64, 2.7E−5, 1.4E−3); | A % T % G % C % | t 27.70 42.07 12.00 18.21 | t 9.560 50.66 28.68 11.09 | t 11.16 48.98 19.46 20.37 |
| 1345 | transit peptide (5.07, 2.5E−10, 9.1E−8); mitochondrion (5.07, 1.2E−3, 2.9E−2); membrane (4.47, 3.7E−8, 4.6E−6); transport (4.47, 2.2E−6, 1.4E−4); transmembrane (4.47, | A % T % | g 15.76 31.37 | t 25.27 36.05 | t 20.74 49.21 |

TABLE 1-continued

Emerging gene clusters which were identified by the clustering algorithm pertaining *Arabidopsis Thaliana*.
The below clusters are arranged according to declining size. For each cluster, the table
depicts the distribution of nucleotides for each position along the context sequence.

|  |  |  |  |  |  |
|---|---|---|---|---|---|
|  | 2.5E−5, 1.1E−3); plastid (4.05, 1.9E−3, 4.3E−2); amino-acid biosynthesis (2.15, 1.0E−5, 5.4E−4); DNA-directed RNA polymerase activity (2.13, 1.2E−4, 9.3E−2); RNA POLYMERASE (2.13, 4.6E−4, 5.1E−2); PURINE METABOLISM (2.13, 1.9E−2, 5.1E−1); dna-directed rna polymerase (2.13, 2.4E−2, 3.0E−1); PYRIMIDINE METABOLISM (2.13, 2.6E−2, 5.3E−1); ribonucleoprotein (2.03, 2.1E−8, 3.9E−6); ribosomal protein (2.03, 2.8E−8, 4.2E−6); cytosolic ribosome (sensu Eukaryota) (2.03, 2.4E−4, 5.0E−2); structural constituent of ribosome (2.03, 3.5E−3, 6.9E−1); cytosol (2.03, 6.2E−3, 3.6E−1); RIBOSOME (2.03, 4.7E−2, 6.0E−1); nuclear protein (1.84, 5.4E−4, 1.6E−2); transcription (1.84, 1.8E−2, 2.5E−1); dna-binding (1.84, 6.2E−2, 5.2E−1); transcription regulation (1.84, 7.2E−2, 5.5E−1); glycoprotein (1.8, 3.1E−5, 1.3E−3); signal (1.8, 5.5E−3, 1.1E−1); gtp-binding (1.73, 1.8E−5, 8.3E−4); P-loop (1.73, 6.9E−5, 2.7E−3); nucleotide binding (1.73, 1.5E−4, 5.6E−3); GTP binding (1.73, 4.0E−3, 8.3E−2); lipoprotein (1.73, 1.0E−2, 1.6E−1); rna-binding (1.58, 1.8E−4, 6.2E−3); metal-binding (1.49, 2.3E−9, 5.7E−7); zinc (1.49, 1.1E−6, 9.6E−5); zinc-finger (1.49, 6.4E−6, 3.9E−4); | G %<br>C % | 38.43<br>14.42 | 13.75<br>24.90 | 22.52<br>7.509 |
| 751 | transit peptide (6.85, 6.3E−11, 2.3E−8); plastid (6.85, 2.9E−8, 7.0E−6); chloroplast (6.85, 2.3E−7, 4.3E−5); transit peptide: Chloroplast (6.85, 9.2E−4, 5.1E−1); apoplast (3.2, 5.7E−6, 5.9E−4); Germin (3.2, 1.8E−5, 7.0E−2); Cupin 1 (3.2, 2.1E−5, 4.2E−2); Cupin region (3.2, 3.0E−5, 3.9E−2); signal (3.2, 1.4E−4, 1.3E−2); glycoprotein (3.2, 1.6E−4, 1.3E−2); cell wall (3.2, 5.7E−4, 3.2E−2); manganese (3.2, 6.2E−4, 3.2E−2); metal ion-binding site: Manganese (3.2, 2.2E−3, 5.7E−1); response to stimulus (2.96, 2.5E−5, 5.0E−2); response to abiotic stimulus (2.96, 3.5E−5, 3.5E−2); response to chemical stimulus (2.96, 2.9E−3, 6.2E−1); transmembrane (2.11, 4.4E−4, 2.9E−2); membrane (2.11, 1.2E−3, 4.7E−2); EFh (2, 2.1E−3.5, 2E−1); | <br>A %<br>T %<br>G %<br>C % | a<br>60.85<br>14.38<br>9.720<br>15.04 | c<br>26.76<br>5.326<br>32.09<br>35.81 | a<br>85.08<br>3.728<br>4.127<br>7.057 |
| 680 | signal (3.44, 8.0E−6, 5.9E−3); multigene family (3.44, 1.4E−5, 5.0E−3); glycoprotein (3 .44, 7.3E−5, 1.3E−2); oxidoreductase (2.6, 3.3E−5, 8.1E−3); iron (2.6, 7.6E−3, 2.7E−1); membrane (2.55, 1.8E−4, 2.2E−2); transmembrane (2.55, 6.6E−4, 4.7E−2); transit peptide (2.21, 7.8E−4, 5.1E−2); plastid (2.21, 1.2E−3, 6.2E−2); chloroplast (2.21, 1.4E−2, 4.2E−1); systemic acquired resistance (2.04, 8.3E−5, 1.6E−1); | <br>A %<br>T %<br>G %<br>C % | a<br>46.76<br>25.44<br>10.14<br>17.64 | a<br>40.44<br>35.73<br>10.44<br>13.38 | t<br>17.64<br>35.58<br>28.38<br>18.38 |
| 680 | transit peptide (3.84, 3.5E−7, 1.3E−4); plastid (3.84, 2.4E−4, 2.1E−2); chloroplast (3.84, 3.5E−4, 2.8E−2); nuclear protein (3.65, 5.6E−5, 8.2E−3); transcription regulation (3.65, 1.7E−4, 2.1E−2); transcription (3.65, 3.6E−4, 2.6E−2); dna-binding (3.65, 6.8E−4, 4.4E−2); chloroplast (3.65, 5.0E−5, 2.1E−2); plastid (3.65, 7.5E−5, 1.6E−2); calcium (1.69, 1.2E−3, 6.3E−2); EF hand (1.69, 1.6E−2, 4.2E−1); DNA-binding (1.42, 1.8E−4, 1.9E−2) | <br>A %<br>T %<br>G %<br>C % | a<br>34.41<br>32.64<br>17.20<br>15.73 | a<br>48.97<br>11.17<br>23.38<br>16.47 | a<br>68.08<br>10.44<br>10.58<br>10.88 |
| 655 | plastid (, 1.1E−11, 4.8E−9); chloroplast (, 1.2E−11, 2.6E−9); nuclear protein (3.09, 2.1E−4, 1.5E−2); transcription regulation (3.09, 4.0E−4, 2.7E−2); transcription (3.09, 8.4E−4, 5.0E−2); dna-binding (3.09, 6.0E−3, 2.5E−1); transit peptide (1.96, 1.1E−4, 9.8E−3); plastid (1.96, 1.3E−2, 4.5E.1); kinase (1.65, 9.6E−8, 7.0E−5); transferase (1.65, 4.3E−7, 1.6E−4); nucleotide-binding (1.65, 4.5E−6, 1.1E−3); serine/threonine-protein kinase (1.65, 1.1E−5, 1.6E−3); atp-binding (1.65, 2.0E−5, 2.5E−3); auxin signaling pathway (1.46, 1.9E−2, 5.3E−1); zinc-finger (1.09, 7.3E−6, 1.3E−3); zinc (1.09, 8.1E−5, 8.5E−3); metal-binding (1.09, 2.1E−3, 1.1E−1); calcium (0.92, 1.4E−2, 4.5E−1); | <br>A %<br>T %<br>G %<br>C % | t<br>19.38<br>39.23<br>21.22<br>20.15 | t<br>7.022<br>62.29<br>7.175<br>23.51 | t<br>11.45<br>43.66<br>4.274<br>40.61 |
| 618 | response to hormone stimulus (3.85, 1.2E−5, 2.5E−2); response to chemical stimulus (3.85, 1.5E−5, 1.5E−2); response to abiotic stimulus (3.85, 2.4E−5, 1.6E−2); response to endogenous stimulus (3.85, 2.9E−4, 1.4E−1); response to auxin stimulus (3.85, 1.9E−3, 4.8E−1); response to stimulus (3.85, 3.0E−3, 5.8E−1); membrane (3.55, 1.6E−7, 5.9E−5); metalloprotein (0.89, 3.3E−2, 5.7E−1); chromoprotein (0.89, 3.9E−2, 6.0E−1); nuclear protein (0.87, 4.0E−2, 6.0E−1); Membrane (0.62, 5.1E−2, 6.4E−1); rna-binding (0.4, 4.2E−2, 5.9E−1); nucleotide-binding (0.12, 1.7E−2, 4.1E−1); | <br>A %<br>T %<br>G %<br>C % | a<br>35.76<br>29.12<br>21.19<br>13.91 | a<br>53.55<br>21.03<br>2.427<br>22.97 | t<br>17.63<br>63.26<br>6.634<br>12.45 |

TABLE 1-continued

Emerging gene clusters which were identified by the clustering algorithm pertaining *Arabidopsis Thaliana*. The below clusters are arranged according to declining size. For each cluster, the table depicts the distribution of nucleotides for each position along the context sequence.

| | | | | | |
|---|---|---|---|---|---|
| 462 | nuclear protein (3.2, 2.1E−7, 1.5E−4); transcription (3.2, 3.3E−5, 1.2E−2); transcription regulation (3.2, 4.8E−5, 1.2E−2); Transcription factor, K-box (3.2, 2.0E−4, 5.5E−1); domain: K-box (3.2, 2.4E−4, 8.8E−2); domain: MADS-box (3.2, 2.4E−4, 8.8E−2); coiled coil (3.2, 4.0E−4, 4.1E−2); activator (3.2, 6.8E−4, 5.4E−2); dna-binding (3.2, 9.7E−4, 6.9E−2); flowering (3.2, 1.8E−2, 5.9E−1); developmental protein (3.2, 2.2E−2, 6.1E−1); differentiation (3.2, 2.8E−2, 6.8E−1); transport (1.9, 5.7E−5, 8.4E−3); membrane (1.9, 1.6E−2, 5.7E−1); zinc (0.48, 1.4E−2, 5.5E−1); ion transport (0.42, 2.1E−2, 6.3E−1); transferase (0.38, 2.6E−4, 3.1E−2); | A % T % G % C % | g 11.47 8.225 74.89 5.411 | a 76.19 3.030 15.15 5.627 | g 15.36 7.792 74.89 1.948 |
| 457 | response to abiotic stimulus (2.11, 1.1E−3, 6.9E−1); response to chemical stimulus (2.11, 1.7E−3, 6.7E−1); transit peptide (2.02, 1.0E−4, 1.9E−2); chloroplast (2.02, 1.1E−2, 3.4E−1); plastid (2.02, 1.2E−2, 3.5E−1); photosynthesis (2.02, 1.4E−2, 3.7E−1); thylakoid (2.02, 1.8E−2, 4.1E−1); zymogen (1.95, 9.0E−6, 6.6E−3); propeptide: Activation peptide (1.95, 8.1E−4, 4.6E−1); thiol protease (1.95, 2.4E−3, 1.2E−1); protease (1.95, 2.6E−3, 1.2E−1); signal (1.95, 6.0E−3, 2.2E−1); nuclear protein (1.87, 3.8E−4, 3.9E−2); activator (1.87, 1.1E−3, 6.6E−2); dna-binding (1.87, 1.6E−2, 3.9E−1); transcription (1.87, 2.9E−2, 5.5E−1); transcription regulation (1.87, 3.5E−2, 6.0E−1); oxidoreductase (1.49, 2.1E−5, 5.1E−3); monooxygenase (1.49, 1.9E−4, 2.8E−2); iron (1.49, 8.7E−4, 5.7E−2); Membrane (1.49, 4.2E−3, 1.8E−1); | A % T % G % C % | g 10.50 5.032 67.83 16.63 | a 82.93 1.969 5.908 9.190 | a 96.93 0.656 1.312 1.094 |
| 375 | nuclear protein (1.48, 3.9E−4, 9.1E−2); response to light stimulus (1.44, 3.2E−4, 4.8E−1); response to radiation (1.44, 3.5E−4, 3.0E−1); flavoprotein (1.33, 1.9E−2, 5.8E−1); oxidoreductase (1.19, 4.0E−3, 3.1E−1); iron (1.19, 1.8E−2, 6.1E−1); transit peptide (1.07, 6.9E−3, 4.0E−1); signal (1.06, 1.4E−3, 1.9E−1); iron (0.89, 1.8E−2, 6.1E−1); metal-binding (0.82, 9.0E−5, 6.4E−2); zinc-finger (0.82, 1.7E−3, 1.9E−1); zinc (0.82, 2.3E−3, 2.1E−1); ribonucleoprotein (0.69, 1.5E−4, 5.5E−2); ribosomal protein (0.69, 8.3E−4, 1.4E−1); protease (0.62, 1.7E−2, 6.2E−1); kinase (0.32, 7.0E−3, 3.7E−1); transferase (0.32, 1.8E−2, 6.0E−1); | A % T % G % C % | a 48.26 16 19.73 16 | a 29.86 22.66 21.06 26.4 | a 55.46 3.733 5.333 35.46 |
| 327 | nuclear protein (1.74, 1.0E−3, 3.2E−1); transcription (1.74, 4.8E−3, 5.1E−1); dna-binding (1.74, 5.5E−3, 4.9E−1); transport (1.48, 7.6E−4, 4.3E−1); gtp-binding (1.28, 3.0E−3, 5.2E−1); | A % T % G % C % | a 81.34 9.785 3.669 5.198 | a 58.40 0.917 30.58 10.09 | g 11.62 1.529 84.40 2.446 |
| 306 | transit peptide (1.44, 9.2E−3, 6.2E−1); transcription regulation (1.43, 8.5E−3, 6.5E−1); dna-binding (0.71, 8.6E−5, 6.1E−2); transcription regulation (0.71, 8.5E−3, 6.5E−1); transcription regulation (0.69, 8.5E−3, 6.5E−1); | A % T % G % C % | t 0 59.80 4.248 35.94 | t 30.39 40.52 15.68 13.39 | g 11.11 15.03 45.75 28.10 |
| 305 | multigene family (5.69, 1.4E−9, 1.0E−6); signal (5.69, 5.1E−7, 1.9E−4); toxin (3.16, 8.9E−5, 1.3E−2); plant toxin (3.16, 8.9E−5, 1.3E−2); plant defense (3.16, 3.0E−3, 1.7E−1); membrane (2.9, 5.1E−5, 9.3E−3); transmembrane (2.9, 2.4E−4, 2.5E−2); calcium (1.69, 3.3E−4, 3.0E−2); iron (1.69, 5.9E−4, 4.6E−2); oxidoreductase (1.69, 1.1E−3, 7.6E−2); metal-binding (1.69, 2.3E−3, 1.4E−1); hydrogen peroxide (1.69, 3.1E−3, 1.6E−1); | A % T % G % C % | a 72.78 5.245 9.180 12.78 | a 66.55 1.639 15.40 16.39 | t 27.86 36.06 11.80 24.26 |
| 305 | cytoplasm (1.72, 1.3E−4, 5.5E−2); chloroplast (1.72, 1.0E−2, 5.9E−1); nuclear protein (1.31, 1.0E−2, 5.7E−1); transmembrane (1.27, 2.8E−3, 2.6E−1); ribosomal protein (1.05, 4.8E−4, 8.4E−2); ribonucleoprotein (1.05, 7.4E−4, 1.0E−1); cytosolic ribosome (sensu Eukaryota) (1.05, 7.7E−3, 6.7E−1); eukaryotic 43S preinitiation complex (1.05, 9.2E−3, 6.3E−1); metal-binding (1.01, 1.5E−2, 6.6E−1); transmembrane (0.89, 2.8E−3, 2.6E−1); | A % T % G % C % | g 26.22 21.96 27.86 23.93 | t 30.16 32.78 12.45 24.59 | a 47.54 28.52 5.573 18.36 |
| 302 | chloroplast (5.22, 5.5E−9, 2.4E−6); plastid (5.22, 8.4E−9, 1.8E−6); cytoplasm (5.22, 9.7E−9, 1.4E−6); membrane-bound organelle (5.22, 1.4E−5, 1.5E−3); intracellular membrane-bound organelle (5.22, 2.0E−5, 1.7E−3); organelle (5.22, 6.8E−5, 4.9E−3); | A % T % G % C % | t 6.622 70.52 8.609 14.23 | c 1.986 5.960 4.635 87.41 | t 22.51 64.90 7.947 4.635 |
| 245 | plastid (1.18, 5.2E−3, 6.8E−1); cytoplasm (1.18, 5.9E−3, 5.7E−1); | A % T % G % C % | t 11.42 66.12 8.571 13.87 | t 2.857 91.02 3.673 2.448 | t 19.59 49.38 13.06 17.95 |

TABLE 1-continued

Emerging gene clusters which were identified by the clustering algorithm pertaining *Arabidopsis Thaliana*.
The below clusters are arranged according to declining size. For each cluster, the table
depicts the distribution of nucleotides for each position along the context sequence.

| | | | t | c | t |
|---|---|---|---|---|---|
| 242 | chloroplast (2.61, 3.6E−6, 1.6E−3); plastid (2.61, 4.8E−6, 1.0E−3); cytoplasm (2.61, 1.5E−3, 2.0E−1); membrane-bound organelle (2.61, 6.5E−3, 5.1E−1); intracellular membrane-bound organelle (2.61, 9.0E−3, 5.4E−1); transcription (2.01, 2.1E−3, 4.0E−1); transcription regulation (2.01, 2.6E−3, 3.8E−1); nuclear protein (2.01, 1.7E−2, 6.8E−1); gpi-anchor (1.76, 2.7E−4, 1.8E−1); lipoprotein (1.76, 2.1E−3, 5.3E−1); glycoprotein (1.76, 5.6E−3, 4.9E−1); membrane (1.76, 5.7E−3, 4.5E−1); signal (1.76, 8.5E−3, 4.6E−1); anchored to membrane (1.76, 1.4E−2, 6.3E−1); nuclease (1.05, 8.0E−3, 4.8E−1); membrane (0.93, 5.7E−3, 4.5E−1); | A % T % G % C % | 12.80 55.37 15.28 16.52 | 2.066 18.59 5.785 73.55 | 17.76 78.92 0.826 2.479 |
| | | A % T % G % C % | 4.366 93.88 0 1.746 | 2.620 3.930 5.240 88.20 | 5.240 83.40 0.873 10.48 |
| 219 | membrane (2.87, 6.1E−7, 4.5E−4); transmembrane (2.87, 1.9E−3, 1.8E−1); transport (2.87, 5.4E−3, 3.9E−1); signal (2.27, 3.2E−6, 7.8E−4); glycoprotein (2.27, 4.9E−4, 6.9E−2); cell wall (sensu Magnoliophyta) (1.5, 2.0E−3, 2.5E−1); cell wall (1.5, 1.0E−2, 6.7E−1); external encapsulating structure (1.5, 1.1E−2, 6.2E−1); metal-binding (0.97, 1.1E−3, 1.2E−1); transport (0.68, 5.4E−3, 3.9E−1); coiled coil (0.21, 1.4E−2, 6.8E−1); | A % T % G % C % | a 51.59 10.50 17.35 20.54 | a 94.06 1.369 4.109 0.456 | a 51.59 10.50 23.28 14.61 |
| 196 | transcription (2.65, 7.7E−4, 4.3E−1); transcription regulation (2.65, 9.4E−4, 2.9E−1); nuclear protein (2.65, 2.4E−3, 4.4E−1); plastid (1.56, 1.0E−2, 6.5E−1); | A % T % G % C % | c 18.36 7.653 29.59 44.38 | a 53.57 36.22 5.102 5.102 | c 21.42 23.97 26.02 28.57 |
| 187 | membrane (1.5, 1.6E−3, 6.9E−1); transmembrane (1.5, 7.5E−3, 6.7E−1); chaperone (1.23, 6.3E−3, 6.9E−1); | A % T % G % C % | g 35.82 1.604 50.26 12.29 | a 44.91 43.85 4.812 6.417 | t 10.16 73.26 1.069 15.50 |
| 176 | transit peptide (2.61, 1.9E−5, 1.4E−2); lyase (2.61, 1.4E−4, 4.9E−2); Ribulose bisphosphate carboxylase, small chain (2.61, 1.6E−4, 4.7E−1); carbon dioxide fixation (2.61, 4.8E−4, 1.1E−1); photorespiration (2.61, 6.3E−4, 1.1E−1); photosynthesis (2.61, 1.2E−3, 1.6E−1); chloroplast (2.61, 1.7E−3, 1.8E−1); GLYOXYLATE AND DICARBOXYLATE METABOLISM (2.61, 2.9E−3, 2.8E−1); multigene family (2.61, 4.1E−3, 3.1E−1); plastid (2.61, 4.6E−3, 3.1E−1); cytoplasm (1.35, 1.1E−3, 1.5E−1); | A % T % G % C % | g 14.20 2.840 81.81 1.136 | a 88.06 1.704 7.954 2.272 | a 92.61 0.568 6.25 0.568 |
| 165 | nuclear protein (1.99, 7.5E−4, 4.2E−1); chloroplast (1.58, 4.7E−3, 6.8E−1); nuclear protein (0.59, 7.5E−4, 4.2E−1); | A % T % G % C % | c 9.090 24.84 6.060 60 | t 4.848 90.30 3.636 1.212 | t 4.242 89.69 1.818 4.242 |
| 162 | metal-binding (1.1, 6.8E−4, 3.9E−1); zinc (0.62, 2.5E−3, 6.0E−1); kinase (0.61, 4.4E−3, 6.6E−1); | A % T % G % C % | t 31.48 43.20 12.96 12.34 | g 17.90 24.69 48.14 9.259 | a 69.75 10.49 15.43 4.320 |
| 161 | dna-binding (2.13, 1.2E−3, 5.7E−1); nuclear protein (2.13, 2.0E−3, 5.1E−1); | A % T % G % C % | t 19.87 73.29 3.105 3.726 | t 26.08 45.96 3.105 24.84 | a 50.93 32.91 10.55 5.590 |
| 160 | membrane (1.72, 3.9E−4, 2.5E−1); plastid (0.77, 2.6E−3, 6.7E−1); chloroplast (0.77, 4.7E−3, 6.4E−1); | A % T % G % C % | t 11.87 78.75 6.25 3.125 | c 11.25 23.75 6.25 58.75 | t 0.625 96.87 1.875 0.625 |
| 157 | chloroplast (2.62, 2.0E−4, 8.3E−2); plastid (2.62, 2.4E−4, 5.1E−2); membrane-bound organelle (2.62, 7.8E−4, 1.1E−1); intracellular membrane-bound organelle (2.62, 1.3E−3, 1.3E−1); organelle (2.62, 2.0E−3, 1.6E−1); cytoplasm (2.62, 2.7E−3, 1.8E−1); intracellular organelle (2.62, 3.3E−3, 1.8E−1); intracellular (2.62, 7.6E−3, 3.4E−1); | A % T % G % C % | a 64.96 12.73 8.917 13.37 | a 59.23 5.732 28.66 6.369 | g 31.84 6.369 36.30 25.47 |
| 155 | ubiquitin-protein ligase activity (1.21, 1.2E−3, 6.4E−1); | A % T % G % C % | g 18.06 25.80 38.06 18.06 | a 35.48 29.03 21.93 13.54 | t 3.225 89.67 6.451 0.645 |
| 152 | transmembrane (1.61, 3.1E−3, 5.3E−1); glycosyltransferase (1.11, 5.3E−3, 6.3E−1); metal-binding (0.47, 8.1E−4, 4.5E−1); | A % T % G % C % | t 3.947 94.07 1.973 0 | t 15.78 42.10 3.289 38.81 | g 15.13 3.289 46.71 34.86 |

TABLE 1-continued

Emerging gene clusters which were identified by the clustering algorithm pertaining *Arabidopsis Thaliana*.
The below clusters are arranged according to declining size. For each cluster, the table
depicts the distribution of nucleotides for each position along the context sequence.

| | | | | | |
|---|---|---|---|---|---|
| 150 | membrane (1.9, 1.3E−3, 6.1E−1); membrane (1.34, 1.3E−3, 6.1E−1); nucleotide-binding (0.44, 1.9E−3, 5.1E−1); | | t | t | a |
| | | A % | 2 | 9.333 | 35.33 |
| | | T % | 97.33 | 48.66 | 27.33 |
| | | G % | 0.666 | 18.66 | 27.33 |
| | | C % | 0 | 23.33 | 10 |
| 139 | ribosomal protein (2.22, 9.5E−6, 7.0E−3); intracellular non-membrane-bound organelle (2.22, 1.1E−5, 4.6E−3); non-membrane-bound organelle (2.22, 1.1E−5, 4.6E−3); ribonucleoprotein complex (2.22, 1.1E−5, 1.6E−3); ribosome (2.22, 1.1E−4, 1.2E−2); structural constituent of ribosome (2.22, 1.5E−4, 2.2E−1); structural molecule activity (2.22, 2.2E−4, 1.7E−1); ribonucleoprotein (2.22, 2.9E−4, 1.0E−1); ribosome (2.22, 6.0E−3, 6.7E−1); RIBOSOME (2.22, 6.7E−3, 5.3E−1); ribosomal protein (2.21, 9.5E−6, 7.0E−3); RIBOSOME (2.21, 6.7E−3, 5.3E−1); | | c | c | g |
| | | A % | 15.10 | 1.438 | 0 |
| | | T % | 26.61 | 0 | 2.877 |
| | | G % | 2.158 | 0 | 96.40 |
| | | C % | 56.11 | 98.56 | 0.719 |
| 131 | threonine protease (2.08, 7.9E−4, 4.4E−1); | | a | a | t |
| | | A % | 70.22 | 96.18 | 35.11 |
| | | T % | 6.870 | 1.526 | 45.03 |
| | | G % | 17.55 | 1.526 | 12.97 |
| | | C % | 5.343 | 0.763 | 6.870 |
| 120 | wd repeat (2.32, 1.9E−4, 1.3E−1); WD40 (2.32, 2.1E−3, 5.2E−1); transferase (0.68, 1.9E−3, 5.0E−1); | | a | t | c |
| | | A % | 46.66 | 11.66 | 10.83 |
| | | T % | 14.16 | 37.5 | 18.33 |
| | | G % | 34.16 | 14.16 | 17.5 |
| | | C % | 5 | 36.66 | 53.33 |
| 117 | metal-binding (1.95, 5.6E−4, 3.4E−1); nuclear protein (1.46, 1.7E−3, 4.6E−1); signal (1.15, 2.3E−3, 4.3E−1); | | a | t | c |
| | | A % | 66.66 | 5.128 | 21.36 |
| | | T % | 17.09 | 65.81 | 4.273 |
| | | G % | 6.837 | 21.36 | 0.854 |
| | | C % | 9.401 | 7.692 | 73.50 |
| 109 | intracellular (1.56, 4.3E−3, 6.1E−1); | | g | c | g |
| | | A % | 27.52 | 14.67 | 20.18 |
| | | T % | 21.10 | 19.26 | 15.59 |
| | | G % | 37.61 | 5.504 | 64.22 |
| | | C % | 13.76 | 60.55 | 0 |
| 108 | chloroplast (4.2, 6.9E−6, 3.0E−3); plastid (4.2, 8.5E−6, 1.8E−3); intracellular membrane-bound organelle (4.2, 3.3E−5, 4.8E−3); membrane-bound organelle (4.2, 3.8E−5, 4.1E−3); intracellular organelle (4.2, 6.5E−5, 5.6E−3); intracellular (4.2, 6.7E−5, 4.8E−3); organelle (4.2, 7.4E−5, 4.5E−3); cytoplasm (4.2, 2.0E−4, 1.1E−2); cell (4.2, 3.2E−3, 1.4E−1); OXIDATIVE PHOSPHORYLATION (0.79, 6.7E−3, 5.3E−1); | | t | c | t |
| | | A % | 4.629 | 1.851 | 12.96 |
| | | T % | 71.29 | 14.81 | 62.03 |
| | | G % | 20.37 | 15.74 | 22.22 |
| | | C % | 3.703 | 67.59 | 2.777 |
| 104 | response to abiotic stimulus (3.87, 2.9E−6, 6.0E−3); response to stimulus (3.87, 6.4E−5, 6.3E−2); | | t | c | t |
| | | A % | 5.769 | 4.807 | 36.53 |
| | | T % | 83.65 | 3.846 | 40.38 |
| | | G % | 6.730 | 2.884 | 22.11 |
| | | C % | 3.846 | 88.46 | 0.961 |
| 100 | transit peptide (1.65, 2.9E−3, 4.2E−1); metal-binding (1.43, 6.7E−3, 6.2E−1); ribonucleoprotein (0.96, 7.5E−4, 4.2E−1); ribosomal protein (0.96, 1.9E−3, 5.1E−1); metal-binding (0.44, 6.7E−3, 6.2E−1); | | t | c | t |
| | | A % | 19 | 3 | 8 |
| | | T % | 42 | 7 | 90 |
| | | G % | 31 | 5 | 0 |
| | | C % | 8 | 85 | 2 |
| 93 | multigene family (3.38, 1.7E−6, 1.3E−3); calmodulin-binding (3.38, 1.1E−5, 3.9E−3); membrane (3.38, 7.5E−4, 8.8E−2); transmembrane (3.38, 7.0E−3, 4.7E−1); zinc (2.79, 2.9E−4, 5.2E−2); alternative splicing (2.79, 7.3E−4, 1.0E−1); metal-binding (1.19, 8.2E−5, 2.0E−2); zinc (1.19, 2.9E−4, 5.2E−2); zinc-finger (1.19, 1.1E−3, 1.1E−1); | | g | t | t |
| | | A % | 17.20 | 16.12 | 0 |
| | | T % | 17.20 | 54.83 | 98.92 |
| | | G % | 50.53 | 25.80 | 0 |
| | | C % | 15.05 | 3.225 | 1.075 |
| 85 | intracellular membrane-bound organelle (3.4, 5.0E−5, 2.1E−2); membrane-bound organelle (3.4, 5.6E−5, 1.2E−2); cytoplasm (3.4, 2.0E−4, 2.8E−2); intracellular organelle (3.4, 2.0E−4, 2.1E−2); organelle (3.4, 2.2E−4, 1.9E−2); intracellular (3.4, 1.8E−3, 1.2E−2); cytoplasm (2.65, 2.0E−4, 2.8E−2); chloroplast (2.65, 7.3E−3, 3.3E−1); plastid (2.65, 8.0E−3, 3.2E−1); TIR (1.04, 6.1E−3, 6.6E−1); | | t | c | t |
| | | A % | 4.705 | 3.529 | 20 |
| | | T % | 91.76 | 2.352 | 77.64 |
| | | G % | 0 | 1.176 | 2.352 |
| | | C % | 3.529 | 92.94 | 0 |
| 81 | lipid biosynthesis (1.91, 5.5E−4, 6.7E−1); | | a | a | a |
| | | A % | 44.44 | 75.30 | 95.06 |
| | | T % | 20.98 | 20.98 | 1.234 |
| | | G % | 30.86 | 3.703 | 3.703 |
| | | C % | 3.703 | 0 | 0 |
| 67 | zinc-finger (1.22, 9.0E−4, 4.8E−1); zinc (1.22, 1.8E−3, 4.9E−1); | | c | a | t |
| | | A % | 22.38 | 52.23 | 13.43 |
| | | T % | 16.41 | 38.80 | 85.07 |
| | | G % | 26.86 | 8.955 | 1.492 |
| | | C % | 34.32 | 0 | 0 |

TABLE 1-continued

Emerging gene clusters which were identified by the clustering algorithm pertaining *Arabidopsis Thaliana*.
The below clusters are arranged according to declining size. For each cluster, the table
depicts the distribution of nucleotides for each position along the context sequence.

| # | Description | | c | a | t |
|---|---|---|---|---|---|
| 67 | envelope (1.09, 4.6E−3, 6.4E−1); | A % | 44.77 | 71.64 | 7.462 |
|   |   | T % | 4.477 | 17.91 | 88.05 |
|   |   | G % | 2.985 | 4.477 | 1.492 |
|   |   | C % | 47.76 | 5.970 | 2.985 |
| 61 | TERPENOID BIOSYNTHESIS (2.15, 3.9E−3, 3.6E−1); | | c | g | a |
|   | BIOSYNTHESIS OF STEROIDS (2.15, 1.5E−2, 5.8E−1); | A % | 8.196 | 4.918 | 59.01 |
|   |   | T % | 18.03 | 6.557 | 34.42 |
|   |   | G % | 22.95 | 70.49 | 4.918 |
|   |   | C % | 50.81 | 18.03 | 1.639 |
| 54 | RNA POLYMERASE (2.11, 1.9E−3, 1.9E−1); | | t | a | g |
|   | PYRIMIDINE METABOLISM (2.11, 1.3E−2, 5.3E−1); | A % | 1.851 | 55.55 | 14.81 |
|   | PURINE METABOLISM (2.11, 1.8E−2, 5.0E−1); | T % | 79.62 | 40.74 | 3.703 |
|   |   | G % | 16.66 | 1.851 | 81.48 |
|   |   | C % | 1.851 | 1.851 | 0 |
| 52 | ribonucleoprotein (0.95, 8.9E−4, 2.8E−1); | | t | c | t |
|   |   | A % | 15.38 | 0 | 5.769 |
|   |   | T % | 59.61 | 0 | 67.30 |
|   |   | G % | 13.46 | 0 | 3.846 |
|   |   | C % | 11.53 | 100 | 23.07 |
| 47 | transport (1.34, 2.0E−4, 1.4E−1); | | g | a | a |
|   |   | A % | 0 | 89.36 | 87.23 |
|   |   | T % | 0 | 0 | 0 |
|   |   | G % | 100 | 2.127 | 12.76 |
|   |   | C % | 0 | 8.510 | 0 |
| 46 | cell (1.99, 5.3E−3, 6.9E−1); plastid (1.99, 5.6E−3, 5.6E−1); | | t | c | g |
|   | intracellular organelle (1.99, 9.8E−3, 4.6E−1); organelle | A % | 23.91 | 8.695 | 8.695 |
|   | (1.99, 1.0E−2, 4.3E−1); intracellular (1.99, 1.1E−2, 4.0E−1); | T % | 41.30 | 10.86 | 10.86 |
|   | intracellular membrane-bound organelle (1.99, 1.5E−2, | G % | 15.21 | 2.173 | 67.39 |
|   | 4.8E−1); membrane-bound organelle (1.99, 1.5E−2, | C % | 19.56 | 78.26 | 13.04 |
|   | 4.6E−1); cytoplasm (1.99, 3.3E−2, 6.7E−1); membrane-enclosed lumen (1.37, 5.8E−3, 3.9E−1); organelle lumen (1.37, 5.8E−3, 3.9E−1); nucleolus (1.37, 9.4E−3, 4.9E−1); nuclear lumen (1.37, 2.6E−2, 6.1E−1); | | | | |
| 43 | heat shock (2.56, 1.4E−3, 4.0E−1); | | t | a | a |
|   |   | A % | 4.651 | 90.69 | 65.11 |
|   |   | T % | 53.48 | 0 | 6.976 |
|   |   | G % | 13.95 | 4.651 | 23.25 |
|   |   | C % | 27.90 | 4.651 | 4.651 |
| 43 | eukaryotic 43S preinitiation complex (1.5, 2.9E−5, 1.3E−2); | | t | t | t |
|   | cytosolic small ribosomal subunit (sensu Eukaryota) | A % | 4.651 | 0 | 0 |
|   | (1.5, 1.0E−3, 1.4E−1); eukaryotic 48S initiation complex | T % | 81.39 | 58.13 | 100 |
|   | (1.5, 1.0E−3, 1.4E−1); protein complex (1.5, 2.0E−3, 1.9E−1); | G % | 4.651 | 2.325 | 0 |
|   | small ribosomal subunit (1.5, 3.1E−3, 2.3E−1); | C % | 9.302 | 39.53 | 0 |
|   | cytosolic ribosome (sensu Eukaryota) (1.5, 5.2E−3, 3.1E−1); | | | | |
| 42 | disulfide bond (1.35, 1.5E−3, 6.9E−1); | | g | a | g |
|   |   | A % | 2.380 | 88.09 | 11.90 |
|   |   | T % | 21.42 | 4.761 | 0 |
|   |   | G % | 66.66 | 2.380 | 80.95 |
|   |   | C % | 9.523 | 4.761 | 7.142 |
| 42 | transcription regulation (1.4, 4.2E−3, 6.5E−1); nuclear | | a | a | a |
|   | protein (1.4, 5.5E−3, 6.4E−1); metal-binding (1.4, 6.5E−3, | A % | 95.23 | 38.09 | 88.09 |
|   | 6.2E−1); nuclear protein (0.47, 5.5E−3, 6.4E−1); | T % | 2.380 | 14.28 | 7.142 |
|   |   | G % | 0 | 26.19 | 4.761 |
|   |   | C % | 2.380 | 21.42 | 0 |
| 40 | atp-binding (1.01, 1.5E−3, 6.6E−1); nucleotide-binding | | gc | t | c |
|   | (1.01, 2.2E−3, 5.5E−1); | A % | 15 | 0 | 10 |
|   |   | T % | 10 | 95 | 0 |
|   |   | G % | 37.5 | 0 | 2.5 |
|   |   | C % | 37.5 | 5 | 87.5 |
| 36 | cytoplasm (2.29, 3.6E−4, 1.4E−1); mitochondrion (2.29, | | tg | a | c |
|   | 5.2E−4, 1.1E−1); intracellular membrane-bound organelle | A % | 0 | 72.22 | 0 |
|   | (2.29, 4.7E−3, 4.9E−1); membrane-bound organelle (2.29, | T % | 38.88 | 0 | 0 |
|   | 4.9E−3, 4.1E−1); intracellular organelle (2.29, 8.7E−3, | G % | 38.88 | 27.77 | 0 |
|   | 4.7E−1); organelle (2.29, 9.1E−3, 4.3E−1); intracellular | C % | 22.22 | 0 | 100 |
|   | (2.29, 2.3E−2, 6.1E−1); ribosome (0.87, 7.8E−3, 4.9E−1); non-membrane-bound organelle (0.87, 1.1E−2, 4.1E−1); intracellular non-membrane-bound organelle (0.87, 1.1E−2, 4.1E−1); ribonucleoprotein complex (0.87, 1.9E−2, 5.6E−1); | | | | |
| 35 | chloroplast stroma (1.04, 1.1E−3, 3.9E−1); plastid stroma | | g | ag | t |
|   | (1.04, 2.1E−3, 3.7E−1); | A % | 40 | 40 | 11.42 |
|   |   | T % | 2.857 | 2.857 | 88.57 |
|   |   | G % | 48.57 | 40 | 0 |
|   |   | C % | 8.571 | 17.14 | 0 |
| 35 | membrane (1.78, 4.1E−6, 3.0E−3); transmembrane (1.78, | | g | a | c |
|   | 4.9E−5, 1.8E−2); transmembrane region (1.78, 7.3E−4, | A % | 11.42 | 34.28 | 0 |

TABLE 1-continued

Emerging gene clusters which were identified by the clustering algorithm pertaining *Arabidopsis Thaliana*.
The below clusters are arranged according to declining size. For each cluster, the table
depicts the distribution of nucleotides for each position along the context sequence.

|  |  |  |  |  |  |
|---|---|---|---|---|---|
|  | 4.3E−1); ubl conjugation pathway (1.78, 1.4E−3, 2.8E−1); metal-binding (1.78, 2.0E−3, 3.0E−1); zinc (1.78, 5.1E−3, 5.2E−1); | T % | 28.57 | 31.42 | 0 |
|  |  | G % | 34.28 | 22.85 | 0 |
|  |  | C % | 25.71 | 11.42 | 100 |
| 34 | transcription factor activity (1.03, 2.5E−4, 3.3E−1); transcription regulator activity (1.03, 7.7E−4, 4.7E−1); |  | t | t | c |
|  |  | A % | 0 | 0 | 0 |
|  |  | T % | 94.11 | 94.11 | 5.882 |
|  |  | G % | 0 | 5.882 | 2.941 |
|  |  | C % | 5.882 | 0 | 91.17 |
| 32 | prenylation (2.78, 3.3E−5, 2.4E−2); lipid moiety-binding region: S-geranylgeranyl cysteine (2.78, 1.0E−4, 7.5E−2); lipoprotein (2.78, 4.9E−4, 1.6E−1); nucleotide phosphate-binding region: GTP (2.78, 1.4E−3, 4.1E−1); gtp-binding (2.78, 2.0E−3, 3.9E−1); membrane (2.78, 4.7E−3, 5.8E−1); |  | a | c | g |
|  |  | A % | 62.5 | 6.25 | 3.125 |
|  |  | T % | 0 | 0 | 9.375 |
|  |  | G % | 34.37 | 0 | 84.37 |
|  |  | C % | 3.125 | 93.75 | 3.125 |
| 32 | membrane (2.21, 8.0E−6, 5.9E−3); transmembrane (2.21, 9.5E−5, 3.4E−2); metal-binding (2.21, 2.6E−4, 6.2E−2); zinc (2.21, 5.2E−4, 9.1E−2); transmembrane region (2.21, 7.3E−4, 4.3E−1); ubl conjugation pathway (2.21, 1.7E−3, 2.2E−1); zinc-finger (2.21, 4.5E−3, 4.2E−1); |  | g | ag | c |
|  |  | A % | 12.5 | 37.5 | 0 |
|  |  | T % | 25 | 12.5 | 0 |
|  |  | G % | 56.25 | 37.5 | 0 |
|  |  | C % | 6.25 | 12.5 | 100 |
| 28 | SF016605: *Arabidopsis thaliana* transcription factor DREB1B (2.02, 2.8E−5, 9.8E−2); DNA-binding region: AP2/ERF (2.02, 9.4E−5, 7.0E−2); transcription factor (2.02, 2.7E−4, 1.8E−1); activator (2.02, 8.7E−4, 2.7E−1); nuclear protein (2.02, 1.6E−3, 3.3E−1); |  | c | t | c |
|  |  | A % | 10.71 | 0 | 0 |
|  |  | T % | 39.28 | 85.71 | 28.57 |
|  |  | G % | 7.142 | 14.28 | 14.28 |
|  |  | C % | 42.85 | 0 | 57.14 |
| 28 | nuclear protein (3.28, 8.0E−5, 5.7E−2); transcription (3.28, 2.0E−4, 7.1E−2); transcription regulation (3.28, 2.2E−4, 5.3E−2); |  | t | t | t |
|  |  | A % | 0 | 0 | 3.571 |
|  |  | T % | 53.57 | 100 | 96.42 |
|  |  | G % | 17.85 | 0 | 0 |
|  |  | C % | 28.57 | 0 | 0 |
| 27 | response to water deprivation (1.91, 3.3E−4, 4.9E−1); response to water (1.91, 5.0E−4, 4.0E−1); |  | c | t | t |
|  |  | A % | 0 | 0 | 14.81 |
|  |  | T % | 0 | 96.29 | 51.85 |
|  |  | G % | 7.407 | 3.703 | 29.62 |
|  |  | C % | 92.59 | 0 | 3.703 |
| 26 | response to chemical stimulus (2.9, 3.0E−4, 4.6E−1); response to hormone stimulus (2.9, 6.2E−4, 4.7E−1); response to abiotic stimulus (2.9, 9.7E−4, 4.8E−1); |  | a | a | c |
|  |  | A % | 84.61 | 80.76 | 15.38 |
|  |  | T % | 11.53 | 19.23 | 3.846 |
|  |  | G % | 3.846 | 0 | 19.23 |
|  |  | C % | 0 | 0 | 61.53 |
| 26 | nucleotide-binding (1.12, 2.2E−3, 5.5E−1); transferase (1.12, 2.7E−3, 4.9E−1); |  | t | t | g |
|  |  | A % | 0 | 0 | 0 |
|  |  | T % | 92.30 | 88.46 | 19.23 |
|  |  | G % | 7.692 | 0 | 69.23 |
|  |  | C % | 0 | 11.53 | 11.53 |
| 25 | ubiquitin conjugating enzyme activity (1.05, 2.4E−4, 3.3E−1); small protein conjugating enzyme activity (1.05, 2.8E−4, 2.0E−1); UBCc (1.05, 1.7E−3, 4.5E−1); |  | c | t | c |
|  |  | A % | 0 | 4 | 4 |
|  |  | T % | 32 | 92 | 0 |
|  |  | G % | 8 | 4 | 0 |
|  |  | C % | 60 | 0 | 96 |
| 25 | nuclear protein (2.56, 1.0E−3, 5.2E−1); transcription regulation (2.56, 4.7E−3, 6.9E−1); |  | t | t | t |
|  |  | A % | 0 | 0 | 4 |
|  |  | T % | 56 | 100 | 96 |
|  |  | G % | 20 | 0 | 0 |
|  |  | C % | 24 | 0 | 0 |
| 25 | Protein phosphatase 2C (2, 2.3E−4, 6.0E−1); PP2Cc (2, 3.2E−3, 6.8E−1); |  | a | g | a |
|  |  | A % | 96 | 16 | 100 |
|  |  | T % | 0 | 0 | 0 |
|  |  | G % | 0 | 80 | 0 |
|  |  | C % | 4 | 4 | 0 |
| 24 | pyridoxal phosphate (3.68, 9.5E−7, 7.0E−4); nicotianamine synthase activity (3.68, 1.7E−6, 2.9E−3); Nicotianamine synthase (3.68, 2.0E−6, 8.1E−3); multigene family (3.68, 1.1E−3, 3.4E−1); transferase activity, transferring alkyl or aryl (other than methyl) groups (3.68, 1.4E−3, 6.8E−1); |  | t | g | t |
|  |  | A % | 20.83 | 0 | 0 |
|  |  | T % | 45.83 | 16.66 | 100 |
|  |  | G % | 0 | 62.5 | 0 |
|  |  | C % | 33.33 | 20.83 | 0 |

| Size of Cluster (number of context sequences) | Distribution of nucleotides per position along the context sequence (%) | | | | | |
|---|---|---|---|---|---|---|
|  | −6 | −5 | −4 | −3 | −2 | −1 |
| 1613 | a | a | a | a | a | a |
|  | 61.50 | 74.27 | 73.03 | 89.77 | 79.54 | 71.48 |
|  | 3.967 | 4.091 | 1.735 | 1.735 | 2.603 | 7.873 |
|  | 28.58 | 6.943 | 23.49 | 7.501 | 6.137 | 15.93 |
|  | 5.951 | 14.69 | 1.735 | 0.991 | 11.71 | 4.711 |

TABLE 1-continued

Emerging gene clusters which were identified by the clustering algorithm pertaining *Arabidopsis Thaliana*.
The below clusters are arranged according to declining size. For each cluster, the table
depicts the distribution of nucleotides for each position along the context sequence.

| Cluster | | | | | | |
|---|---|---|---|---|---|---|
| 1433 | t | t | a | a | a | a |
| | 19.05 | 29.09 | 73.83 | 65.10 | 57.50 | 50.03 |
| | 46.12 | 33.63 | 9.141 | 8.374 | 10.81 | 12.63 |
| | 24.49 | 23.23 | 10.53 | 23.86 | 3.838 | 23.16 |
| | 10.32 | 14.02 | 6.489 | 2.651 | 27.84 | 14.16 |
| 1345 | a | a | g | a | a | a |
| | 42.08 | 41.48 | 26.54 | 72.26 | 73.53 | 49.07 |
| | 30.85 | 29.07 | 12.93 | 1.040 | 9.293 | 5.204 |
| | 14.20 | 12.56 | 51.59 | 24.83 | 12.11 | 31.15 |
| | 12.86 | 16.87 | 8.921 | 1.858 | 5.055 | 14.57 |
| 751 | a | a | a | a | c | a |
| | 77.36 | 38.88 | 94.67 | 84.68 | 32.75 | 79.62 |
| | 6.125 | 1.731 | 0.665 | 5.592 | 2.263 | 2.396 |
| | 12.91 | 31.29 | 2.396 | 7.856 | 9.986 | 11.05 |
| | 3.595 | 28.09 | 2.263 | 1.864 | 54.99 | 6.924 |
| 680 | g | a | g | a | a | a |
| | 23.38 | 44.11 | 8.382 | 91.17 | 48.23 | 77.5 |
| | 20.58 | 27.79 | 7.941 | 2.794 | 34.11 | 6.470 |
| | 34.70 | 5.882 | 66.91 | 3.676 | 11.17 | 12.94 |
| | 21.32 | 22.20 | 16.76 | 2.352 | 6.470 | 3.088 |
| 680 | t | c | a | g | c | a |
| | 8.088 | 6.323 | 51.61 | 24.11 | 36.17 | 62.20 |
| | 74.11 | 42.35 | 26.91 | 18.67 | 7.058 | 10.88 |
| | 11.61 | 3.235 | 5.147 | 47.94 | 9.117 | 8.970 |
| | 6.176 | 48.08 | 16.32 | 9.264 | 47.64 | 17.94 |
| 655 | t | c | t | t | c | a |
| | 4.122 | 5.496 | 9.770 | 8.396 | 14.80 | 52.97 |
| | 81.37 | 24.27 | 69.31 | 34.96 | 30.99 | 7.328 |
| | 10.83 | 11.29 | 6.870 | 23.66 | 3.816 | 9.465 |
| | 3.664 | 58.93 | 14.04 | 32.97 | 50.38 | 30.22 |
| 618 | c | a | a | a | c | a |
| | 10.51 | 44.17 | 80.09 | 72.00 | 9.385 | 59.87 |
| | 15.37 | 22.00 | 3.883 | 19.41 | 17.31 | 7.766 |
| | 12.94 | 5.177 | 11.00 | 7.443 | 5.987 | 7.443 |
| | 61.16 | 28.64 | 5.016 | 1.132 | 67.31 | 24.91 |
| 462 | a | g | a | g | a | a |
| | 93.07 | 5.411 | 95.45 | 20.34 | 89.39 | 41.12 |
| | 5.844 | 1.731 | 2.380 | 1.731 | 1.298 | 18.83 |
| | 0 | 88.52 | 1.731 | 75.32 | 3.896 | 35.93 |
| | 1.082 | 4.329 | 0.432 | 2.597 | 5.411 | 4.112 |
| 457 | g | a | a | a | a | a |
| | 12.03 | 75.92 | 65.86 | 50.98 | 52.29 | 53.61 |
| | 1.750 | 4.814 | 14.66 | 10.06 | 7.877 | 12.91 |
| | 84.68 | 2.625 | 15.97 | 29.32 | 8.752 | 13.34 |
| | 1.531 | 16.63 | 3.501 | 9.628 | 31.07 | 20.13 |
| 375 | a | t | c | a | c | c |
| | 77.06 | 24.26 | 1.866 | 62.93 | 5.866 | 13.06 |
| | 14.93 | 54.4 | 5.6 | 9.6 | 30.93 | 12.26 |
| | 4.266 | 1.333 | 2.133 | 24.53 | 1.333 | 8.8 |
| | 3.733 | 20 | 90.4 | 2.933 | 61.86 | 65.86 |
| 327 | a | a | g | a | a | g |
| | 93.57 | 85.32 | 1.529 | 90.82 | 70.94 | 11.31 |
| | 2.446 | 0.305 | 0.611 | 0.305 | 6.727 | 3.975 |
| | 1.834 | 9.785 | 96.94 | 8.562 | 1.834 | 82.56 |
| | 2.140 | 4.587 | 0.917 | 0.305 | 20.48 | 2.140 |
| 306 | a | a | a | a | a | a |
| | 84.96 | 55.22 | 88.56 | 93.13 | 83.66 | 66.66 |
| | 3.921 | 16.01 | 1.633 | 0.653 | 1.633 | 5.228 |
| | 1.307 | 14.70 | 4.248 | 3.921 | 2.941 | 19.28 |
| | 9.803 | 14.05 | 5.555 | 2.287 | 11.76 | 8.823 |
| 305 | c | a | a | a | a | a |
| | 24.91 | 77.37 | 92.45 | 96.06 | 62.29 | 42.95 |
| | 4.262 | 4.262 | 2.622 | 0 | 26.55 | 12.78 |
| | 0.327 | 10.16 | 2.295 | 2.950 | 6.557 | 9.508 |
| | 70.49 | 8.196 | 2.622 | 0.983 | 4.590 | 34.75 |
| 305 | t | c | a | a | t | c |
| | 15.40 | 23.93 | 78.03 | 68.19 | 19.67 | 1.967 |
| | 67.21 | 19.01 | 1.311 | 7.540 | 57.04 | 1.967 |
| | 8.196 | 5.245 | 9.508 | 16.39 | 1.967 | 0.983 |
| | 9.180 | 51.80 | 11.14 | 7.868 | 21.31 | 95.08 |
| 302 | t | c | a | t | c | a |
| | 1.655 | 1.324 | 40.72 | 19.20 | 0.662 | 66.88 |
| | 60.92 | 0.993 | 27.81 | 44.70 | 2.649 | 3.311 |
| | 9.602 | 2.649 | 29.47 | 28.47 | 0 | 18.54 |
| | 27.81 | 95.03 | 1.986 | 7.615 | 96.68 | 11.25 |

TABLE 1-continued

Emerging gene clusters which were identified by the clustering algorithm pertaining *Arabidopsis Thaliana*.
The below clusters are arranged according to declining size. For each cluster, the table
depicts the distribution of nucleotides for each position along the context sequence.

| | | | | | | |
|---|---|---|---|---|---|---|
| 245 | t | c | a | a | a | a |
| | 22.85 | 6.530 | 74.69 | 85.30 | 90.61 | 74.28 |
| | 55.91 | 22.85 | 3.673 | 0.408 | 3.265 | 1.632 |
| | 18.36 | 28.16 | 18.77 | 11.42 | 3.265 | 22.44 |
| | 2.857 | 42.44 | 2.857 | 2.857 | 2.857 | 1.632 |
| 242 | t | c | a | t | c | a |
| | 3.305 | 1.239 | 47.93 | 18.18 | 0 | 85.95 |
| | 72.72 | 2.066 | 42.14 | 72.72 | 2.066 | 4.958 |
| | 8.264 | 2.892 | 9.090 | 2.479 | 0 | 4.132 |
| | 15.70 | 93.80 | 0.826 | 6.611 | 97.93 | 4.958 |
| | 17.90 | 7.860 | 17.03 | 16.59 | 20.08 | 24.01 |
| | 13.97 | 83.40 | 36.24 | 50.21 | 11.35 | 17.03 |
| | 24.89 | 0.873 | 3.056 | 27.51 | 6.550 | 23.14 |
| | 43.23 | 7.860 | 43.66 | 5.676 | 62.00 | 35.80 |
| 219 | a | t | c | a | a | a |
| | 82.19 | 34.70 | 2.283 | 97.71 | 95.89 | 70.31 |
| | 5.936 | 39.26 | 2.739 | 0 | 0.913 | 17.35 |
| | 2.739 | 11.41 | 7.762 | 0.913 | 0.913 | 2.739 |
| | 9.132 | 14.61 | 87.21 | 1.369 | 2.283 | 9.589 |
| 196 | t | c | t | c | t | a |
| | 10.20 | 5.102 | 2.040 | 3.061 | 8.673 | 37.24 |
| | 58.67 | 29.59 | 93.87 | 10.20 | 65.30 | 18.36 |
| | 8.673 | 16.32 | 1.020 | 21.93 | 4.081 | 29.08 |
| | 22.44 | 48.97 | 3.061 | 64.79 | 21.93 | 15.30 |
| 187 | t | a | g | a | a | g |
| | 6.951 | 42.24 | 29.94 | 88.77 | 99.46 | 3.208 |
| | 41.71 | 9.625 | 4.278 | 1.069 | 0 | 0.534 |
| | 32.08 | 8.021 | 60.42 | 4.812 | 0 | 93.58 |
| | 19.25 | 40.10 | 5.347 | 5.347 | 0.534 | 2.673 |
| 176 | g | a | a | g | a | a |
| | 1.704 | 71.59 | 87.5 | 1.136 | 58.52 | 39.20 |
| | 1.704 | 7.386 | 1.704 | 2.272 | 15.34 | 8.522 |
| | 96.02 | 13.63 | 6.818 | 96.59 | 2.272 | 25 |
| | 0.568 | 7.386 | 3.977 | 0 | 23.86 | 27.27 |
| 165 | c | t | t | t | c | ac |
| | 2.424 | 9.696 | 3.030 | 10.90 | 9.090 | 32.12 |
| | 31.51 | 62.42 | 55.15 | 44.84 | 36.36 | 5.454 |
| | 2.424 | 3.030 | 0.606 | 19.39 | 5.454 | 30.30 |
| | 63.63 | 24.84 | 41.21 | 24.84 | 49.09 | 32.12 |
| 162 | g | t | t | t | t | a |
| | 24.07 | 17.90 | 8.641 | 1.851 | 7.407 | 38.88 |
| | 8.641 | 40.74 | 85.80 | 88.88 | 57.40 | 8.024 |
| | 64.19 | 17.28 | 3.703 | 8.024 | 3.703 | 32.71 |
| | 3.086 | 24.07 | 1.851 | 1.234 | 31.48 | 20.37 |
| 161 | g | c | a | g | a | g |
| | 26.08 | 17.39 | 47.20 | 43.47 | 93.78 | 3.105 |
| | 1.242 | 2.484 | 9.937 | 8.074 | 4.968 | 1.863 |
| | 47.82 | 3.105 | 34.16 | 48.44 | 1.242 | 65.21 |
| | 24.84 | 77.01 | 8.695 | 0 | 0 | 29.81 |
| 160 | c | t | a | a | a | a |
| | 3.125 | 13.12 | 33.75 | 74.37 | 51.25 | 94.37 |
| | 3.125 | 53.12 | 12.5 | 13.12 | 4.375 | 0.625 |
| | 1.25 | 3.125 | 25 | 5.625 | 9.375 | 3.75 |
| | 92.5 | 30.62 | 28.75 | 6.875 | 35 | 1.25 |
| 157 | a | t | t | c | a | g |
| | 57.32 | 26.11 | 1.273 | 1.273 | 64.96 | 29.93 |
| | 35.66 | 50.95 | 98.72 | 14.64 | 4.458 | 9.554 |
| | 5.095 | 3.821 | 0 | 8.917 | 0.636 | 56.05 |
| | 1.910 | 19.10 | 0 | 75.15 | 29.93 | 4.458 |
| 155 | t | t | t | g | a | a |
| | 0 | 1.290 | 7.096 | 3.225 | 77.41 | 67.74 |
| | 90.96 | 92.90 | 49.03 | 1.935 | 12.90 | 13.54 |
| | 1.935 | 2.580 | 27.09 | 90.96 | 1.935 | 14.19 |
| | 7.096 | 3.225 | 16.77 | 3.870 | 7.741 | 4.516 |
| 152 | t | t | c | a | a | a |
| | 3.947 | 19.73 | 11.18 | 46.05 | 69.07 | 61.18 |
| | 78.94 | 64.47 | 18.42 | 14.47 | 23.02 | 7.894 |
| | 7.894 | 9.868 | 30.26 | 29.60 | 4.605 | 21.05 |
| | 9.210 | 5.921 | 40.13 | 9.868 | 3.289 | 9.868 |
| 150 | g | t | g | a | c | g |
| | 10 | 28.66 | 1.333 | 71.33 | 25.33 | 22.66 |
| | 0.666 | 50 | 29.33 | 2 | 19.33 | 28 |
| | 81.33 | 8.666 | 48.66 | 20 | 11.33 | 36.66 |
| | 8 | 12.66 | 20.66 | 6.666 | 44 | 12.66 |
| 139 | g | c | g | a | a | a |
| | 23.02 | 23.02 | 16.54 | 80.57 | 60.43 | 67.62 |

TABLE 1-continued

Emerging gene clusters which were identified by the clustering algorithm pertaining *Arabidopsis Thaliana*.
The below clusters are arranged according to declining size. For each cluster, the table
depicts the distribution of nucleotides for each position along the context sequence.

|  |  |  |  |  |  |  |
|---|---|---|---|---|---|---|
|  | 4.316 | 6.474 | 0.719 | 7.913 | 17.26 | 15.10 |
|  | 69.78 | 2.877 | 79.13 | 10.07 | 9.352 | 13.66 |
|  | 2.877 | 67.62 | 3.597 | 1.438 | 12.94 | 3.597 |
| 131 | c | t | g | a | a | a |
|  | 25.19 | 7.633 | 0.763 | 82.44 | 94.65 | 61.06 |
|  | 31.29 | 51.90 | 3.053 | 1.526 | 0 | 9.923 |
|  | 11.45 | 37.40 | 93.12 | 13.74 | 2.290 | 21.37 |
|  | 32.06 | 3.053 | 3.053 | 2.290 | 3.053 | 7.633 |
| 120 | g | g | a | a | a | a |
|  | 19.16 | 3.333 | 95 | 88.33 | 46.66 | 70 |
|  | 14.16 | 0.833 | 0.833 | 5.833 | 23.33 | 4.166 |
|  | 51.66 | 95 | 2.5 | 5 | 14.16 | 7.5 |
|  | 15 | 0.833 | 1.666 | 0.833 | 15.83 | 18.33 |
| 117 | a | t | c | a | t | c |
|  | 75.21 | 0.854 | 5.982 | 88.88 | 3.418 | 0 |
|  | 12.82 | 92.30 | 3.418 | 2.564 | 70.94 | 0.854 |
|  | 7.692 | 0 | 0.854 | 3.418 | 0 | 0 |
|  | 4.273 | 6.837 | 89.74 | 5.128 | 25.64 | 99.14 |
| 109 | a | c | g | g | c | g |
|  | 61.46 | 3.669 | 0.917 | 40.36 | 37.61 | 8.256 |
|  | 3.669 | 5.504 | 2.752 | 1.834 | 0.917 | 2.752 |
|  | 29.35 | 0 | 96.33 | 55.96 | 0 | 85.32 |
|  | 5.504 | 90.82 | 0 | 1.834 | 61.46 | 3.669 |
| 108 | t | g | a | g | t | g |
|  | 12.96 | 9.259 | 83.33 | 0 | 25 | 43.51 |
|  | 85.18 | 25 | 3.703 | 1.851 | 39.81 | 11.11 |
|  | 1.851 | 56.48 | 8.333 | 97.22 | 5.555 | 44.44 |
|  | 0 | 9.259 | 4.629 | 0.925 | 29.62 | 0.925 |
| 104 | g | a | a | a | a | a |
|  | 0.961 | 93.26 | 86.53 | 97.11 | 90.38 | 69.23 |
|  | 32.69 | 3.846 | 3.846 | 0 | 0.961 | 7.692 |
|  | 63.46 | 0.961 | 1.923 | 0.961 | 1.923 | 19.23 |
|  | 2.884 | 1.923 | 7.692 | 1.923 | 6.730 | 3.846 |
| 100 | t | c | g | a | a | a |
|  | 9 | 37 | 1 | 97 | 86 | 82 |
|  | 66 | 6 | 1 | 0 | 0 | 5 |
|  | 21 | 9 | 72 | 2 | 5 | 8 |
|  | 4 | 48 | 26 | 1 | 9 | 5 |
| 93 | g | a | a | g | a | a |
|  | 9.677 | 89.24 | 88.17 | 5.376 | 95.69 | 89.24 |
|  | 12.90 | 0 | 5.376 | 2.150 | 1.075 | 4.301 |
|  | 48.38 | 9.677 | 5.376 | 86.02 | 0 | 3.225 |
|  | 29.03 | 1.075 | 1.075 | 6.451 | 3.225 | 3.225 |
| 85 | c | t | t | t | c | t |
|  | 7.058 | 2.352 | 4.705 | 17.64 | 17.64 | 29.41 |
|  | 4.705 | 95.29 | 60 | 70.58 | 3.529 | 34.11 |
|  | 10.58 | 1.176 | 1.176 | 7.058 | 1.176 | 15.29 |
|  | 77.64 | 1.176 | 34.11 | 4.705 | 77.64 | 21.17 |
| 81 | a | t | c | a | c | c |
|  | 88.88 | 32.09 | 2.469 | 39.50 | 7.407 | 9.876 |
|  | 3.703 | 59.25 | 1.234 | 22.22 | 9.876 | 8.641 |
|  | 1.234 | 2.469 | 2.469 | 33.33 | 1.234 | 27.16 |
|  | 6.172 | 6.172 | 93.82 | 4.938 | 81.48 | 54.32 |
| 67 | t | t | g | g | a | a |
|  | 0 | 0 | 4.477 | 0 | 91.04 | 62.68 |
|  | 68.65 | 98.50 | 5.970 | 1.492 | 4.477 | 29.85 |
|  | 28.35 | 0 | 65.67 | 98.50 | 2.985 | 5.970 |
|  | 2.985 | 1.492 | 23.88 | 0 | 1.492 | 1.492 |
| 67 | c | a | a | t | c | c |
|  | 1.492 | 80.59 | 92.53 | 40.29 | 2.985 | 23.88 |
|  | 0 | 4.477 | 4.477 | 47.76 | 2.985 | 5.970 |
|  | 0 | 8.955 | 0 | 11.94 | 0 | 17.91 |
|  | 98.50 | 5.970 | 2.985 | 0 | 94.02 | 52.23 |
| 61 | t | a | a | g | c | c |
|  | 36.06 | 47.54 | 67.21 | 0 | 0 | 4.918 |
|  | 45.90 | 4.918 | 11.47 | 40.98 | 6.557 | 3.278 |
|  | 8.196 | 27.86 | 18.03 | 59.01 | 3.278 | 1.639 |
|  | 9.836 | 19.67 | 3.278 | 0 | 90.16 | 90.16 |
| 54 | a | c | a | a | g | g |
|  | 53.70 | 22.22 | 96.29 | 94.44 | 9.259 | 3.703 |
|  | 9.259 | 3.703 | 0 | 3.703 | 0 | 14.81 |
|  | 20.37 | 27.77 | 0 | 0 | 87.03 | 68.51 |
|  | 16.66 | 46.29 | 3.703 | 1.851 | 3.703 | 12.96 |
| 52 | t | t | a | g | c | c |
|  | 26.92 | 0 | 84.61 | 28.84 | 0 | 5.769 |
|  | 34.61 | 86.53 | 0 | 0 | 1.923 | 1.923 |

TABLE 1-continued

Emerging gene clusters which were identified by the clustering algorithm pertaining *Arabidopsis Thaliana*.
The below clusters are arranged according to declining size. For each cluster, the table
depicts the distribution of nucleotides for each position along the context sequence.

|    |       |       |       |       |       |       |
|----|-------|-------|-------|-------|-------|-------|
|    | 3.846 | 11.53 | 1.923 | 67.30 | 0     | 1.923 |
|    | 34.61 | 1.923 | 13.46 | 3.846 | 98.07 | 90.38 |
| 47 | g     | c     | a     | a     | t     | c     |
|    | 6.382 | 36.17 | 68.08 | 93.61 | 0     | 0     |
|    | 2.127 | 0     | 6.382 | 4.255 | 51.06 | 6.382 |
|    | 89.36 | 23.40 | 6.382 | 2.127 | 23.40 | 14.89 |
|    | 2.127 | 40.42 | 19.14 | 0     | 25.53 | 78.72 |
| 46 | g     | t     | g     | g     | c     | c     |
|    | 2.173 | 0     | 26.08 | 0     | 2.173 | 19.56 |
|    | 30.43 | 100   | 2.173 | 2.173 | 10.86 | 6.521 |
|    | 58.69 | 0     | 71.73 | 95.65 | 0     | 21.73 |
|    | 8.695 | 0     | 0     | 2.173 | 86.95 | 52.17 |
| 43 | c     | t     | a     | a     | c     | a     |
|    | 0     | 2.325 | 97.67 | 95.34 | 0     | 58.13 |
|    | 6.976 | 81.39 | 0     | 0     | 13.95 | 0     |
|    | 16.27 | 6.976 | 0     | 4.651 | 32.55 | 2.325 |
|    | 76.74 | 9.302 | 2.325 | 0     | 53.48 | 39.53 |
| 43 | g     | t     | a     | a     | t     | c     |
|    | 0     | 20.93 | 67.44 | 95.34 | 32.55 | 0     |
|    | 0     | 37.20 | 0     | 4.651 | 39.53 | 0     |
|    | 100   | 11.62 | 4.651 | 0     | 0     | 0     |
|    | 0     | 30.23 | 27.90 | 0     | 27.90 | 100   |
| 42 | a     | a     | a     | g     | t     | c     |
|    | 92.85 | 42.85 | 97.61 | 7.142 | 0     | 19.04 |
|    | 7.142 | 4.761 | 2.380 | 2.380 | 97.61 | 11.90 |
|    | 0     | 40.47 | 0     | 90.47 | 0     | 7.142 |
|    | 0     | 11.90 | 0     | 0     | 2.380 | 61.90 |
| 42 | t     | c     | t     | t     | g     | a     |
|    | 9.523 | 2.380 | 33.33 | 0     | 0     | 95.23 |
|    | 78.57 | 4.761 | 57.14 | 97.61 | 26.19 | 0     |
|    | 11.90 | 4.761 | 9.523 | 0     | 40.47 | 2.380 |
|    | 0     | 88.09 | 0     | 2.380 | 33.33 | 2.380 |
| 40 | t     | t     | a     | g     | c     | c     |
|    | 15    | 0     | 42.5  | 0     | 0     | 15    |
|    | 80    | 95    | 27.5  | 7.5   | 0     | 30    |
|    | 5     | 0     | 17.5  | 92.5  | 0     | 0     |
|    | 0     | 5     | 12.5  | 0     | 100   | 55    |
| 36 | g     | g     | a     | g     | a     | ag    |
|    | 19.44 | 5.555 | 72.22 | 2.777 | 100   | 44.44 |
|    | 13.88 | 5.555 | 13.88 | 0     | 0     | 0     |
|    | 55.55 | 86.11 | 0     | 97.22 | 0     | 44.44 |
|    | 11.11 | 2.777 | 13.88 | 0     | 0     | 11.11 |
| 35 | c     | t     | c     | t     | c     | t     |
|    | 0     | 0     | 2.857 | 14.28 | 0     | 40    |
|    | 42.85 | 100   | 5.714 | 71.42 | 14.28 | 42.85 |
|    | 2.857 | 0     | 2.857 | 8.571 | 25.71 | 5.714 |
|    | 54.28 | 0     | 88.57 | 5.714 | 60    | 11.42 |
| 35 | a     | a     | t     | c     | a     | a     |
|    | 71.42 | 45.71 | 25.71 | 5.714 | 100   | 97.14 |
|    | 8.571 | 34.28 | 57.14 | 0     | 0     | 2.857 |
|    | 8.571 | 14.28 | 0     | 0     | 0     | 0     |
|    | 11.42 | 5.714 | 17.14 | 94.28 | 0     | 0     |
| 34 | t     | t     | c     | t     | c     | c     |
|    | 8.823 | 0     | 0     | 32.35 | 0     | 20.58 |
|    | 91.17 | 88.23 | 0     | 50    | 47.05 | 23.52 |
|    | 0     | 11.76 | 5.882 | 5.882 | 0     | 2.941 |
|    | 0     | 0     | 94.11 | 11.76 | 52.94 | 52.94 |
| 32 | a     | c     | g     | g     | a     | g     |
|    | 56.25 | 6.25  | 6.25  | 3.125 | 65.62 | 9.375 |
|    | 0     | 12.5  | 0     | 0     | 3.125 | 3.125 |
|    | 43.75 | 0     | 93.75 | 96.87 | 0     | 84.37 |
|    | 0     | 81.25 | 0     | 0     | 31.25 | 3.125 |
| 32 | a     | a     | t     | c     | a     | a     |
|    | 75    | 46.87 | 15.62 | 0     | 100   | 81.25 |
|    | 3.125 | 25    | 78.12 | 0     | 0     | 15.62 |
|    | 12.5  | 25    | 0     | 0     | 0     | 0     |
|    | 9.375 | 3.125 | 6.25  | 100   | 0     | 3.125 |
| 28 | t     | g     | a     | t     | c     | g     |
|    | 0     | 0     | 96.42 | 0     | 3.571 | 32.14 |
|    | 92.85 | 0     | 0     | 92.85 | 3.571 | 3.571 |
|    | 3.571 | 96.42 | 3.571 | 3.571 | 0     | 46.42 |
|    | 3.571 | 3.571 | 0     | 3.571 | 92.85 | 17.85 |
| 28 | g     | c     | t     | g     | t     | a     |
|    | 0     | 3.571 | 7.142 | 0     | 0     | 53.57 |
|    | 0     | 3.571 | 89.28 | 32.14 | 78.57 | 0     |

TABLE 1-continued

Emerging gene clusters which were identified by the clustering algorithm pertaining *Arabidopsis Thaliana*.
The below clusters are arranged according to declining size. For each cluster, the table
depicts the distribution of nucleotides for each position along the context sequence.

| Size | | | | | | |
|---|---|---|---|---|---|---|
| | 100 | 42.85 | 0 | 53.57 | 7.142 | 25 |
| | 0 | 50 | 3.571 | 14.28 | 14.28 | 21.42 |
| 27 | c | g | g | a | a | a |
| | 3.703 | 14.81 | 3.703 | 100 | 96.29 | 59.25 |
| | 33.33 | 0 | 0 | 0 | 0 | 0 |
| | 25.92 | 85.18 | 96.29 | 0 | 0 | 40.74 |
| | 37.03 | 0 | 0 | 0 | 3.703 | 0 |
| 26 | c | c | g | a | c | c |
| | 0 | 30.76 | 23.07 | 100 | 11.53 | 0 |
| | 3.846 | 0 | 23.07 | 0 | 15.38 | 0 |
| | 0 | 26.92 | 42.30 | 0 | 7.692 | 3.846 |
| | 96.15 | 42.30 | 11.53 | 0 | 65.38 | 96.15 |
| 26 | g | t | g | a | a | g |
| | 0 | 3.846 | 3.846 | 46.15 | 61.53 | 0 |
| | 0 | 80.76 | 0 | 7.692 | 0 | 0 |
| | 92.30 | 15.38 | 96.15 | 38.46 | 19.23 | 100 |
| | 7.692 | 0 | 0 | 7.692 | 19.23 | 0 |
| 25 | t | c | a | g | a | g |
| | 16 | 4 | 68 | 36 | 92 | 4 |
| | 68 | 4 | 0 | 0 | 8 | 4 |
| | 16 | 0 | 0 | 64 | 0 | 88 |
| | 0 | 92 | 32 | 0 | 0 | 4 |
| 25 | g | g | t | g | t | a |
| | 0 | 4 | 0 | 0 | 0 | 52 |
| | 0 | 4 | 100 | 24 | 76 | 0 |
| | 100 | 48 | 0 | 60 | 8 | 24 |
| | 0 | 44 | 0 | 16 | 16 | 24 |
| 25 | g | g | a | a | g | g |
| | 20 | 0 | 96 | 44 | 16 | 0 |
| | 32 | 0 | 4 | 12 | 0 | 4 |
| | 48 | 100 | 0 | 36 | 84 | 68 |
| | 0 | 0 | 0 | 8 | 0 | 28 |
| 24 | c | t | c | g | a | c |
| | 20.83 | 0 | 4.166 | 0 | 83.33 | 0 |
| | 0 | 100 | 0 | 0 | 12.5 | 37.5 |
| | 37.5 | 0 | 0 | 100 | 0 | 16.66 |
| | 41.66 | 0 | 95.83 | 0 | 4.166 | 45.83 |

TABLE 2

Emerging gene clusters which were identified by the clustering algorithm pertaining *Homo Sapien*.
The below clusters are arranged according to declining size. For each cluster, the table depicts the
distribution of nucleotides for each position along the context sequence.

| Size of Cluster (number of context sequences)) | Function attributes set (Enrichment score/P_value/Benjamini) | | Distribution of nucleotides per position along the context sequence (%) | | |
|---|---|---|---|---|---|
| | | Pos: | −9 | −8 | −7 |
| 1562 | cytoskeleton (4.63, 3.7E−7, 2.3E−4); transport (4.63, 9.3E−9, 2.5E−6); transporter activity (4.63, 8.4E−3, 6.2E−1); keratin (4.05, 3.0E−8, 5.9E−6); intermediate filament cytoskeleton (4.05, 7.6E−7, 2.4E−4); Keratin, high sulfur B2 protein (4.05, 2.5E−6, 1.3E−2); negative regulation of physiological process (3.46, 8.2E−5, 5.4E−2); regulation of apoptosis (2.91, 9.7E−5, 4.6E−2); positive regulation of apoptosis (2.91, 8.3E−4, 1.3E−1); apoptosis (2.91, 1.2E−3, 1.6E−1); developmental protein (2.76, 1.3E−4, 1.3E−2); differentiation (2.76, 1.2E−3, 4.8E−2); anti-apoptosis (2.71, 1.7E−2, 5.7E−1); golgi stack (2.61, 4.5E−4, 2.5E−2); Golgi apparatus (2.61, 2.2E−3, 9.2E−2); cellular localization (2.46, 2.4E−3, 2.1E−1); cell organization and biogenesis (2.46, 1.2E−2, 5.0E−1); actin binding (2.44, 5.8E−4, 1.7E−1); organ morphogenesis (2.23, 6.3E−4, 1.1E−1); SF002014: carcinoembryonic antigen (1.97, 7.1E−7, 1.8E−3); pregnancy (1.97, 1.2E−4, 3.8E−2); reproduction (1.97, 1.2E−4, 3.5E−2); pregnancy (1.97, 3.3E−4, 1.9E−2); domain: Ig-like V-type (1.97, 1.0E−3, 1.2E−1); magnesium (1.93, 1.9E−3, 6.5E−2); phosphoric monoester hydrolase activity (1.91, 7.8E−6, 9.7E−3); dephosphorylation (1.91, 3.9E−3, 2.9E−1); protein phosphatase type 1 activity (1.91, 1.0E−2, 6.7E−1); | A %<br>T %<br>G %<br>C % | g<br>7.746<br>7.554<br>67.22<br>17.47 | c<br>3.457<br>3.072<br>20.42<br>73.04 | c<br>16.00<br>14.78<br>22.79<br>46.41 |

TABLE 2-continued

Emerging gene clusters which were identified by the clustering algorithm pertaining Homo Sapien.
The below clusters are arranged according to declining size. For each cluster, the table depicts the
distribution of nucleotides for each position along the context sequence.

| | | | | | |
|---|---|---|---|---|---|
| | calcium-dependent protein serine/threonine phosphatase activity (1.91, 1.1E−2, 6.9E−1); kinase (1.82, 1.6E−4, 1.5E−2); atp-binding (1.82, 2.6E−4, 1.9E−2); transferase (1.82, 6.4E−4, 3.0E−2); purine nucleotide binding (1.82, 1.0E−3, 2.5E−1); phosphorus metabolism (1.82, 9.4E−3, 4.5E−1); adenyl nucleotide binding (1.82, 1.1E−2, 6.8E−1); ATP (1.82, 4.9E−2, 5.4E−1); myosin (1.58, 6.5E−2, 5.6E−1); reproduction (1.58, 1.2E−4, 3.5E−2); spermatogenesis (1.58, 8.8E−2, 6.7E−1); protein modification (1.58, 1.3E−2, 5.2E−1); oxidoreductase activity, acting on the CH—NH2 group of donors (1.49, 3.3E−3, 4.2E−1); domain: Ubiquitin-like (1.46, 5.7E−3, 4.8E−1); cell-matrix junction (1.33, 3.5E−2, 4.5E−1); focal adhesion (1.33, 1.1E−1, 6.9E−1); microtubule (1.3, 1.3E−3, 5.0E−2); microtubule (1.3, 5.6E−3, 1.7E−1); muscle protein (1.26, 2.0E−3, 6.8E−2); myofibril (1.26, 4.2E−2, 4.6E−1); sarcomere (1.26, 1.0E−1, 6.9E−1); selenium (1.21, 6.1E−2, 5.9E−1); protease (1.2, 2.5E−3, 7.9E−2); serine protease (1.2, 2.7E−3, 8.1E−2); initiation factor (1.15, 7.4E−2, 6.3E−1); cholesterol metabolism (1.15, 1.3E−2, 5.2E−1); steroid metabolism (1.15, 5.1E−2, 5.5E−1); lipid metabolism (1.15, 5.4E−2, 5.6E−1); guanine-nucleotide releasing factor (1.14, 4.9E−3, 1.2E−1); ruffle (1.13, 3.9E−2, 4.6E−1); cell projection (1.13, 6.9E−2, 5.7E−1); vitamin a (1.08, 6.7E−2, 6.1E−1); secretory pathway (1.06, 2.0E−2, 6.3E−1); iron (1.04, 5.5E−4, 2.8E−2); | | | | |
| 987 | transport (3.62, 1.8E−6, 4.9E−4); lysosome (3.03, 1.3E−4, 1.7E−2); lytic vacuole (3.03, 2.7E−3, 3.4E−1); intracellular signaling cascade (2.61, 5.2E−4, 3.6E−1); KRAB-related (2.49, 1.2E−7, 6.1E−4); ion transport (1.79, 7.3E−4, 7.3E−2); potassium (1.79, 2.3E−3, 1.6E−1); voltage-gated channel (1.79, 2.2E−2, 5.0E−1); differentiation (1.65, 1.1E−2, 4.0E−1); ATPase activity, coupled to transmembrane movement of substances (1.6, 1.4E−3, 6.9E−1); hydrolase activity, acting on acid anhydrides, catalyzing transmembrane movement of substances (1.6, 2.4E−3, 6.9E−1); atp synthesis (1.6, 6.0E−3, 2.9E−1); hydrogen ion transport (1.6, 9.6E−3, 3.7E−1); growth regulation (1.59, 7.1E−3, 3.1E−1); actin-binding (1.43, 6.9E−3, 3.1E−1); lipoprotein (1.39, 1.6E−2, 4.6E−1); wnt signaling pathway (1.23, 1.7E−2, 4.6E−1); cell cycle (1.17, 4.8E−3, 2.5E−1); nucleotide-binding (1.14, 7.2E− 6, 1.4E−3); atp-binding (1.14, 2.3E−4, 2.8E−2); transferase (1.14, 1.1E−3, 9.7E−2); prenylation (0.98, 4.9E−2, 6.9E−1); growth factor (0.94, 2.7E−2, 5.5E−1); thick filament (0.91, 2.0E−2, 5.1E−1); muscle protein (0.91, 3.1E−2, 5.9E−1); methylation (0.91, 4.2E−2, 6.5E−1); golgi stack (0.9, 2.6E−2, 5.4E−1); mitochondrion (0.86, 5.0E−2, 6.9E−1); cell cycle (0.84, 4.8E−3, 2.5E−1); cell division (0.84, 2.2E−2, 5.1E−1); redox-active center (0.82, 3.3E−2, 6.1E−1); chaperone (0.75, 5.2E−2, 6.9E−1); lipid synthesis (0.73, 1.6E−2, 4.6E−1); protein phosphatase inhibitor (0.68, 5.6E−2, 6.9E−1); aminoacyltransferase (0.62, 5.6E−2, 6.9E−1); immune response (0.31, 3.5E−2, 6.0E−1); nuclear protein (0.29, 4.7E−2, 6.8E−1); nuclear protein (0.22, 4.7E−2, 6.8E−1); | A % <br> T % <br> G % <br> C % | c <br> 5.065 <br> 10.23 <br> 26.74 <br> 57.95 | c <br> 2.735 <br> 10.63 <br> 26.54 <br> 60.08 | c <br> 17.93 <br> 21.07 <br> 25.63 <br> 35.35 |
| 407 | response to pest, pathogen or parasite (2.79, 4.5E−5, 1.4E−1); response to wounding (2.79, 8.1E−5, 1.3E−1); response to other organism (2.79, 1.1E−4, 1.2E−1); response to stress (2.79, 2.0E−4, 1.5E−1); ANTIGEN PROCESSING AND PRESENTATION (2.36, 1.2E−3, 2.1E−1); immunoglobulin domain (2.36, 3.7E−3, 3.5E−1); signal (2.17, 6.0E−6, 8.2E−3); transmembrane (2.17, 1.0E−3, 2.1E−1); glycoprotein (2.17, 1.1E−3, 1.9E−1); Glutathione S-transferase, Mu class (1.81, 3.4E−5, 1.6E−1); nucleotide phosphate-binding region: PAPS (1.57, 8.6E−5, 2.9E−1); aryl sulfotransferase activity (1.57, 6.2E−4, 5.4E−1); sulfotransferase activity (1.57, 9.2E−4, 5.4E−1); transferase activity, transferring sulfur-containing groups (1.57, 1.4E−3, 5.9E−1); catecholamine metabolism (1.57, 2.2E−3, 2.9E−1); sulfotransferase (1.57, 6.5E−3, 4.9E−1); lipid metabolism (1.57, 8.3E−3, 5.1E−1); intermediate filament (1.47, 2.4E−3, 2.8E−1); membrane (1.35, 7.8E−5, 2.6E−2); transmembrane (1.35, 1.0E−3, 2.1E−1); developmental protein (1.11, 8.8E−3, 5.1E−1); | A % <br> T % <br> G % <br> C % | g <br> 26.53 <br> 6.879 <br> 38.82 <br> 27.76 | c <br> 10.31 <br> 13.02 <br> 36.11 <br> 40.54 | c <br> 5.651 <br> 3.439 <br> 14.49 <br> 76.41 |

TABLE 2-continued

Emerging gene clusters which were identified by the clustering algorithm pertaining Homo Sapien.
The below clusters are arranged according to declining size. For each cluster, the table depicts the
distribution of nucleotides for each position along the context sequence.

| | | | | | |
|---|---|---|---|---|---|
| | transcription factor (0.85, 7.3E−3, 4.9E−1); transferase (0.5, 1.9E−3, 2.8E−1); | | | | |
| 398 | locomotion (3.03, 9.3E−4, 6.5E−1); localization of cell (3.03, 9.3E−4, 6.5E−1); cell motility (3.03, 9.3E−4, 6.5E−1); ribonucleoprotein (1.56, 2.0E−4, 8.5E−2); ribosome (1.56, 9.5E−3, 6.6E−1); RNA binding (1.47, 2.2E−4, 4.2E−1); rna-binding (1.47, 6.4E−4, 2.0E−1); cell cycle (0.91, 5.5E−3, 5.6E−1); cell division (0.91, 1.1E−2, 6.7E−1); sodium/potassium transport (0.81, 3.6E−3, 5.6E−1); potassium transport (0.81, 7.7E−3, 6.5E−1); potassium (0.81, 1.1E−2, 6.9E−1); | A %<br>T %<br>G %<br>C % | g<br>5.527<br>3.266<br>73.61<br>17.58 | c<br>5.276<br>13.56<br>21.10<br>60.05 | c<br>7.286<br>13.06<br>25.37<br>54.27 |
| 368 | isomerase (1.4, 3.4E−3, 6.9E−1); | A %<br>T %<br>G %<br>C % | g<br>13.31<br>5.706<br>55.97<br>25 | g<br>2.445<br>13.58<br>77.98<br>5.978 | c<br>1.902<br>3.260<br>17.66<br>77.17 |
| 347 | hormone (2.01, 2.1E−3, 4.4E−1); transport (1.83, 7.4E−4, 2.2E−1); signal (1.79, 5.9E−6, 4.0E−3); lipid transport (0.97, 2.2E−3, 3.9E−1); nuclear protein (0.86, 4.6E−3, 5.9E−1); ubl conjugation pathway (0.79, 5.5E−3, 5.6E−1); nuclear protein (0.64, 4.6E−3, 5.9E−1); membrane (0.57, 5.0E−3, 5.8E−1); | A %<br>T %<br>G %<br>C % | t<br>30.54<br>32.27<br>20.74<br>16.42 | c<br>2.305<br>11.81<br>36.88<br>48.99 | c<br>6.628<br>11.23<br>2.305<br>79.82 |
| 245 | membrane (0.88, 2.2E−3, 5.3E−1); | A %<br>T %<br>G %<br>C % | g<br>2.040<br>1.632<br>58.36<br>37.95 | c<br>4.081<br>2.448<br>1.632<br>91.83 | c<br>11.42<br>10.20<br>20.40<br>57.95 |
| 196 | transcription cofactor activity (1.23, 3.9E−4, 6.2E−1); transcription cofactor activity (1.07, 3.9E−4, 6.2E−1); signal-anchor (0.99, 2.1E−3, 6.1E−1); | A %<br>T %<br>G %<br>C % | c<br>28.57<br>15.30<br>22.95<br>33.16 | g<br>5.612<br>2.551<br>88.26<br>3.571 | c<br>17.85<br>3.571<br>33.67<br>44.89 |
| 177 | defensin (2.34, 2.7E−4, 3.1E−1); SF001875: mammalian defensin (2.34, 3.6E−4, 6.1E−1); Mammalian defensin (2.34, 4.4E−4, 5.3E−1); DEFSN (2.34, 4.5E−4, 2.3E−1); fungicide (2.34, 1.2E−3, 4.2E−1); antibiotic (2.34, 1.6E−3, 4.2E−1); antimicrobial (2.34, 1.7E−3, 3.8E−1); homodimer (2.34, 2.3E−3, 4.0E−1); | A %<br>T %<br>G %<br>C % | t<br>6.214<br>46.89<br>33.33<br>13.55 | c<br>12.42<br>7.344<br>4.519<br>75.70 | c<br>9.039<br>10.73<br>3.389<br>76.83 |
| 175 | zinc ion binding (1.72, 1.5E−5, 3.8E−2); transition metal ion binding (1.72, 6.4E−5, 7.8E−2); zinc (1.72, 7.1E−4, 6.2E−1); nuclear protein (1.72, 9.1E−4, 4.6E−1); zinc-finger (1.72, 1.4E−3, 4.8E−1); | A %<br>T %<br>G %<br>C % | g<br>7.428<br>6.285<br>50.85<br>35.42 | a<br>66.85<br>9.142<br>4<br>20 | g<br>18.85<br>16.57<br>61.71<br>2.857 |
| 165 | membrane (1.34, 6.2E−4, 3.4E−1); | A %<br>T %<br>G %<br>C % | g<br>16.96<br>9.090<br>41.81<br>32.12 | a<br>53.33<br>18.78<br>18.78<br>9.090 | g<br>16.96<br>1.212<br>78.18<br>3.636 |
| 161 | Glycoside hydrolase family 13 (2.56, 7.0E−5, 3.0E−1); Alpha amylase, all-beta (2.56, 7.0E−5, 3.0E−1); Aamy_C (2.56, 9.2E−5, 5.2E−2); SF500178: alpha-amylase, short form (2.56, 1.2E−4, 2.6E−1); SF001019: alpha-amylase (2.56, 1.2E−4, 2.6E−1); binding site: Chloride (2.56, 3.0E−4, 6.9E−1); Alpha amylase, catalytic region (2.56, 3.5E−4, 4.5E−1); Alpha amylase, catalytic subdomain (2.56, 3.5E−4, 4.5E−1); amylase activity (2.56, 4.3E−4, 6.6E−1); alpha-amylase activity (2.56, 4.3E−4, 6.6E−1); Aamy (2.56, 4.6E−4, 1.2E−1); | A %<br>T %<br>G %<br>C % | g<br>12.42<br>4.968<br>76.39<br>6.211 | a<br>73.91<br>0<br>25.46<br>0.621 | a<br>93.78<br>0.621<br>3.726<br>1.863 |
| 106 | nucleotide binding (3.76, 3.2E−5, 7.6E−2); nucleotide-binding (3.76, 3.8E−5, 5.1E−2); ATP binding (3.76, 6.4E−5, 7.7E−2); adenyl nucleotide binding (3.76, 9.8E−5, 7.9E−2); purine nucleotide binding (3.76, 1.5E−4, 8.8E−2); atp-binding (3.76, 1.5E−4, 9.8E−2); | A %<br>T %<br>G %<br>C % | c<br>16.03<br>5.660<br>29.24<br>49.05 | t<br>2.830<br>54.71<br>0.943<br>41.50 | t<br>5.660<br>92.45<br>0<br>1.886 |
| 104 | keratin (4.63, 2.9E−8, 4.0E−5); repeat: 6 (4.63, 5.7E−8, 2.3E−4); repeat: 5 (4.63, 1.5E−7, 2.9E−4); repeat: 1 (4.63, 2.6E−7, 3.5E−4); repeat: 2 (4.63, 2.7E−7, 2.7E−4); repeat: 4 (4.63, 3.4E−7, 2.7E−4); intermediate filament cytoskeleton (4.63, 9.3E−7, 5.8E−4); intermediate filament (4.63, 9.3E−7, 5.8E−4); repeat: 3 (4.63, 1.0E−6, 6.8E−4); repeat: 7 (4.63, 9.8E−6, 5.6E−3); repeat: 8 (4.63, 1.1E−3, 4.3E−1); SF000050: human cytochrome P450 CYP4B1 (2.01, 9.6E−6, 2.4E−2); E-class P450, group I (2.01, 5.5E−5, 2.5E−1); electron transport (2.01, 1.2E−4, 3.3E−1); generation of precursor metabolites and energy (2.01, 2.0E−4, 2.9E−1); Cytochrome P450 (2.01, 2.3E−4, 4.5E−1); monooxygenase (2.01, 3.4E−4, 2.1E−1); tetrapyrrole binding (2.01, 8.7E−4, | A %<br>T %<br>G %<br>C % | g<br>39.42<br>2.884<br>41.34<br>16.34 | a<br>72.11<br>0.961<br>6.730<br>20.19 | c<br>3.846<br>1.923<br>43.26<br>50.96 |

TABLE 2-continued

Emerging gene clusters which were identified by the clustering algorithm pertaining Homo Sapien.
The below clusters are arranged according to declining size. For each cluster, the table depicts the
distribution of nucleotides for each position along the context sequence.

| | | | | | |
|---|---|---|---|---|---|
| | 5.2E−1); heme binding (2.01, 8.7E−4, 5.2E−1); heme (2.01, 1.2E−3, 4.2E−1); monooxygenase activity (2.01, 1.2E−3, 5.3E−1); SCP (1.91, 1.6E−3, 6.1E−1); | | | | |
| 104 | structural protein (1.38, 3.6E−4, 3.9E−1); cytoskeleton (1.38,1.5E−3, 6.5E−1); | | a | a | g |
| | | A % | 92.30 | 80.76 | 33.65 |
| | | T % | 1.923 | 3.846 | 0.961 |
| | | G % | 1.923 | 12.5 | 60.57 |
| | | C % | 3.846 | 2.884 | 4.807 |
| 101 | organelle envelope (2.43, 1.4E−3, 5.8E−1); envelope (2.43, 1.6E−3, 3.8E−1); nuclear envelope (2.43, 7.0E−3, 5.8E−1); endomembrane system (2.43, 1.3E−2, 6.8E−1); cytoplasm (1.34, 3.2E−3, 4.8E−1); intracellular (1.34, 5.0E−3, 5.4E−1); electron transport (1.13, 5.3E−4, 3.0E−1); OXIDATIVE PHOSPHORYLATION (1.13, 4.9E−3, 6.2E−1); | | c | a | a |
| | | A % | 3.960 | 51.48 | 88.11 |
| | | T % | 15.84 | 6.930 | 2.970 |
| | | G % | 33.66 | 10.89 | 4.950 |
| | | C % | 46.53 | 30.69 | 3.960 |
| 82 | transmembrane (1.68, 1.6E−3, 6.5E−1); | | c | t | g |
| | | A % | 1.219 | 0 | 0 |
| | | T % | 24.39 | 97.56 | 8.536 |
| | | G % | 18.29 | 2.439 | 80.48 |
| | | C % | 56.09 | 0 | 10.97 |
| 76 | SF001638: cystatin (2.05, 1.4E−4, 3.1E−1); site: Reactive site (2.05, 2.6E−4, 6.5E−1); thiol protease inhibitor (2.05, 8.4E−4, 6.8E−1); CY (2.05, 1.4E−3, 5.6E−1); | | c | g | g |
| | | A % | 13.15 | 40.78 | 3.947 |
| | | T % | 3.947 | 11.84 | 5.263 |
| | | G % | 35.52 | 46.05 | 89.47 |
| | | C % | 47.36 | 1.315 | 1.315 |
| 75 | Keratin, high sulfur B2 protein (3.3, 5.8E−6, 3.0E−2); repeat: 18 (3.3, 9.1E−6, 3.6E−2); keratin filament (3.3, 1.1E−5, 6.5E−3); intermediate filament cytoskeleton (3.3, 2.4E−4, 4.9E−2); intermediate filament (3.3, 2.4E−4, 4.9E−2); plasma membrane (0.85, 6.9E−3, 6.6E−1); | | c | a | c |
| | | A % | 0 | 54.66 | 1.333 |
| | | T % | 2.666 | 9.333 | 4 |
| | | G % | 1.333 | 6.666 | 26.66 |
| | | C % | 96 | 29.33 | 68 |
| 72 | tumor antigen (6.54, 9.0E−14, 1.2E−10); domain: MAGE (6.54, 3.5E−11, 1.4E−7); SF005491: tumor associated protein MAGE (6.54, 3.9E−11, 1.0E−7); MAGE protein (6.54, 2.1E−10, 1.1E−6); multigene family (6.54, 3.9E−7, 2.6E−4); antigen (6.54, 8.1E−6, 3.7E−3); | | a | g | a |
| | | A % | 68.05 | 0 | 50 |
| | | T % | 2.777 | 6.944 | 1.388 |
| | | G % | 26.38 | 90.27 | 11.11 |
| | | C % | 2.777 | 2.777 | 37.5 |
| 72 | nuclear protein (2.71, 3.6E−8, 4.9E−5); transcription (2.71, 2.7E−6, 1.8E−3); transcription regulation (2.71, 3.4E−6, 1.5E−3); KRAB box (2.71, 4.4E−5, 2.0E−1); zinc finger region: C2H2-type 9 (2.71, 8.6E−5, 2.9E−1); KRAB (2.71, 9.0E−5, 5.1E−2); dna-binding (2.71, 1.0E−4, 3.4E−2); intracellular membrane-bound organelle (2.71, 7.6E−4, 2.1E−1); metal-binding (2.71, 1.2E−3, 2.7E−1); regulation of nucleobase, nucleoside, nucleotide and nucleic acid metabolism (2.71, 1.3E−3, 5.8E−1); | | g | g | a |
| | | A % | 44.44 | 1.388 | 47.22 |
| | | T % | 2.777 | 1.388 | 11.11 |
| | | G % | 52.77 | 95.83 | 33.33 |
| | | C % | 0 | 1.388 | 8.333 |
| 71 | SF002282: cytoskeletal keratin (1.84, 1.3E−4, 2.9E−1); intermediate filament (1.84, 3.3E−4, 3.6E−1); keratin (1.84, 2.2E−3, 6.3E−1); | | c | t | t |
| | | A % | 40.84 | 0 | 5.633 |
| | | T % | 0 | 91.54 | 76.05 |
| | | G % | 0 | 1.408 | 1.408 |
| | | C % | 59.15 | 7.042 | 16.90 |
| 69 | KRAB box (3.66, 2.1E−10, 1.1E−6); Zinc finger, C2H2-subtype (3.66, 1.4E−9, 3.6E−6); KRAB (3.66, 3.4E−9, 2.0E−6); zinc (3.66, 6.7E−9, 9.1E−6); Zinc finger, C2H2-type (3.66, 8.8E−9, 1.5E−5); zinc-finger (3.66, 1.1E−8, 7.6E−6); transcription (3.66, 7.1E−8, 3.2E−5); transcription regulation (3.66, 9.5E−8, 3.2E−5); zinc ion binding (3.66, 1.4E−7, 3.5E−4); transition metal ion binding (3.66, 1.5E−7, 1.8E−4); ZnF_C2H2 (3.66, 1.6E−7, 4.6E−5); metal-binding (3.66, 2.9E−7, 7.9E−5); nuclear protein (3.66, 2.6E−6, 6.0E−4); cation binding (3.66, 3.5E−6, 2.9E−3); zinc finger region: C2H2-type 8 (3.66, 1.1E−5, 4.2E−2); regulation of transcription (3.66, 1.2E−5, 4.1E−2); metal ion binding (3.66, 1.2E−5, 6.3E−3); ion binding (3.66, 1.2E−5, 6.3E−3); regulation of nucleobase, nucleoside, nucleotide and nucleic acid metabolism (3.66, 1.5E−5, 2.5E−2); regulation of transcription, DNA-dependent (3.66, 2.0E−5, 2.2E−2); zinc finger region: C2H2-type 7 (3.66, 2.1E−5, 4.2E−2); domain: KRAB (3.66, 2.2E−5, 2.9E−2); transcription (3.66, 2.4E−5, 2.0E−2); transcription, DNA-dependent (3.66, 3.0E−5, 2.0E−2); regulation of cellular metabolism (3.66, 3.4E−5, 1.9E−2); zinc finger region: C2H2-type 6 (3.66, 3.5E−5, 3.5E−2); General function prediction only (3.66, 4.4E−5, 3.0E−3); regulation of metabolism (3.66, 5.0E−5, 2.4E−2); zinc finger region: C2H2-type 5 (3.66, 8.1E−5, 6.3E−2); zinc finger region: C2H2-type 4 (3.66, 1.3E−4, 8.6E−2); zinc finger region: C2H2-type 1 (3.66, 1.6E−4, 8.6E−2); nucleic | | c | t | g |
| | | A % | 1.449 | 27.53 | 14.49 |
| | | T % | 23.18 | 72.46 | 1.449 |
| | | G % | 2.898 | 0 | 76.81 |
| | | C % | 72.46 | 0 | 7.246 |

TABLE 2-continued

Emerging gene clusters which were identified by the clustering algorithm pertaining Homo Sapien.
The below clusters are arranged according to declining size. For each cluster, the table depicts the
distribution of nucleotides for each position along the context sequence.

| | | | | | |
|---|---|---|---|---|---|
| | acid binding (3.66, 1.9E−4, 7.5E−2); zinc finger region: C2H2-type 2 (3.66, 2.5E−4, 1.2E−1); zinc finger region: C2H2-type 3 (3.66, 2.9E−4, 1.2E−1); nucleobase, nucleoside, nucleotide and nucleic acid metabolism (3.66, 5.5E−4, 2.1E−1); regulation of cellular physiological process (3.66, 7.0E−4, 2.3E−1); regulation of physiological process (3.66, 1.0E−3, 3.0E−1); regulation of biological process (3.66, 1.1E−3, 3.0E−1); regulation of cellular process (3.66, 1.3E−3, 3.1E−1); dna-binding (3.66, 4.5E−3, 5.9E−1); | | | | |
| 67 | signal (2.42, 9.0E−5, 1.2E−1); glycoprotein (2.42, 5.7E−4, 3.2E−1); sushi (2.17, 3.3E−3, 6.8E−1); domain: Ig-like C2-type 3 (1.73, 1.9E−4, 5.3E−1); cell adhesion (1.73, 5.0E−3, 6.8E−1); transcription regulation (1.27, 1.5E−3, 4.8E−1); | | c | t | g |
| | | A % | 5.970 | 0 | 20.89 |
| | | T % | 2.985 | 70.14 | 0 |
| | | G % | 2.985 | 28.35 | 76.11 |
| | | C % | 88.05 | 1.492 | 2.985 |
| 63 | GLUTATHIONE METABOLISM (1.93, 5.5E−3, 6.6E−1); | | a | c | t |
| | | A % | 87.30 | 3.174 | 7.936 |
| | | T % | 0 | 6.349 | 84.12 |
| | | G % | 6.349 | 7.936 | 3.174 |
| | | C % | 6.349 | 82.53 | 4.761 |
| 60 | cellular metabolism (1.98, 1.3E−5, 4.4E−2); metabolism (1.98, 7.5E−5, 1.2E−1); primary metabolism (1.98, 8.6E−4, 6.2E−1); cellular physiological process (1.98, 9.7E−4, 5.6E−1); intracellular membrane-bound organelle (1.98, 1.9E−3, 6.9E−1); membrane-bound organelle (1.98, 1.9E−3, 4.4E−1); regulation of cellular process (1.98, 2.4E−3, 6.9E−1); cytoplasm (1.98, 4.7E−3, 6.3E−1); intracellular (1.98, 5.8E−3, 6.0E−1); intracellular organelle (1.98, 8.4E−3, 6.5E−1); organelle (1.98, 8.5E−3, 5.9E−1); | | c | c | c |
| | | A % | 1.666 | 1.666 | 3.333 |
| | | T % | 1.666 | 36.66 | 0 |
| | | G % | 0 | 6.666 | 3.333 |
| | | C % | 96.66 | 55 | 93.33 |
| 50 | domain: KRAB (13.16, 2.7E−29, 1.1E−25); KRAB box (13.16, 1.9E−27, 1.0E−23); KRAB (13.16, 1.9E−24, 1.1E−21); zinc finger region: C2H2-type 10 (13.16, 2.7E−24, 5.4E−21); Zinc finger, C2H2-subtype (13.16, 3.7E−24, 9.6E−21); zinc finger region: C2H2-type 7 (13.16, 8.0E−24, 1.1E−20); transcription (13.16, 3.4E−19, 4.6E−16); transcription regulation (13.16, 5.4E−19, 3.6E−16); zinc finger region: C2H2-type 3 (13.16, 8.9E−19, 3.2E−16); zinc finger region: C2H2-type 5 (13.16, 9.8E−19, 3.3E−16); dna-binding (13.16, 1.3E−17, 4.6E−15); regulation of nucleobase, nucleoside, nucleotide and nucleic acid metabolism (13.16, 7.1E−14, 6.0E−11); regulation of cellular metabolism (13.16, 2.7E−13, 1.5E−10); regulation of metabolism (13.16, 5.3E−13, 2.3E−10); nucleic acid binding (13.16, 4.8E−10, 3.0E−7); primary metabolism (13.16, 1.6E−5, 4.2E−3); intracellular membrane-bound organelle (13.16, 3.5E−5, 1.1E−2); zinc finger region: C2H2-type 14 (7.98, 3.1E−16, 9.5E−14); zinc finger region: C2H2-type 15 (7.98, 2.3E−13, 6.3E−11); zinc finger region: C2H2-type 16 (7.98, 1.1E−8, 2.7E−6); zinc finger region: C2H2-type 17 (7.98, 5.3E−6, 1.1E−3); zinc finger region: C2H2-type 18 (7.98, 1.1E−4, 2.1E−2); zinc finger region: C2H2-type 19 (7.98, 2.7E−3, 3.9E−1); SF005559: zinc finger protein ZFP-36 (3.77, 9.7E−7, 2.5E−3); | | a | g | c |
| | | A % | 100 | 6 | 4 |
| | | T % | 0 | 10 | 16 |
| | | G % | 0 | 84 | 2 |
| | | C % | 0 | 0 | 78 |
| 47 | B melanoma antigen (2.56, 3.3E−8, 1.7E−4); | | t | g | c |
| | | A % | 46.80 | 25.53 | 34.04 |
| | | T % | 48.93 | 6.382 | 0 |
| | | G % | 2.127 | 65.95 | 0 |
| | | C % | 2.127 | 2.127 | 65.95 |
| 45 | zinc-finger (2.04, 1.0E−4, 1.3E−1); ion binding (2.04, 3.4E−4, 3.5E−1); metal ion binding (2.04, 3.4E−4, 3.5E−1); zinc (2.04, 5.4E−4, 3.1E−1); cation binding (2.04, 5.8E−4, 3.8E−1); metal-binding (2.04, 8.0E−4, 3.0E−1); zinc ion binding (2.04, 8.7E−4, 4.2E−1); transition metal ion binding (2.04, 1.1E−3, 4.3E−1); DNA binding (2.04, 1.6E−3, 4.8E−1); DNA binding (1.33, 1.6E−3, 4.8E−1); DNA binding (0.99, 1.6E−3, 4.8E−1); | | g | g | c |
| | | A % | 0 | 26.66 | 0 |
| | | T % | 0 | 13.33 | 40 |
| | | G % | 100 | 48.88 | 2.222 |
| | | C % | 0 | 11.11 | 57.77 |
| 44 | DNA binding (1.99, 9.4E−4, 6.9E−1); | | g | c | c |
| | | A % | 0 | 0 | 4.545 |
| | | T % | 0 | 0 | 18.18 |
| | | G % | 90.90 | 0 | 2.272 |
| | | C % | 9.090 | 100 | 75 |
| 44 | Zinc finger, C2H2-subtype (2.11, 2.9E−9, 1.5E−5); ZnF_C2H2 (2.11, 1.4E−6, 8.2E−4); Zinc finger, C2H2-type (2.11, 2.5E−6, 6.4E−3); KRAB (2.11, 8.7E−6, 2.5E−3); zinc-finger (2.11, 1.1E−5, 1.4E−2); zinc ion binding (2.11, 4.3E−5, 1.0E−1); transition metal ion binding (2.11, | | g | a | g |
| | | A % | 2.272 | 100 | 0 |
| | | T % | 0 | 0 | 0 |
| | | G % | 95.45 | 0 | 97.72 |
| | | C % | 2.272 | 0 | 2.272 |

TABLE 2-continued

Emerging gene clusters which were identified by the clustering algorithm pertaining *Homo Sapien*. The below clusters are arranged according to declining size. For each cluster, the table depicts the distribution of nucleotides for each position along the context sequence.

| | | | | | |
|---|---|---|---|---|---|
| | 5.3E−5, 6.4E−2); zinc (2.11, 6.2E−5, 4.1E−2); metal-binding (2.11, 7.6E−5, 3.4E−2); nucleic acid binding (2.11, 4.5E−4, 3.1E−1); ion binding (2.11, 8.1E−4, 3.3E−1); metal ion binding (2.11, 8.1E−4, 3.3E−1); cation binding (2.11, 1.5E−3, 4.7E−1); transcription (2.11, 2.5E−3, 5.7E−1); transcription regulation (2.11, 2.8E−3, 5.3E−1); nuclear protein (2.11, 4.7E−3, 6.6E−1); Transcription/Cell division and chromosome partitioning (2.11, 5.9E−3, 1.8E−1); | | | | |
| 43 | domain: MAGE (3.45, 2.3E−5, 8.9E−2); MAGE protein (3.45, 2.4E−5, 1.2E−1); antigen (3.45, 4.5E−4, 4.6E−1); | | a | c | a |
| | | A % | 67.44 | 4.651 | 100 |
| | | T % | 11.62 | 4.651 | 0 |
| | | G % | 0 | 9.302 | 0 |
| | | C % | 20.93 | 81.39 | 0 |

| Size of Cluster (number of context sequences)) | Distribution of nucleotides per position along the context sequence (%) | | | | | |
|---|---|---|---|---|---|---|
| | −6 | −5 | −4 | −3 | −2 | −1 |
| 1562 | g | c | c | a | c | c |
| | 5.121 | 6.978 | 4.737 | 65.55 | 3.329 | 1.728 |
| | 4.929 | 7.746 | 2.240 | 2.176 | 6.402 | 0.896 |
| | 72.79 | 33.73 | 8.130 | 29.89 | 10.94 | 3.713 |
| | 17.15 | 51.53 | 84.89 | 2.368 | 79.32 | 93.66 |
| 987 | g | g | a | g | c | c |
| | 14.89 | 3.850 | 39.31 | 1.722 | 4.863 | 1.013 |
| | 8.510 | 7.700 | 9.827 | 0.607 | 5.065 | 1.013 |
| | 47.01 | 46.80 | 17.62 | 95.84 | 3.444 | 4.964 |
| | 29.58 | 41.64 | 33.23 | 1.823 | 86.62 | 93.00 |
| 407 | a | g | c | a | c | c |
| | 75.92 | 3.194 | 1.474 | 92.62 | 7.371 | 3.931 |
| | 12.28 | 2.702 | 0.737 | 0.491 | 5.896 | 0.982 |
| | 7.371 | 92.62 | 24.81 | 5.159 | 19.16 | 7.862 |
| | 4.422 | 1.474 | 72.97 | 1.719 | 67.56 | 87.22 |
| 398 | g | c | c | a | a | g |
| | 2.512 | 5.778 | 2.763 | 93.96 | 75.87 | 3.015 |
| | 18.34 | 9.547 | 2.010 | 0 | 0 | 1.005 |
| | 69.59 | 35.17 | 16.83 | 2.010 | 21.10 | 87.68 |
| | 9.547 | 49.49 | 78.39 | 4.020 | 3.015 | 8.291 |
| 368 | c | c | c | g | c | c |
| | 3.532 | 1.086 | 27.71 | 1.630 | 2.989 | 2.445 |
| | 10.59 | 12.5 | 2.173 | 0.271 | 2.173 | 1.630 |
| | 16.84 | 6.793 | 20.38 | 96.73 | 1.630 | 4.891 |
| | 69.02 | 79.61 | 49.72 | 1.358 | 93.20 | 91.03 |
| 347 | t | c | c | a | g | g |
| | 16.71 | 4.034 | 6.628 | 92.21 | 30.54 | 3.746 |
| | 36.59 | 18.73 | 4.034 | 2.017 | 0.864 | 1.440 |
| | 12.39 | 32.85 | 8.357 | 2.593 | 66.85 | 78.67 |
| | 34.29 | 44.38 | 80.97 | 3.170 | 1.729 | 16.13 |
| 245 | g | a | g | g | c | c |
| | 8.979 | 35.91 | 0.816 | 10.61 | 1.632 | 8.979 |
| | 4.489 | 6.938 | 1.224 | 2.448 | 0 | 2.857 |
| | 62.04 | 23.26 | 97.95 | 84.08 | 15.10 | 27.34 |
| | 24.48 | 33.87 | 0 | 2.857 | 83.26 | 60.81 |
| 196 | g | g | g | a | a | g |
| | 35.71 | 28.06 | 1.530 | 97.44 | 68.87 | 2.040 |
| | 2.040 | 2.040 | 0.510 | 0 | 0.510 | 1.020 |
| | 57.65 | 67.34 | 97.44 | 2.040 | 30.10 | 94.89 |
| | 4.591 | 2.551 | 0.510 | 0.510 | 0.510 | 2.040 |
| 177 | c | c | a | g | c | c |
| | 23.72 | 2.824 | 77.40 | 25.42 | 2.824 | 2.259 |
| | 22.59 | 3.389 | 6.779 | 0.564 | 2.259 | 2.259 |
| | 3.954 | 0 | 11.86 | 74.01 | 2.824 | 1.694 |
| | 49.71 | 93.78 | 3.954 | 0 | 92.09 | 93.78 |
| 175 | g | a | g | a | g | g |
| | 4.571 | 68.57 | 8 | 52.57 | 95.42 | 12.57 |
| | 1.714 | 28 | 2.285 | 0.571 | 1.142 | 1.142 |
| | 74.85 | 1.142 | 85.14 | 44 | 2.857 | 84 |
| | 18.85 | 2.285 | 4.571 | 2.857 | 0.571 | 2.285 |
| 165 | g | g | a | g | c | c |
| | 1.818 | 17.57 | 92.12 | 30.90 | 26.06 | 1.212 |
| | 3.636 | 4.848 | 3.636 | 0 | 0.606 | 1.212 |
| | 92.12 | 44.24 | 3.636 | 67.27 | 21.21 | 3.030 |
| | 2.424 | 33.33 | 0.606 | 1.818 | 52.12 | 94.54 |

TABLE 2-continued

Emerging gene clusters which were identified by the clustering algorithm pertaining *Homo Sapien*.
The below clusters are arranged according to declining size. For each cluster, the table depicts the
distribution of nucleotides for each position along the context sequence.

| | | | | | | |
|---|---|---|---|---|---|---|
| 161 | a | g | c | a | a | a |
| | 41.61 | 21.73 | 38.50 | 97.51 | 93.78 | 66.45 |
| | 14.90 | 33.54 | 6.211 | 0 | 1.242 | 1.242 |
| | 16.77 | 39.13 | 13.66 | 1.242 | 1.242 | 29.81 |
| | 26.70 | 5.590 | 41.61 | 1.242 | 3.726 | 2.484 |
| 106 | t | c | c | a | a | a |
| | 0.943 | 1.886 | 5.660 | 83.96 | 86.79 | 66.03 |
| | 62.26 | 41.50 | 1.886 | 1.886 | 2.830 | 2.830 |
| | 27.35 | 3.773 | 2.830 | 3.773 | 4.716 | 30.18 |
| | 9.433 | 52.83 | 89.62 | 10.37 | 5.660 | 0.943 |
| 104 | a | g | a | a | c | c |
| | 98.07 | 3.846 | 69.23 | 88.46 | 3.846 | 18.26 |
| | 1.923 | 5.769 | 2.884 | 1.923 | 8.653 | 8.653 |
| | 0 | 88.46 | 10.57 | 1.923 | 7.692 | 14.42 |
| | 0 | 1.923 | 17.30 | 7.692 | 79.80 | 58.65 |
| 104 | a | a | g | a | a | a |
| | 76.92 | 72.11 | 19.23 | 98.07 | 88.46 | 61.53 |
| | 1.923 | 6.730 | 9.615 | 0 | 1.923 | 3.846 |
| | 1.923 | 17.30 | 61.53 | 1.923 | 0.961 | 14.42 |
| | 19.23 | 3.846 | 9.615 | 0 | 8.653 | 20.19 |
| 101 | g | c | c | a | a | g |
| | 24.75 | 3.960 | 0 | 93.06 | 92.07 | 15.84 |
| | 0.990 | 9.900 | 2.970 | 1.980 | 0.990 | 0.990 |
| | 70.29 | 8.910 | 0.990 | 3.960 | 3.960 | 73.26 |
| | 3.960 | 77.22 | 96.03 | 0.990 | 2.970 | 9.900 |
| 82 | g | g | g | a | a | c |
| | 7.317 | 4.878 | 20.73 | 80.48 | 54.87 | 40.24 |
| | 3.658 | 3.658 | 6.097 | 13.41 | 0 | 2.439 |
| | 86.58 | 85.36 | 62.19 | 3.658 | 20.73 | 8.536 |
| | 2.439 | 6.097 | 10.97 | 2.439 | 24.39 | 48.78 |
| 76 | g | a | g | a | c | c |
| | 1.315 | 89.47 | 3.947 | 61.84 | 17.10 | 1.315 |
| | 3.947 | 6.578 | 2.631 | 1.315 | 26.31 | 2.631 |
| | 90.78 | 3.947 | 93.42 | 30.26 | 26.31 | 14.47 |
| | 3.947 | 0 | 0 | 6.578 | 30.26 | 81.57 |
| 75 | c | g | c | a | g | c |
| | 1.333 | 17.33 | 2.666 | 90.66 | 14.66 | 8 |
| | 5.333 | 22.66 | 0 | 4 | 4 | 5.333 |
| | 4 | 34.66 | 2.666 | 1.333 | 60 | 2.666 |
| | 89.33 | 25.33 | 94.66 | 4 | 21.33 | 84 |
| 72 | g | t | c | a | t | c |
| | 16.66 | 2.777 | 0 | 97.22 | 34.72 | 4.166 |
| | 34.72 | 73.61 | 0 | 0 | 63.88 | 0 |
| | 48.61 | 16.66 | 9.722 | 2.777 | 1.388 | 0 |
| | 0 | 6.944 | 90.27 | 0 | 0 | 95.83 |
| 72 | g | g | a | a | a | a |
| | 13.88 | 22.22 | 93.05 | 100 | 88.88 | 56.94 |
| | 2.777 | 1.388 | 0 | 0 | 1.388 | 0 |
| | 83.33 | 58.33 | 1.388 | 0 | 4.166 | 37.5 |
| | 0 | 18.05 | 5.555 | 0 | 5.555 | 5.555 |
| 71 | g | g | a | a | c | c |
| | 19.71 | 0 | 49.29 | 91.54 | 1.408 | 0 |
| | 8.450 | 1.408 | 5.633 | 1.408 | 11.26 | 0 |
| | 71.83 | 67.60 | 4.225 | 7.042 | 1.408 | 0 |
| | 0 | 30.98 | 40.84 | 0 | 85.91 | 100 |
| 69 | a | a | g | a | a | a |
| | 50.72 | 98.55 | 28.98 | 89.85 | 84.05 | 81.15 |
| | 5.797 | 0 | 0 | 1.449 | 5.797 | 7.246 |
| | 26.08 | 0 | 66.66 | 4.347 | 2.898 | 10.14 |
| | 17.39 | 1.449 | 4.347 | 4.347 | 7.246 | 1.449 |
| 67 | c | c | c | a | g | c |
| | 2.985 | 26.86 | 19.40 | 94.02 | 4.477 | 7.462 |
| | 23.88 | 4.477 | 5.970 | 2.985 | 0 | 2.985 |
| | 31.34 | 0 | 11.94 | 2.985 | 95.52 | 10.44 |
| | 41.79 | 68.65 | 62.68 | 0 | 0 | 79.10 |
| 63 | g | c | a | a | t | c |
| | 1.587 | 20.63 | 82.53 | 74.60 | 4.761 | 1.587 |
| | 0 | 6.349 | 11.11 | 3.174 | 47.61 | 0 |
| | 98.41 | 12.69 | 0 | 20.63 | 20.63 | 3.174 |
| | 0 | 60.31 | 6.349 | 1.587 | 26.98 | 95.23 |
| 60 | g | c | c | g | c | g |
| | 31.66 | 1.666 | 3.333 | 1.666 | 0 | 3.333 |
| | 5 | 0 | 1.666 | 3.333 | 0 | 0 |
| | 63.33 | 33.33 | 0 | 90 | 5 | 96.66 |
| | 0 | 65 | 95 | 5 | 95 | 0 |

TABLE 2-continued

Emerging gene clusters which were identified by the clustering algorithm pertaining Homo Sapien. The below clusters are arranged according to declining size. For each cluster, the table depicts the distribution of nucleotides for each position along the context sequence.

| Size | | | | | | |
|---|---|---|---|---|---|---|
| 50 | c | t | a | g | a | a |
| | 8 | 28 | 68 | 0 | 96 | 82 |
| | 0 | 44 | 0 | 0 | 0 | 2 |
| | 8 | 28 | 30 | 100 | 4 | 0 |
| | 84 | 0 | 2 | 0 | 0 | 16 |
| 47 | a | g | c | a | a | g |
| | 87.23 | 4.255 | 2.127 | 93.61 | 100 | 0 |
| | 0 | 4.255 | 25.53 | 0 | 0 | 2.127 |
| | 8.510 | 87.23 | 2.127 | 4.255 | 0 | 95.74 |
| | 4.255 | 4.255 | 70.21 | 2.127 | 0 | 2.127 |
| 45 | g | g | a | g | a | c |
| | 0 | 22.22 | 93.33 | 2.222 | 95.55 | 0 |
| | 20 | 4.444 | 2.222 | 0 | 2.222 | 2.222 |
| | 77.77 | 51.11 | 4.444 | 97.77 | 2.222 | 35.55 |
| | 2.222 | 22.22 | 0 | 0 | 0 | 62.22 |
| 44 | g | c | c | c | g | g |
| | 9.090 | 6.818 | 0 | 2.272 | 0 | 0 |
| | 2.272 | 0 | 2.272 | 9.090 | 4.545 | 6.818 |
| | 86.36 | 6.818 | 29.54 | 27.27 | 77.27 | 93.18 |
| | 2.272 | 86.36 | 68.18 | 61.36 | 18.18 | 0 |
| 44 | g | c | a | g | g | g |
| | 4.545 | 4.545 | 77.27 | 45.45 | 31.81 | 13.63 |
| | 29.54 | 0 | 4.545 | 0 | 2.272 | 4.545 |
| | 47.72 | 0 | 18.18 | 50 | 54.54 | 81.81 |
| | 18.18 | 95.45 | 0 | 4.545 | 11.36 | 0 |
| 43 | g | c | c | a | g | c |
| | 0 | 2.325 | 6.976 | 100 | 30.23 | 2.325 |
| | 2.325 | 2.325 | 2.325 | 0 | 20.93 | 4.651 |
| | 81.39 | 4.651 | 2.325 | 0 | 32.55 | 0 |
| | 16.27 | 90.69 | 88.37 | 0 | 16.27 | 93.02 |

TABLE 3

Emerging gene clusters which were identified by the clustering algorithm pertaining Mus Musculus. The below clusters are arranged according to declining size. For each cluster, the table depicts the distribution of nucleotides for each position along the context sequence.

| Size of Cluster (number of context sequences) | Function attributes set (Enrichment score/P_value/Benjamini) | Distribution of nucleotides per position along the context sequence (%) | | | |
|---|---|---|---|---|---|
| | | Pos: | −9 | −8 | −7 |
| 1197 | intracellular non-membrane-bound organelle (7.46, 1.0E−9, 1.6E−7); non-membrane-bound organelle (7.46, 1.0E−9, 1.6E−7); cytoskeleton (7.46, 1.2E−9, 1.5E−7); organelle organization and biogenesis (7.46, 1.2E−3, 2.2E−1); transport (5.55, 2.2E−11, 6.4E−9); transport (5.55, 4.0E−5, 2.4E−2); transporter activity (5.55, 1.1E−3, 1.2E−1); actin cytoskeleton (4.99, 1.1E−7, 8.7E−6); actin-binding (4.99, 1.5E−6, 1.2E−4); cytoskeletal protein binding (4.99, 1.6E−4, 3.6E−2); actin binding (4.99, 3.8E−4, 6.9E−2); protein transport (3.84, 5.5E−7, 5.3E−5); cell organization and biogenesis (3.84, 1.1E−5, 9.6E−3); protein transporter activity (3.84, 4.4E−5, 1.2E−2); protein localization (3.84, 1.1E−4, 5.4E−2); protein transport (3.84, 2.7E−4, 1.2E−1); establishment of protein localization (3.84, 3.7E−4, 1.4E−1); intracellular transport (3.84, 7.7E−4, 1.8E−1); establishment of cellular localization (3.84, 9.0E−4, 1.9E−1); cellular localization (3.84, 1.1E−3, 2.2E−1); intracellular protein transport (3.84, 2.1E−3, 3.1E−1); tissue kallikrein activity (3.41, 1.3E−12, 3.3E−9); serine protease (3.41, 6.5E−6, 4.1E−4); serine proteinase (3.41, 9.7E−6, 5.6E−4); SF001135: trypsin (3.41, 2.0E−5, 4.2E−2); submandibular gland (3.41, 2.5E−5, 1.2E−3); zymogen (3.41, 3.2E−5, 1.5E−3); protease (3.41, 2.5E−4, 8.9E−3); Peptidase S1A, chymotrypsin (3.41, 8.3E−4, 5.7E−1); Peptidase S1 and S6, chymotrypsin/Hap (3.41, 1.2E−3, 5.9E−1); serine-type endopeptidase activity (3.41, 3.5E−3, 2.9E−1); serine-type peptidase activity (3.41, 6.4E−3, 3.9E−1); Tryp_SPc (3.41, 7.0E−3, 6.4E−1); Pleckstrin-like (3.34, 4.3E−4, 4.2E−1); metal-binding (3.32, 6.2E−7, 5.5E−5); muscle protein (2.87, 7.5E−6, 4.5E−4); contractile fiber (2.87, 2.7E−5, 1.6E−3); | A %<br>T %<br>G %<br>C % | g<br>11.44<br>8.103<br>57.14<br>23.30 | c<br>2.756<br>5.430<br>14.70<br>77.10 | c<br>27.23<br>16.95<br>10.02<br>45.78 |

TABLE 3-continued

Emerging gene clusters which were identified by the clustering algorithm pertaining Mus Musculus. The below clusters are arranged according to declining size. For each cluster, the table depicts the distribution of nucleotides for each position along the context sequence.

|   |   |   | c | c | c |
|---|---|---|---|---|---|
|   |   | A % | 6.901 | 8.309 | 4.084 |
|   |   | T % | 9.295 | 17.60 | 2.816 |
|   |   | G % | 41.69 | 30.56 | 40 |
|   |   | C % | 42.11 | 43.52 | 53.09 | myofibril (2.87, 9.5E−5, 4.5E−3); sarcomere (2.87, 2.4E−4, 9.7E−3); muscle (2.87, 3.6E−3, 7.5E−2); cellular macromolecule metabolism (2.87, 5.1E−3, 4.7E−1); protein metabolism (2.87, 5.4E−3, 4.8E−1); cellular protein metabolism (2.87, 1.1E−2, 5.7E−1); golgi stack (2.82, 3.7E−5, 1.6E−3); Golgi apparatus (2.82, 7.8E−3, 1.6E−1); Golgi stack (2.82, 1.2E−2, 2.2E−1); basolateral plasma membrane (2.61, 8.0E−5, 4.1E−3); adherens junction (2.61, 3.3E−4, 1.2E−2); cell-substrate adherens junction (2.61, 1.4E−3, 4.5E−2); cell-matrix junction (2.61, 2.2E−3, 5.6E−2); focal adhesion (2.61, 4.7E−3, 1.1E−1); Proteasome component region PCI (2.48, 1.7E−4, 3.6E−1); PINT (2.48, 9.4E−4, 1.7E−1); cell projection organization and biogenesis (2.45, 5.8E−4, 1.7E−1); cell projection biogenesis (2.45, 2.5E−3, 3.3E−1); GTPase regulator activity (2.37, 2.1E−3, 2.0E−1); small GTPase regulator activity (2.37, 4.1E−3, 3.1E−1); enzyme regulator activity (2.37, 8.6E−3, 4.5E−1); enzyme binding (2.33, 1.1E−3, 1.2E−1); kinase binding (2.33, 3.7E−3, 2.9E−1); magnesium (2.23, 4.8E−4, 1.6E−2); magnesium ion binding (2.23, 1.0E−2, 4.7E−1); mRNA metabolism (2.21, 7.0E−4, 1.8E−1); mrna processing (2.21, 7.8E−4, 2.3E−2); mRNA processing (2.21, 1.8E−3, 2.9E−1); mrna splicing (2.21, 2.2E−3, 5.0E−2); alkali metal ion binding (2.19, 5.4E−3, 3.5E−1); monovalent inorganic cation transport (2.19, 5.5E−3, 4.7E−1); cation transport (2.19, 7.9E−3, 5.3E−1); ion transport (2.19, 8.3E−3, 5.4E−1); potassium transport (2.19, 1.2E−2, 1.7E−1); ionic channel (2.19, 2.9E−2, 3.2E−1); Arf GTPase activating protein (2.14, 9.4E−5, 3.8E−1); ArfGap (2.14, 1.2E−4, 6.9E−2); carbohydrate metabolism (2.09, 5.6E−4, 1.8E−2); glycogen metabolism (2.09, 1.8E−3, 4.5E−2); glucan metabolism (2.09, 1.4E−2, 6.3E−1); glycogen metabolism (2.09, 1.4E−2, 6.3E−1); desmosome (1.75, 3.1E−5, 1.7E−3); cell junction (1.75, 2.2E−4, 9.6E−3); intercellular junction (1.75, 1.6E−3, 4.7E−2); apicolateral plasma membrane (1.75, 1.9E−3, 5.2E−2); apical junction complex (1.75, 1.9E−3, 5.2E−2); sh3 domain (1.72, 2.1E−3, 5.0E−2);

710 signal (3.82, 2.4E−8, 9.0E−6); glycoprotein (3.82, 6.0E−7, 1.7E−4); extracellular region (3.82, 1.8E−6, 1.1E−3); extracellular space (3.82, 1.9E−6, 5.9E−4); protein metabolism (3.82, 2.1E−4, 1.4E−1; serine/threonine-protein kinase (2.4, 1.2E−5, 1.7E−3); transferase (2.4, 1.7E−5, 1.8E−3); atp-binding (2.4, 7.7E−5, 6.7E−3); kinase (2.4, 2.6E−4, 1.7E−2); protein serine/threonine kinase activity (2.4, 6.6E−4, 2.7E−1); protein-tyrosine kinase activity (2.4, 1.0E−3, 3.4E−1); protein amino acid phosphorylation (2.4, 1.3E−3, 3.0E−1); S_TKc (2.4, 2.0E−3, 6.9E−1); protein kinase activity (2.4, 2.2E−3, 4.4E−1); phosphorylation (2.4, 3.7E−3, 5.1E−1); cAMP-dependent protein kinase activity (2.4, 4.2E−3, 5.4E−1); cyclic nucleotide-dependent protein kinase activity (2.4, 4.2E−3, 5.4E−1); protein kinase CK2 activity (2.4, 4.4E−3, 5.4E−1); phosphotransferase activity, alcohol group as acceptor (2.4, 5.6E−3, 6.0E−1); ATP (2.4, 1.3E−2, 2.8E−1); serine/threonine-specific protein kinase (2.4, 5.6E−2, 6.3E−1); phosphotransferase (2.4, 5.9E−2, 6.3E−1); negative regulation of biological process (2.38, 9.3E−4, 2.5E−1); negative regulation of cellular process (2.38, 1.6E−3, 3.3E−1); negative regulation of physiological process (2.38, 1.7E−3, 3.4E−1); negative regulation of cellular physiological process (2.38, 3.2E−3, 4.7E−1); extrinsic to plasma membrane (2.25, 1.2E−3, 1.7E−1); extrinsic to membrane (2.25, 1.7E−3, 1.9E−1); protein transport (2.22, 4.6E−5, 4.4E−3); cell organization and biogenesis (2.22, 9.0E−5, 1.0E−1); protein localization (2.22, 6.1E−3, 6.7E−1); metal-binding (2.11, 4.4E−6, 8.4E−4); cell cycle (1.85, 6.5E−3, 2.0E−1); anti-oncogene (1.85, 1.6E−2, 3.2E−1); electron transfer (1.77, 3.3E−4, 2.0E−2); chromoprotein (1.77, 5.8E−4, 3.1E−2); heme (1.77, 1.4E−3, 5.8E−2); heme binding (1.77, 2.6E−3, 4.3E−1); tetrapyrrole binding (1.77, 2.6E−3, 4.3E−1); metalloprotein (1.77, 3.2E−3, 1.2E−1); unspecific monooxygenase activity (1.77, 6.7E−3, 6.2E−1); iron (1.77, 7.4E−3, 2.1E−1); monooxygenase (1.77, 1.2E−2, 2.8E−1); oxidoreductase (1.77, 1.9E−2, 3.4E−1); microsome (1.77, 4.1E−2, 5.5E−1); golgi stack (1.69, 2.1E−3, 8.1E−2); transport (1.64, 7.3E−4, 3.7E−2);

TABLE 3-continued

Emerging gene clusters which were identified by the clustering algorithm pertaining *Mus Musculus*.
The below clusters are arranged according to declining size. For each cluster, the table depicts
the distribution of nucleotides for each position along the context sequence.

| | | | c | g | g |
|---|---|---|---|---|---|
| 397 | metal-binding (3.5, 6.9E−6, 2.6E−3); zinc (3.5, 5.6E−5, 1.1E−2); cation binding (3.5, 1.8E−4, 1.3E−1); ion binding (3.5, 3.2E−4, 1.8E−1); metal ion binding (3.5, 3.2E−4, 1.8E−1); transition metal ion binding (3.5, 9.0E−4, 3.0E−1); zinc ion binding (3.5, 3.2E−3, 6.3E−1); zinc-finger (3.5, 5.0E−3, 3.3E−1); nuclear protein (3.19, 1.5E−8, 1.7E−5); organelle (3.19, 2.8E−4, 1.6E−1); intracellular organelle (3.19, 6.5E−4, 1.8E−1); membrane-bound organelle (3.19, 1.1E−3, 2.1E−1); intracellular membrane-bound organelle (3.19, 2.4E−3, 3.1E−1); nucleus (3.19, 3.3E−3, 3.4E−1); intracellular (3.19, 5.4E−3, 4.3E−1); nuclear protein (2.99, 1.5E−8, 1.7E−5); regulation of metabolism (2.99, 9.4E−5, 8.2E−2); transcription (2.99, 1.7E−4, 2.4E−2); regulation of physiological process (2.99, 2.1E−4, 1.0E−1); regulation of biological process (2.99, 2.2E−4, 9.5E−2); ); transcription, DNA-dependent (2.99, 1.0E−3, 2.1E−1);; metalloexopeptidase activity (1.22, 2.1E−3, 5.2E−1); glycosyltransferase (1.09, 2.1E−2, 6.9E−1); calcium (1.09, 1.4E−2, 5.6E−1); transport (0.96, 1.3E−2, 5.4E−1); nucleotide-binding (0.43, 2.2E−2, 6.9E−1); | A %<br>T %<br>G %<br>C % | 21.41<br>13.09<br>29.97<br>35.51 | 18.63<br>13.85<br>48.61<br>18.89 | 5.541<br>5.793<br>61.96<br>26.70 |
| | | | g | c | g |
| 357 | ribosomal protein (4.97, 2.6E−8, 3.0E−5); ribonucleoprotein (4.97, 3.8E−8, 2.2E−5); macromolecule biosynthesis (4.97, 4.6E−7, 8.3E−4); cellular biosynthesis (4.97, 5.9E−7, 7.2E−4); biosynthesis (4.97, 7.1E−7, 6.4E−4); structural constituent of ribosome (4.97, 2.3E−6, 5.5E−3); ribosome (4.97, 4.5E−6, 9.2E−4); RIBOSOME (4.97, 5.8E−6, 1.1E−3); protein biosynthesis (4.97, 1.6E−5, 1.1E−2); ribonucleoprotein complex (4.97, 6.6E−5, 1.0E−2); structural molecule activity (4.97, 9.4E−4, 4.3E−1); transport (3.53, 1.1E−4, 2.5E−2); transporter activity (3.53, 1.2E−4, 1.3E−1); establishment of localization (3.53, 5.0E−4, 2.3E−1); transport (3.53, 5.7E−4, 2.0E−1); localization (3.53, 6.4E−4, 2.1E−1); | A %<br>T %<br>G %<br>C % | 5.602<br>4.761<br>71.70<br>17.92 | 18.76<br>5.602<br>29.69<br>45.93 | 23.80<br>6.162<br>35.57<br>34.45 |
| | | | g | g | c |
| 373 | cytoplasm (2.19, 6.6E−5, 4.0E−2); intracellular (2.19, 1.2E−3, 3.1E−1); intracellular organelle (2.19, 4.3E−3, 4.8E−1); organelle (2.19, 4.6E−3, 4.3E−1); Defensin propeptide (2.16, 1.1E−4, 4.3E−1); membrane (2.04, 5.8E−9, 6.6E−6); glycoprotein (2.04, 2.0E−5, 1.1E−2); transmembrane (2.04, 5.2E−5, 2.0E−2); signal (2.04, 1.8E−3, 2.0E−1); extracellular region (2.04, 6.0E−3, 4.1E−1); extracellular space (2.04, 8.8E−3, 4.9E−1); ribosomal protein (1.99, 6.8E−5, 1.9E−2); structural constituent of ribosome (1.99, 7.5E−4, 6.0E−1); ribonucleoprotein (1.99, 1.3E−3, 1.7E−1); ribosome (1.99, 5.0E−3, 4.0E−1); heparin binding (1.94, 1.8E−3, 6.6E−1); heparin-binding (1.94, 1.2E−2, 5.0E−1); sh3 domain (1.93, 1.8E−3, 1.9E−1); transit peptide (1.69, 2.2E−3, 1.9E−1); mitochondrion (1.69, 3.6E−3, 5.2E−1); mitochondrion (1.69, 4.8E−3, 3.2E−1); organelle inner membrane (1.69, 1.4E−2, 6.3E−1); gtp-binding (1.64, 6.1E−4, 9.5E−2); nucleotide-binding (1.35, 4.4E−3, 3.2E−1); transport (1.32, 2.2E−3, 2.0E−1); heat shock (1.03, 1.9E−2, 6.4E−1); zinc (1.01, 8.8E−3, 4.5E−1); metal-binding (1.01, 1.1E−2, 5.0E−1); ubl conjugation pathway (0.64, 1.1E−2, 4.8E−1); nuclear protein (0.29, 2.2E−2, 6.9E−1); | A %<br>T %<br>G %<br>C % | 13.13<br>6.702<br>49.06<br>31.09 | 7.774<br>21.17<br>58.98<br>12.06 | 2.680<br>2.949<br>9.383<br>84.98 |
| | | | g | c | t |
| 290 | cytolysis (3.78, 1.5E−7, 1.7E−4); SF001135: trypsin (3.78, 4.3E−7, 9.3E−4); serine proteinase (3.78, 1.0E−6, 5.9E−4); serine protease (3.78, 1.8E−6, 6.7E−4); cytolysis (3.78, 4.5E−6, 1.6E−2); protease (3.78, 1.3E−5, 3.6E−3); zymogen (3.78, 3.4E−5, 7.6E−3); Peptidase S1A, chymotrypsin (3.78, 7.1E−5, 8.7E−2); Tryp_SPc (3.78, 9.7E−5, 2.8E−2); domain: Peptidase S1 (3.78, 1.1E−4, 2.9E−1); serine-type endopeptidase activity (3.78, 1.5E−4, 3.0E−1); Peptidase S1 and S6, chymotrypsin/Hap (3.78, 1.8E−4, 1.4E−1); serine-type peptidase activity (3.78, 2.3E−4, 2.5E−1); proteolysis (3.78, 1.7E−3, 4.9E−1); t-cell (3.78, 2.1E−3, 1.7E−1); peptidase activity (3.78, 2.4E−3, 6.9E−1); hydrolase (3.78, 2.5E−3, 1.7E−1); direct protein sequencing (3.78, 4.6E−3, 2.5E−1); SF001714: Bcl2 related apoptosis regulator (3.2, 3.1E−6, 3.4E−3); Bcl2 related apoptosis regulator (3.2, 4.4E−6, 2.3E−2); Apoptosis regulator, Bcl-2 related (3.2, 7.3E−6, 1.9E−2); BCL (3.2, 1.9E−5, 1.1E−2); BCL2-like apoptosis inhibitor (3.2, 2.7E−5, 4.6E−2); Apoptosis regulator Bcl-2, BH (3.2, 1.1E−4, 1.1E−1); cell death (3.2, 3.2E−4, 1.5E−1); death (3.2, 3.8E−4, 1.6E−1); cellular physiological process (2.27, 1.6E−5, 2.9E−2); protein metabolism (2.27, 7.7E−5, 8.9E−2); cellular macromolecule metabolism (2.27, 7.9E−5, | A %<br>T %<br>G %<br>C % | 8.965<br>6.551<br>61.72<br>22.75 | 2.068<br>2.068<br>32.41<br>63.44 | 25.17<br>38.27<br>11.37<br>25.17 |

TABLE 3-continued

Emerging gene clusters which were identified by the clustering algorithm pertaining *Mus Musculus*. The below clusters are arranged according to declining size. For each cluster, the table depicts the distribution of nucleotides for each position along the context sequence.

| | | | | | |
|---|---|---|---|---|---|
| | 6.9E−2); cellular protein metabolism (2.27, 1.1E−4, 7.4E−2); macromolecule metabolism (2.27, 2.4E−4, 1.4E−1); nuclear protein (1.62, 4.1E−3, 2.4E−1); signal (1.61, 7.7E−5, 1.2E−2); glycoprotein (1.61, 3.7E−4, 4.6E−2); metal-binding (1.41, 1.4E−3, 1.2E−1); zinc (1.41, 2.2E−3, 1.6E−1); zinc-finger (1.41, 1.2E−2, 4.0E−1); nuclear pore (1.38, 9.6E−3, 6.9E−1); pore complex (1.38, 9.6E−3, 6.9E−1); chaperone (1.17, 2.3E−2, 6.0E−1); cell cycle (1.06, 1.2E−2, 4.0E−1); nucleotide-binding (1.02, 6.5E−3, 3.1E−1); transferase (1.02, 7.7E−3, 3.4E−1); atp-binding (1.02, 2.0E−2, 5.7E−1); membrane (0.95, 7.8E−4, 7.8E−2); transmembrane (0.95, 1.0E−2, 3.8E−1); glycosyltransferase (0.92, 5.7E−3, 2.9E−1); rna-binding (0.92, 7.9E−3, 3.4E−1); glycosyltransferase (0.91, 5.7E−3, 2.9E−1); ligase (0.84, 3.0E−3, 2.0E−1); | | | | |
| 283 | Serpin B9 and maspin (3.42, 3.1E−8, 1.6E−4); protease inhibitor activity (3.42, 3.0E−4, 5.1E−1); Proteinase inhibitor I4, serpin (3.42, 3.2E−4, 5.7E−1); enzyme inhibitor activity (3.42, 6.4E−4, 4.0E−1); SERPIN (3.42, 7.0E−4, 1.8E−1); endopeptidase inhibitor activity (3.42, 1.4E−3, 5.8E−1); transport (2.84, 7.3E−5, 2.1E−2); transporter activity (2.84, 4.7E−4, 4.3E−1); membrane (2.77, 1.2E−9, 1.4E−6); transmembrane (2.77, 4.6E−6, 2.6E−3); oxygen carrier (1.69, 1.3E−3, 2.2E−1); oxygen transport (1.69, 1.6E−3, 2.3E−1); oxygen transporter activity (1.69, 3.2E−3, 6.7E−1); ribosomal protein (1.67, 8.7E−4, 1.8E−1); structural constituent of ribosome (1.67, 4.8E−3, 6.9E−1); ribosome (1.67, 5.3E−3, 6.6E−1); ribonucleoprotein (1.67, 1.0E−2, 6.0E−1); cytokine (1.07, 2.4E−3, 2.9E−1); glycoprotein (0.92, 2.9E−3, 3.1E−1); signal (0.92, 3.8E−3, 3.5E−1); cytokine (0.74, 2.4E−3, 2.9E−1); protease (0.66, 8.0E−3, 5.3E−1); | A %<br>T %<br>G %<br>C % | t<br>20.84<br>37.80<br>20.49<br>20.84 | c<br>26.50<br>30.03<br>12.72<br>30.74 | c<br>6.713<br>17.66<br>30.38<br>45.22 |
| 220 | protein transport (2.99, 3.7E−5, 1.4E−2); golgi stack (2.99, 3.0E−4, 6.7E−2); Golgi stack (2.99, 2.9E−3, 2.2E−1); transport (2.99, 3.8E−3, 3.2E−1); Golgi apparatus (2.99, 9.0E−3, 5.0E−1); cellular physiological process (2.46, 4.8E−6, 1.7E−2); nuclear protein (2.46, 2.4E−5, 2.7E−2); intracellular (2.46, 5.7E−5, 3.5E−2); intracellular organelle (2.46, 3.7E−4, 1.1E−1); organelle (2.46, 3.9E−4, 7.7E−2); intracellular membrane-bound organelle (2.46, 1.6E−3, 2.2E−1); membrane-bound organelle (2.46, 1.7E−3, 1.6E−1); mrna processing (2.07, 3.3E−4, 6.1E−2); mrna splicing (2.07, 5.4E−3, 3.8E−1); nuclear protein (1.45, 2.4E−5, 2.7E−2); dna-binding (1.45, 5.4E−4, 7.4E−2); transcription (1.45, 2.0E−2, 6.7E−1); protein transport (1.44, 3.7E−5, 1.4E−2); transport (1.44, 3.8E−3, 3.2E−1); lipoprotein (1.42, 4.6E−4, 7.2E−2); gtp-binding (1.42, 5.5E−3, 3.6E−1); transit peptide (1.34, 3.1E−3, 3.2E−1); cell cycle (1.25, 9.0E−3, 4.8E−1); transcription (1.13, 2.0E−2, 6.7E−1); endoplasmic reticulum (0.97, 1.9E−2, 6.7E−1); gtp-binding (0.91, 5.5E−3, 3.6E−1); nucleotide-binding (0.91, 2.2E−2, 6.8E−1); ubl conjugation pathway (0.76, 7.1E−3, 4.2E−1); membrane (0.32, 3.5E−3, 3.3E−1); | A %<br>T %<br>G %<br>C % | g<br>6.363<br>2.727<br>81.36<br>9.545 | g<br>3.181<br>0.454<br>67.72<br>28.63 | c<br>5.909<br>3.636<br>8.636<br>81.81 |
| 127 | membrane (1.49, 4.0E−4, 2.0E−1); transmembrane (1.49, 5.1E−4, 1.8E−1); nuclear protein (0.83, 8.3E−5, 9.0E−2); | A %<br>T %<br>G %<br>C % | g<br>7.086<br>18.11<br>49.60<br>25.19 | c<br>3.937<br>3.937<br>18.89<br>73.22 | c<br>1.574<br>26.77<br>32.28<br>39.37 |
| 120 | monooxygenase activity (1.71, 2.4E−4, 2.6E−1); monooxygenase (1.71, 8.4E−4, 6.2E−1); | A %<br>T %<br>G %<br>C % | a<br>91.66<br>3.333<br>0.833<br>4.166 | g<br>0<br>2.5<br>97.5<br>0 | c<br>13.33<br>21.66<br>31.66<br>33.33 |
| 119 | embryonic morphogenesis (1.41, 5.3E−5, 1.7E−1); | A %<br>T %<br>G %<br>C % | g<br>0.840<br>5.042<br>79.83<br>14.28 | c<br>1.680<br>0.840<br>1.680<br>95.79 | g<br>21.84<br>1.680<br>75.63<br>0.840 |
| 118 | glycoprotein (1.29, 6.3E−4, 5.2E−1); membrane (1.29, 7.1E−4, 3.3E−1); | A %<br>T %<br>G %<br>C % | g<br>23.72<br>26.27<br>44.91<br>5.084 | g<br>31.35<br>20.33<br>47.45<br>0.847 | c<br>6.779<br>16.10<br>24.57<br>52.54 |
| 118 | Vomeronasal receptor, type 2 (2.64, 1.7E−7, 8.9E−4); metabotropic glutamate receptor signaling pathway (2.64, 3.3E−7, 1.2E−3); glutamate signaling pathway (2.64, 6.3E−7, | A %<br>T % | g<br>5.932<br>28.81 | c<br>4.237<br>20.33 | t<br>15.25<br>63.55 |

TABLE 3-continued

Emerging gene clusters which were identified by the clustering algorithm pertaining *Mus Musculus*.
The below clusters are arranged according to declining size. For each cluster, the table depicts
the distribution of nucleotides for each position along the context sequence.

| | | | | | |
|---|---|---|---|---|---|
| | 1.1E−3); metabotropic glutamate, GABA-B-like receptor activity (2.64, 2.9E−6, 6.9E−3); Extracellular ligand-binding receptor (2.64, 4.6E−6, 1.2E−2); glutamate receptor activity (2.64, 1.4E−5, 1.6E−2); GPCR, family 3, metabotropic glutamate receptor-like (2.64, 5.6E−5, 9.1E−2); cytoskeletal protein binding (1.66, 7.8E−4, 4.7E−1); | | G %<br>C % | 33.89<br>31.35 | 25.42<br>50 | 7.627<br>13.55 |
| 113 | glycosidase (2.36, 1.0E−3, 4.5E−1); developmental protein (0.91, 2.1E−3, 3.9E−1); membrane (0.89, 1.5E−3, 3.5E−1); | A %<br>T %<br>G %<br>C % | g<br>3.539<br>0.884<br>95.57<br>0 | c<br>10.61<br>0.884<br>7.964<br>80.53 | c<br>4.424<br>16.81<br>17.69<br>61.06 |
| 111 | natural killer cell lectin-like receptor binding (2.6, 1.6E−6, 3.8E−3); anchored to plasma membrane (2.6, 1.0E−5, 6.4E−3); anchored to membrane (2.6, 1.0E−5, 6.4E−3); lipoprotein (2.6, 2.5E−4, 2.5E−1); NATURAL KILLER CELL MEDIATED CYTOTOXICITY (2.6, 1.0E−3, 1.8E−1); membrane (0.65, 1.5E−3, 5.8E−1); | A %<br>T %<br>G %<br>C % | g<br>1.801<br>7.207<br>71.17<br>19.81 | a<br>93.69<br>0<br>0<br>6.306 | a<br>100<br>0<br>0<br>0 |
| 108 | signal (0.95, 3.5E−3, 6.4E−1); dna-binding (0.68, 9.7E−4, 6.7E−1); nuclear protein (0.68, 1.7E−3, 6.3E−1); | A %<br>T %<br>G %<br>C % | c<br>6.481<br>12.96<br>29.62<br>50.92 | c<br>11.11<br>5.555<br>2.777<br>80.55 | t<br>1.851<br>94.44<br>0.925<br>2.777 |
| 95 | transmembrane (1.46, 7.0E−5, 7.7E−2); membrane (1.46, 1.9E−4, 1.0E−1); glycoprotein (1.46, 2.9E−3, 5.6E−1); developmental protein (1.2, 1.5E−3, 4.3E−1); developmental protein (0.99, 1.5E−3, 4.3E−1); glycoprotein (0.62, 2.9E−3, 5.6E−1); | A %<br>T %<br>G %<br>C % | g<br>5.263<br>5.263<br>87.36<br>2.105 | c<br>24.21<br>5.263<br>4.210<br>66.31 | g<br>8.421<br>22.10<br>36.84<br>32.63 |
| 94 | cellular physiological process (2.39, 2.6E−6, 9.3E−3); | A %<br>T %<br>G %<br>C % | c<br>3.191<br>3.191<br>3.191<br>90.42 | t<br>3.191<br>87.23<br>2.127<br>7.446 | g<br>1.063<br>6.382<br>89.36<br>3.191 |
| 86 | Carboxylesterase, type B (1.63, 7.1E−5, 3.1E−1); serine esterase (1.63, 1.0E−4, 1.1E−1); | A %<br>T %<br>G %<br>C % | c<br>1.162<br>3.488<br>0<br>95.34 | c<br>23.25<br>5.813<br>0<br>70.93 | t<br>4.651<br>58.13<br>0<br>37.20 |
| 83 | Keratin, high sulfur B2 protein (2.49, 1.6E−5, 7.9E−2); keratin filament (2.49, 3.4E−5, 2.1E−2); | A %<br>T %<br>G %<br>C % | t<br>9.638<br>87.95<br>0<br>2.409 | c<br>1.204<br>4.819<br>0<br>93.97 | t<br>7.228<br>86.74<br>4.819<br>1.204 |
| 80 | glycoprotein (1.16, 1.1E−4, 1.2E−1); signal (1.16, 8.4E−4, 3.8E−1); | A %<br>T %<br>G %<br>C % | c<br>1.25<br>1.25<br>12.5<br>85 | g<br>3.75<br>6.25<br>86.25<br>3.75 | c<br>10<br>0<br>12.5<br>77.5 |
| 79 | zymogen (1.33, 4.6E−4, 4.1E−1); | A %<br>T %<br>G %<br>C % | c<br>36.70<br>16.45<br>5.063<br>41.77 | a<br>96.20<br>1.265<br>2.531<br>0 | g<br>21.51<br>10.12<br>51.89<br>16.45 |
| 79 | extracellular region (1.18, 6.1E−4, 3.1E−1); extracellular space (1.18, 1.3E−3, 3.2E−1); | A %<br>T %<br>G %<br>C % | g<br>1.265<br>26.58<br>69.62<br>2.531 | g<br>5.063<br>1.265<br>93.67<br>0 | a<br>94.93<br>3.797<br>1.265<br>0 |
| 70 | transmembrane (0.82, 1.6E−3, 6.0E−1); | A %<br>T %<br>G %<br>C % | g<br>10<br>18.57<br>42.85<br>28.57 | c<br>10<br>0<br>2.857<br>87.14 | c<br>5.714<br>15.71<br>2.857<br>75.71 |
| 68 | membrane (1.58, 1.1E−4, 1.1E−1); glycoprotein (1.5, 1.1E−3, 4.8E−1); signal (1.5, 1.2E−3, 3.6E−1); | A %<br>T %<br>G %<br>C % | a<br>85.29<br>7.352<br>1.470<br>5.882 | a<br>54.41<br>0<br>29.41<br>16.17 | a<br>91.17<br>2.941<br>4.411<br>1.470 |
| 67 | FBOX (1.74, 2.8E−9, 1.6E−6); Cyclin-like F-box (1.74, 1.5E−7, 7.7E−4); ubl conjugation pathway (1.74, 2.2E−3, 5.7E−1); glycoprotein (1.52, 6.6E−4, 5.3E−1); signal (1.52, 1.9E−3, 6.6E−1); glycoprotein (0.95, 6.6E−4, 5.3E−1); | A %<br>T %<br>G %<br>C % | c<br>25.37<br>13.43<br>26.86<br>34.32 | c<br>2.985<br>7.462<br>0<br>89.55 | a<br>94.02<br>2.985<br>2.985<br>0 |
| 64 | hydrolase (1.95, 1.6E−4, 1.6E−1); | A %<br>T % | c<br>20.31<br>1.562 | a<br>73.43<br>14.06 | g<br>6.25<br>3.125 |

TABLE 3-continued

Emerging gene clusters which were identified by the clustering algorithm pertaining Mus Musculus.
The below clusters are arranged according to declining size. For each cluster, the table depicts
the distribution of nucleotides for each position along the context sequence.

| | | | | | |
|---|---|---|---|---|---|
| | | G % | 9.375 | 9.375 | 48.43 |
| | | C % | 68.75 | 3.125 | 42.18 |
| 62 | SCY (1.28, 1.9E−3, 6.8E−1); transferase (0.95, 1.7E−4, 1.7E−1); | | a | c | c |
| | | A % | 69.35 | 25.80 | 4.838 |
| | | T % | 3.225 | 20.96 | 3.225 |
| | | G % | 11.29 | 1.612 | 24.19 |
| | | C % | 16.12 | 51.61 | 67.74 |
| 61 | transport (1.77, 4.7E−4, 2.4E−1); membrane (0.98, 1.8E−4, 1.9E−1); | | c | g | g |
| | | A % | 18.03 | 31.14 | 11.47 |
| | | T % | 8.196 | 0 | 16.39 |
| | | G % | 6.557 | 49.18 | 70.49 |
| | | C % | 67.21 | 19.67 | 1.639 |
| 61 | Hormone (4.77, 4.2E−13, 4.8E−10); Somatotropin hormone (4.77, 7.6E−12, 3.9E−8); Cytokine, four-helical bundle (4.77, 1.7E−10, 4.3E−7); hormone activity (4.77, 2.4E−8, 5.8E−5); receptor binding (4.77, 1.2E−5, 9.5E−3); Glycoprotein (4.77, 1.2E−5, 7.0E−3); Signal (4.77, 3.9E−5, 1.5E−2); extracellular space (4.77, 5.2E−4, 2.7E−1); extracellular region (4.77, 1.8E−3, 4.2E−1); | | ag | c | c |
| | | A % | 34.42 | 3.278 | 0 |
| | | T % | 22.95 | 1.639 | 6.557 |
| | | G % | 34.42 | 4.918 | 0 |
| | | C % | 8.196 | 90.16 | 93.44 |
| 55 | nucleotide-binding (1.94, 1.2E−4, 1.3E−1); adenyl nucleotide binding (1.94, 1.6E−4, 3.1E−1); protein amino acid phosphorylation (1.94, 1.6E−4, 4.4E−1); purine nucleotide binding (1.94, 2.3E−4, 2.5E−1); phosphorylation (1.94, 4.0E−4, 5.2E−1); atp-binding (1.94, 5.4E−4, 2.6E−1); ATP binding (1.94, 5.5E−4, 2.8E−1); nucleotide binding (1.94, 7.6E−4, 3.1E−1); phosphorus metabolism (1.94, 1.2E−3, 6.5E−1); phosphate metabolism (1.94, 1.2E−3, 6.5E−1); kinase activity (1.94, 1.3E−3, 4.2E−1); transferase activity, transferring phosphorus-containing groups (1.94, 3.1E−3, 6.1E−1); kinase (1.94, 3.6E−3, 6.5E−1); receptor binding (1.84, 4.3E−4, 2.9E−1); transmembrane protein (0.53, 2.0E−3, 5.2E−1); | | c | t | c |
| | | A % | 3.636 | 1.818 | 9.090 |
| | | T % | 25.45 | 87.27 | 16.36 |
| | | G % | 16.36 | 10.90 | 0 |
| | | C % | 54.54 | 0 | 74.54 |
| 52 | E-class P450, CYP3A (2.21, 4.0E−7, 2.1E−3); METABOLISM OF XENOBIOTICS BY CYTOCHROME P450 (2.21, 2.1E−5, 4.1E−3); GAMMA-HEXACHLOROCYCLOHEXANE DEGRADATION (2.21, 2.2E−5, 2.2E−3); LINOLEIC ACID METABOLISM (2.21, 1.9E−4, 1.2E−2); | | g | a | a |
| | | A % | 11.53 | 78.84 | 59.61 |
| | | T % | 1.923 | 3.846 | 5.769 |
| | | G % | 51.92 | 5.769 | 30.76 |
| | | C % | 34.61 | 11.53 | 3.846 |
| 50 | KRAB box (1.94, 1.3E−6, 6.6E−3); nuclear protein (1.94, 3.6E−5, 4.0E−2); ZnF_C2H2 (1.94, 4.4E−5, 2.5E−2); Zinc finger, C2H2-type (1.94, 5.3E−5, 1.3E−1); zinc-finger (1.94, 6.3E−5, 3.5E−2); KRAB (1.94, 8.0E−5, 2.3E−2); zinc (1.94, 3.1E−4, 1.1E−1); metal-binding (1.94, 3.4E−4, 9.4E−2); General function prediction only (1.94, 1.7E−2, 6.9E−1); hyaluronoglucosaminidase activity (1.8, 7.9E−5, 1.7E−1); Glycoside hydrolase, family 56 (1.8, 8.0E−5, 1.3E−1); hexosaminidase activity (1.8, 3.9E−4, 3.8E−1); | | t | t | c |
| | | A % | 30 | 0 | 4 |
| | | T % | 44 | 94 | 4 |
| | | G % | 8 | 6 | 2 |
| | | C % | 18 | 0 | 90 |
| 46 | intracellular membrane-bound organelle (2.38, 4.2E−4, 2.3E−1); membrane-bound organelle (2.38, 4.3E−4, 1.2E−1); intracellular organelle (2.38, 2.3E−3, 3.8E−1); organelle (2.38, 2.4E−3, 3.1E−1); intracellular (2.38, 4.7E−3, 4.4E−1); nucleus (2.38, 6.1E−3, 4.6E−1); dna-binding (0.93, 9.5E−4, 6.6E−1); nucleus (0.93, 6.1E−3, 4.6E−1); | | c | c | t |
| | | A % | 10.86 | 4.347 | 6.521 |
| | | T % | 0 | 4.347 | 84.78 |
| | | G % | 0 | 8.695 | 4.347 |
| | | C % | 89.13 | 82.60 | 4.347 |
| 42 | integrin complex (1.32, 1.6E−3, 6.3E−1); | | a | c | t |
| | | A % | 100 | 7.142 | 4.761 |
| | | T % | 0 | 16.66 | 95.23 |
| | | G % | 0 | 11.90 | 0 |
| | | C % | 0 | 64.28 | 0 |
| 42 | Tryp_SPc (2.24, 3.0E−4, 1.6E−1); serine protease (2.24, 1.0E−3, 6.9E−1); | | g | c | t |
| | | A % | 9.523 | 2.380 | 26.19 |
| | | T % | 23.80 | 9.523 | 73.80 |
| | | G % | 38.09 | 0 | 0 |
| | | C % | 28.57 | 88.09 | 0 |
| 41 | defense response to bacteria (3.53, 5.5E−8, 2.0E−4); Beta defensin (3.53, 7.7E−8, 4.0E−4); response to bacteria (3.53, 1.4E−7, 2.4E−4); defensin (3.53, 3.4E−7, 3.9E−4); antibiotic (3.53, 4.7E−7, 2.7E−4); antimicrobial (3.53, 7.3E−7, 2.8E−4); response to stress (3.53, 5.0E−4, 4.6E−1); | | g | c | t |
| | | A % | 2.439 | 0 | 4.878 |
| | | T % | 31.70 | 4.878 | 92.68 |
| | | G % | 60.97 | 14.63 | 2.439 |
| | | C % | 4.878 | 80.48 | 0 |
| 41 | transmembrane (1.47, 5.4E−4, 4.6E−1); membrane (1.47, 2.2E−3, 5.7E−1); glycoprotein (1.19, 6.8E−4, 3.2E−1); plasma (1.19, 4.0E−3, 6.8E−1); | | g | a | c |
| | | A % | 0 | 60.97 | 2.439 |
| | | T % | 12.19 | 4.878 | 2.439 |
| | | G % | 82.92 | 34.14 | 2.439 |
| | | C % | 4.878 | 0 | 92.68 |
| 40 | UDP-glucuronosyl/UDP-glucosyltransferase (2.59, 3.5E−6, 1.8E−2); SF005678: glucuronosyltransferase (2.59, 3.7E−6, 8.0E−3); | | a | t | t |
| | | A % | 57.5 | 0 | 17.5 |
| | | T % | 12.5 | 67.5 | 82.5 |

TABLE 3-continued

Emerging gene clusters which were identified by the clustering algorithm pertaining *Mus Musculus*. The below clusters are arranged according to declining size. For each cluster, the table depicts the distribution of nucleotides for each position along the context sequence.

| | | | | | | |
|---|---|---|---|---|---|---|
| | | G % | 7.5 | 2.5 | 0 | |
| | | C % | 22.5 | 30 | 0 | |
| 38 | SF005558: natural killer cell receptor P1 (4.28, 2.1E−12, 4.4E−9); lectin (4.28, 1.0E−11, 1.2E−8); C-type lectin (4.28, 1.2E−10, 6.1E−7); CLECT (4.28, 1.3E−10, 7.4E−8); sugar binding (4.28, 2.2E−9, 5.4E−6); t-cell (4.28, 8.0E−9, 4.6E−6); carbohydrate binding (4.28, 3.0E−8, 3.6E−5); domain: C-type lectin (4.28, 3.5E−8, 1.1E−4); antigen (4.28, 8.9E−8, 3.4E−5); signal-anchor (4.28, 5.5E−7, 1.6E−4); cell adhesion (4.28, 1.6E−5, 3.7E−3); receptor (4.28, 2.9E−5, 5.5E−3); glycoprotein (4.28, 4.1E−4, 6.4E−2); multigene family (4.28, 7.1E−4, 9.6E−2); membrane (4.28, 1.5E−3, 1.7E−1); transmembrane (4.28, 6.5E−3, 5.2E−1); | A % T % G % C % | a 86.84 2.631 10.52 0 | c 2.631 0 28.94 68.42 | t 0 97.36 0 2.631 | |

| Size of Cluster (number of context sequences) | Distribution of nucleotides per position along the context sequence (%) | | | | | |
|---|---|---|---|---|---|---|
| | −6 | −5 | −4 | −3 | −2 | −1 |
| 1197 | g 4.594 6.182 81.03 8.187 | c 9.857 8.020 25.48 56.64 | c 36.42 5.680 6.683 51.21 | g 47.11 0.835 50.04 2.005 | c 2.840 3.675 2.088 91.39 | c 1.169 1.587 4.010 93.23 |
| 710 | c 25.91 17.04 15.91 41.12 | g 3.521 22.39 45.77 28.30 | c 7.183 7.887 15.91 69.01 | g 36.61 1.408 58.87 3.098 | c 3.802 3.661 8.450 84.08 | c 0.845 0.422 1.549 97.18 |
| 397 | a 44.33 13.85 37.27 4.534 | g 25.94 9.571 59.94 4.534 | g 8.816 8.060 64.23 18.89 | a 96.22 0 1.763 2.015 | a 89.42 0.251 8.060 2.267 | g 5.541 1.511 89.16 3.778 |
| 357 | g 5.322 5.882 63.30 25.49 | c 3.081 18.76 3.361 74.78 | c 1.960 1.120 3.641 93.27 | a 88.51 1.400 5.882 4.201 | g 40.61 3.081 52.10 4.201 | g 3.361 2.801 70.86 22.96 |
| 373 | c 22.25 22.52 20.64 34.58 | c 6.702 2.412 36.19 54.69 | a 52.54 10.72 24.39 12.33 | g 1.340 0.536 96.51 1.608 | c 6.970 9.115 3.217 80.69 | c 0.536 3.485 2.680 93.29 |
| 290 | g 3.448 0.689 93.44 2.413 | g 26.55 12.06 47.58 13.79 | g 7.241 2.068 80.68 10 | a 75.51 1.034 22.41 1.034 | a 82.75 3.103 11.03 3.103 | g 11.72 1.034 83.79 3.448 |
| 283 | t 18.37 49.82 20.14 11.66 | c 7.067 4.240 10.60 78.09 | c 5.653 2.120 3.886 88.33 | a 96.11 0.353 2.473 1.060 | c 4.240 35.68 13.78 46.28 | c 1.413 1.766 1.766 95.05 |
| 220 | g 7.727 7.272 77.27 7.727 | g 4.090 4.545 90.45 0.909 | c 0.454 0.909 3.181 95.45 | g 21.81 0.909 75.90 1.363 | g 15.45 4.090 49.54 30.90 | g 3.181 1.818 50.90 44.09 |
| 127 | g 2.362 18.11 77.16 2.362 | g 18.11 8.661 65.35 7.874 | g 0.787 6.299 90.55 2.362 | g 2.362 0.787 92.91 3.937 | c 2.362 0 0.787 96.85 | c 0.787 3.149 1.574 94.48 |
| 120 | c 6.666 25 22.5 45.83 | t 15 75 2.5 7.5 | c 9.166 20 20 50.83 | a 45.83 3.333 43.33 7.5 | c 2.5 4.166 8.333 85 | c 6.666 3.333 4.166 85.83 |
| 119 | g 0.840 0.840 92.43 5.882 | c 27.73 1.680 5.042 65.54 | g 2.521 4.201 56.30 36.97 | g 3.361 0 88.23 8.403 | c 15.12 4.201 11.76 68.90 | c 5.882 5.042 35.29 53.78 |

TABLE 3-continued

Emerging gene clusters which were identified by the clustering algorithm pertaining *Mus Musculus*.
The below clusters are arranged according to declining size. For each cluster, the table depicts
the distribution of nucleotides for each position along the context sequence.

| | | | | | | |
|---|---|---|---|---|---|---|
| 118 | a | g | c | a | g | g |
| | 44.91 | 11.86 | 4.237 | 90.67 | 0.847 | 11.86 |
| | 33.89 | 22.03 | 0 | 3.389 | 0 | 7.627 |
| | 0.847 | 55.93 | 0.847 | 0.847 | 95.76 | 78.81 |
| | 20.33 | 10.16 | 94.91 | 5.084 | 3.389 | 1.694 |
| 118 | g | c | a | g | a | c |
| | 0.847 | 8.474 | 85.59 | 1.694 | 83.89 | 22.88 |
| | 0.847 | 5.932 | 11.01 | 0 | 5.084 | 0.847 |
| | 90.67 | 0 | 0.847 | 96.61 | 4.237 | 10.16 |
| | 7.627 | 85.59 | 2.542 | 1.694 | 6.779 | 66.10 |
| 113 | g | g | c | a | g | c |
| | 25.66 | 7.079 | 0 | 84.95 | 0 | 2.654 |
| | 9.734 | 7.079 | 1.769 | 5.309 | 29.20 | 8.849 |
| | 45.13 | 58.40 | 1.769 | 0.884 | 70.79 | 1.769 |
| | 19.46 | 27.43 | 96.46 | 8.849 | 0 | 86.72 |
| 111 | g | a | c | a | g | c |
| | 11.71 | 36.03 | 7.207 | 99.09 | 23.42 | 19.81 |
| | 3.603 | 6.306 | 2.702 | 0 | 9.009 | 3.603 |
| | 79.27 | 29.72 | 6.306 | 0.900 | 38.73 | 34.23 |
| | 5.405 | 27.92 | 83.78 | 0 | 28.82 | 42.34 |
| 108 | g | g | c | a | g | c |
| | 1.851 | 19.44 | 37.03 | 95.37 | 20.37 | 4.629 |
| | 1.851 | 14.81 | 4.629 | 2.777 | 29.62 | 3.703 |
| | 96.29 | 62.03 | 6.481 | 0.925 | 42.59 | 25 |
| | 0 | 3.703 | 51.85 | 0.925 | 7.407 | 66.66 |
| 95 | c | t | g | g | c | c |
| | 1.052 | 1.052 | 9.473 | 0 | 4.210 | 2.105 |
| | 3.157 | 48.42 | 3.157 | 0 | 4.210 | 4.210 |
| | 2.105 | 24.21 | 87.36 | 100 | 8.421 | 23.15 |
| | 93.68 | 26.31 | 0 | 0 | 83.15 | 70.52 |
| 94 | c | a | g | g | c | c |
| | 4.255 | 39.36 | 7.446 | 43.61 | 6.382 | 0 |
| | 15.95 | 38.29 | 7.446 | 2.127 | 4.255 | 1.063 |
| | 37.23 | 19.14 | 85.10 | 50 | 13.82 | 0 |
| | 42.55 | 3.191 | 0 | 4.255 | 75.53 | 98.93 |
| 86 | c | c | c | a | c | c |
| | 5.813 | 10.46 | 24.41 | 91.86 | 27.90 | 2.325 |
| | 30.23 | 33.72 | 4.651 | 2.325 | 1.162 | 1.162 |
| | 1.162 | 2.325 | 1.162 | 5.813 | 10.46 | 4.651 |
| | 62.79 | 53.48 | 69.76 | 0 | 60.46 | 91.86 |
| 83 | g | gc | c | g | c | c |
| | 1.204 | 21.68 | 18.07 | 24.09 | 1.204 | 0 |
| | 1.204 | 18.07 | 16.86 | 1.204 | 4.819 | 3.614 |
| | 92.77 | 30.12 | 10.84 | 67.46 | 3.614 | 8.433 |
| | 4.819 | 30.12 | 54.21 | 7.228 | 90.36 | 87.95 |
| 80 | c | c | c | g | c | g |
| | 1.25 | 3.75 | 6.25 | 2.5 | 8.75 | 0 |
| | 1.25 | 2.5 | 17.5 | 2.5 | 0 | 7.5 |
| | 36.25 | 8.75 | 15 | 92.5 | 7.5 | 92.5 |
| | 61.25 | 85 | 61.25 | 2.5 | 83.75 | 0 |
| 79 | g | t | c | a | c | c |
| | 2.531 | 7.594 | 11.39 | 81.01 | 1.265 | 1.265 |
| | 10.12 | 82.27 | 1.265 | 1.265 | 2.531 | 1.265 |
| | 67.08 | 6.329 | 36.70 | 5.063 | 0 | 0 |
| | 20.25 | 3.797 | 50.63 | 12.65 | 96.20 | 97.46 |
| 79 | g | t | c | a | c | c |
| | 13.92 | 3.797 | 1.265 | 73.41 | 5.063 | 2.531 |
| | 3.797 | 58.22 | 3.797 | 1.265 | 3.797 | 1.265 |
| | 70.88 | 37.97 | 22.78 | 18.98 | 12.65 | 0 |
| | 11.39 | 0 | 72.15 | 6.329 | 78.48 | 96.20 |
| 70 | a | g | a | ag | ag | c |
| | 85.71 | 4.285 | 72.85 | 45.71 | 31.42 | 7.142 |
| | 4.285 | 0 | 2.857 | 0 | 21.42 | 1.428 |
| | 2.857 | 78.57 | 15.71 | 45.71 | 31.42 | 8.571 |
| | 7.142 | 17.14 | 8.571 | 8.571 | 15.71 | 82.85 |
| 68 | g | g | g | a | g | g |
| | 48.52 | 1.470 | 44.11 | 97.05 | 32.35 | 26.47 |
| | 1.470 | 0 | 0 | 1.470 | 1.470 | 4.411 |
| | 50 | 94.11 | 51.47 | 1.470 | 66.17 | 54.41 |
| | 0 | 4.411 | 4.411 | 0 | 0 | 14.70 |
| 67 | c | t | c | a | a | g |
| | 2.985 | 16.41 | 4.477 | 98.50 | 62.68 | 5.970 |
| | 7.462 | 53.73 | 1.492 | 0 | 2.985 | 1.492 |
| | 8.955 | 1.492 | 37.31 | 0 | 31.34 | 92.53 |
| | 80.59 | 28.35 | 56.71 | 1.492 | 2.985 | 0 |

TABLE 3-continued

Emerging gene clusters which were identified by the clustering algorithm pertaining *Mus Musculus*.
The below clusters are arranged according to declining size. For each cluster, the table depicts
the distribution of nucleotides for each position along the context sequence.

| | | | | | | |
|---|---|---|---|---|---|---|
| 64 | c | t | c | a | g | c |
| | 7.812 | 0 | 1.562 | 95.31 | 7.812 | 4.687 |
| | 28.12 | 71.87 | 0 | 0 | 7.812 | 1.562 |
| | 7.812 | 20.31 | 0 | 0 | 81.25 | 1.562 |
| | 56.25 | 7.812 | 98.43 | 4.687 | 3.125 | 92.18 |
| 62 | a | g | c | a | t | c |
| | 95.16 | 12.90 | 9.677 | 74.19 | 9.677 | 0 |
| | 1.612 | 27.41 | 11.29 | 1.612 | 87.09 | 0 |
| | 3.225 | 35.48 | 12.90 | 22.58 | 1.612 | 0 |
| | 0 | 24.19 | 66.12 | 1.612 | 1.612 | 100 |
| 61 | g | c | g | g | c | c |
| | 8.196 | 1.639 | 3.278 | 1.639 | 1.639 | 0 |
| | 4.918 | 3.278 | 27.86 | 1.639 | 1.639 | 0 |
| | 78.68 | 0 | 54.09 | 68.85 | 0 | 11.47 |
| | 8.196 | 95.08 | 14.75 | 27.86 | 96.72 | 88.52 |
| 61 | g | c | a | g | a | g |
| | 21.31 | 3.278 | 91.80 | 11.47 | 63.93 | 6.557 |
| | 27.86 | 0 | 0 | 1.639 | 3.278 | 11.47 |
| | 34.42 | 4.918 | 3.278 | 85.24 | 6.557 | 81.96 |
| | 16.39 | 91.80 | 4.918 | 1.639 | 26.22 | 0 |
| 55 | g | g | g | a | c | c |
| | 0 | 1.818 | 12.72 | 94.54 | 21.81 | 3.636 |
| | 3.636 | 1.818 | 5.454 | 0 | 3.636 | 0 |
| | 94.54 | 94.54 | 41.81 | 5.454 | 1.818 | 5.454 |
| | 1.818 | 1.818 | 40 | 0 | 72.72 | 90.90 |
| 52 | g | c | a | g | a | g |
| | 1.923 | 1.923 | 84.61 | 0 | 76.92 | 5.769 |
| | 1.923 | 3.846 | 1.923 | 0 | 9.615 | 3.846 |
| | 57.69 | 3.846 | 3.846 | 98.07 | 11.53 | 86.53 |
| | 38.46 | 90.38 | 9.615 | 1.923 | 1.923 | 3.846 |
| 50 | t | c | t | g | ag | c |
| | 6 | 4 | 0 | 16 | 36 | 2 |
| | 68 | 2 | 98 | 0 | 12 | 6 |
| | 6 | 8 | 0 | 84 | 36 | 6 |
| | 20 | 86 | 2 | 0 | 16 | 86 |
| 46 | g | c | a | g | c | t |
| | 0 | 10.86 | 97.82 | 0 | 6.521 | 10.86 |
| | 2.173 | 21.73 | 0 | 0 | 10.86 | 54.34 |
| | 97.82 | 17.39 | 2.173 | 89.13 | 8.695 | 30.43 |
| | 0 | 50 | 0 | 10.86 | 73.91 | 4.347 |
| 42 | g | c | c | a | c | c |
| | 19.04 | 38.09 | 19.04 | 95.23 | 35.71 | 2.380 |
| | 0 | 2.380 | 26.19 | 2.380 | 4.761 | 2.380 |
| | 78.57 | 14.28 | 9.523 | 2.380 | 11.90 | 0 |
| | 2.380 | 45.23 | 45.23 | 0 | 47.61 | 95.23 |
| 42 | g | c | c | a | c | a |
| | 2.380 | 4.761 | 2.380 | 100 | 38.09 | 88.09 |
| | 0 | 21.42 | 2.380 | 0 | 2.380 | 7.142 |
| | 97.61 | 2.380 | 2.380 | 0 | 0 | 4.761 |
| | 0 | 71.42 | 92.85 | 0 | 59.52 | 0 |
| 41 | t | c | a | g | t | c |
| | 0 | 0 | 46.34 | 17.07 | 14.63 | 0 |
| | 90.24 | 0 | 41.46 | 0 | 58.53 | 0 |
| | 2.439 | 2.439 | 4.878 | 80.48 | 0 | 0 |
| | 7.317 | 97.56 | 7.317 | 2.439 | 26.82 | 100 |
| 41 | c | c | c | a | c | c |
| | 0 | 12.19 | 2.439 | 78.04 | 4.878 | 2.439 |
| | 0 | 19.51 | 2.439 | 2.439 | 0 | 14.63 |
| | 2.439 | 24.39 | 0 | 19.51 | 0 | 7.317 |
| | 97.56 | 43.90 | 95.12 | 0 | 95.12 | 75.60 |
| 40 | t | t | c | a | a | g |
| | 5 | 0 | 5 | 100 | 50 | 0 |
| | 65 | 95 | 0 | 0 | 2.5 | 5 |
| | 0 | 2.5 | 10 | 0 | 47.5 | 87.5 |
| | 30 | 2.5 | 85 | 0 | 0 | 7.5 |
| 38 | c | c | c | a | a | a |
| | 0 | 0 | 2.631 | 94.73 | 57.89 | 55.26 |
| | 2.631 | 23.68 | 0 | 0 | 10.52 | 0 |
| | 5.263 | 0 | 10.52 | 5.263 | 10.52 | 39.47 |
| | 92.10 | 76.31 | 86.84 | 0 | 21.05 | 5.263 |

TABLE 4

Emerging gene clusters which were identified by the clustering method pertaining Bos Tauros.
The below clusters are arranged according to declining size. For each cluster, the table depicts
the distribution of nucleotides for each position along the context sequence.

| Size of Cluster (number of genes) | Function attributes set (Enrichment score/P_value/Benjamini) | Pos: | −9 | −8 | −7 |
|---|---|---|---|---|---|
| 815 | structural molecule activity (2.4, 6.1E−5, 7.0E−2); structural constituent of ribosome (2.4, 8.6E−5, 5.0E−2); ribosome (2.4, 3.4E−4, 8.5E−2); ribosomal protein (2.4, 4.9E−4, 2.0E−1); ribonucleoprotein complex (2.4, 1.1E−3, 1.4E−1); membrane (1.3, 4.8E−3, 3.9E−1); regulation of signal transduction (1.03, 4.0E−3, 6.9E−1); regulation of signal transduction (0.87, 4.0E−3, 6.9E−1); intracellular non-membrane-bound organelle (0.79, 2.9E−3, 2.3E−1); non-membrane-bound organelle (0.79, 2.9E−3, 2.3E−1); lipoprotein (0.4, 6.9E−3, 4.4E−1); | A % T % G % C % | g 11.77 9.079 63.55 15.58 | c 7.975 8.343 22.45 61.22 | c 10.30 14.72 20.73 54.23 |
| 583 | intracellular non-membrane-bound organelle (1.78, 5.5E−3, 5.2E−1); non-membrane-bound organelle (1.78, 5.5E−3, 5.2E−1); ribosome (1.78, 8.9E−3, 5.5E−1); pyridoxal phosphate (1.23, 6.3E−3, 4.8E−1); homodimer (1.11, 1.6E−3, 2.5E−1); membrane (1.07, 8.7E−4, 2.3E−1); glycoprotein (1.07, 1.3E−2, 6.2E−1); eye lens protein (1.03, 6.1E−3, 5.1E−1); kinase (0.69, 1.1E−2, 6.0E−1); cytoplasm (0.65, 1.5E−2, 6.4E−1); transit peptide (0.4, 7.5E−3, 5.0E−1); | A % T % G % C % | g 10.29 10.46 49.91 29.33 | c 7.375 18.86 20.75 53.00 | c 8.404 15.95 27.95 47.68 |
| 474 | Cathelicidin (2.77, 9.5E−6, 2.7E−2); antibiotic (2.77, 2.3E−4, 1.0E−1); antimicrobial (2.77, 5.7E−4, 1.0E−1); pyrrolidone carboxylic acid (2.77, 2.0E−3, 2.7E−1); fungicide (2.77, 8.2E−3, 6.6E−1); nucleotide-binding (1.68, 1.5E−4, 1.3E−1); signal (0.96, 4.2E−4, 1.2E−1); | A % T % G % C % | 24.26 15.18 18.14 42.40 | c 3.797 18.35 36.28 41.56 | c 13.08 13.50 21.51 51.89 |
| 463 | cellular macromolecule metabolism (2.17, 6.4E−4, 6.1E−1); cellular physiological process (2.17, 7.0E−4, 4.0E−1); cellular protein metabolism (2.17, 1.1E−3, 4.0E−1); protein metabolism (2.17, 1.6E−3, 4.5E−1); structural molecule activity (1.74, 1.7E−4, 1.9E−1); intracellular non-membrane-bound organelle (1.74, 1.9E−3, 4.0E−1); non-membrane-bound organelle (1.74, 1.9E−3, 4.0E−1); cellular physiological process (1.47, 7.0E−4, 4.0E−1); structural molecule activity (1.32, 1.7E−4, 1.9E−1); intracellular non-membrane-bound organelle (1.32, 1.9E−3, 4.0E−1); non-membrane-bound organelle (1.32, 1.9E−3, 4.0E−1); homodimer (1.14, 2.2E−3, 6.4E−1); protein polymerization (0.92, 2.0E−3, 4.5E−1); cytoskeleton (0.92, 1.1E−2, 6.2E−1); | A % T % G % C % | g 8.639 4.319 68.25 18.79 | c 3.239 3.455 20.73 72.57 | c 9.503 10.79 19.43 60.25 |
| 300 | transit peptide (2, 8.4E−6, 7.7E−3); transit peptide: Mitochondrion (2, 4.2E−4, 4.2E−1); mitochondrion (2, 1.8E−3, 4.3E−1); ubiquinone (2, 3.2E−3, 5.2E−1); oxidoreductase (2, 3.3E−3, 4.5E−1); intracellular membrane-bound organelle (1.75, 1.8E−3, 3.8E−1); membrane-bound organelle (1.75, 1.9E−3, 2.2E−1); cytoplasm (1.75, 3.5E−3, 2.7E−1); intracellular organelle (1.75, 6.8E−3, 3.6E−1); organelle (1.75, 7.2E−3, 3.2E−1); membrane (0.8, 7.3E−3, 6.8E−1); | A % T % G % C % | g 17.66 12 51.66 18.66 | g 14.33 4 70.33 11.33 | a 53 5 21.66 20.33 |
| 289 | glycoprotein (2.82, 3.1E−4, 2.5E−1); signal (2.82, 4.9E−4, 2.0E−1); disulfide bond (2.82, 5.7E−4, 5.2E−1); Propeptide, peptidase A1 (2.62, 1.6E−4, 3.8E−1); Peptidase aspartic, active site (2.62, 4.5E−4, 4.8E−1); pepsin A activity (2.62, 7.7E−4, 6.0E−1); aspartic-type endopeptidase activity (2.62, 1.0E−3, 4.6E−1); duplication (1.45, 1.7E−3, 3.2E−1); cytokine (0.5, 7.9E−4, 2.2E−1); | A % T % G % C % | g 28.37 13.14 44.29 14.18 | a 52.24 14.87 12.11 20.76 | a 47.75 13.14 21.45 17.64 |
| 223 | signal (1.73, 5.3E−4, 3.9E−1); structural constituent of ribosome (1.21, 4.7E−4, 4.3E−1); ribosome (1.21, 1.3E−3, 2.8E−1); ribonucleoprotein complex (1.21, 1.7E−3, 2.0E−1); ribosomal protein (1.21, 1.9E−3, 5.9E−1); | A % T % G % C % | g 16.59 6.726 56.50 20.17 | c 5.381 7.623 23.76 63.22 | c 12.55 11.65 4.035 71.74 |
| 215 | cellular physiological process (1.64, 2.2E−3, 6.6E−1); cellular process (1.64, 2.4E−3, 5.9E−1); cellular protein metabolism (1.64, 3.2E−3, 6.1E−1); coated vesicle membrane (1.43, 7.3E−3, 3.8E−1); vesicle coat (1.43, 7.3E−3, 3.8E−1); membrane coat (1.43, 7.3E−3, 3.8E−1); coated membrane (1.43, 7.3E−3, 3.8E−1); vesicle membrane (1.43, 8.8E−3, 3.2E−1); cytoplasmic vesicle membrane (1.43, 8.8E−3, 3.2E−1); coated vesicle (1.43, 1.2E−2, 3.7E−1); cytoplasmic membrane-bound vesicle (1.43, 2.2E−2, 5.1E−1); vesicle (1.43, 2.2E−2, 5.1E−1); membrane-bound vesicle (1.43, 2.2E−2, 5.1E−1); | A % T % G % C % | g 2.325 0.930 90.69 6.046 | c 1.395 2.325 2.790 93.48 | c 5.116 6.511 24.65 63.72 |

TABLE 4-continued

Emerging gene clusters which were identified by the clustering method pertaining Bos Tauros.
The below clusters are arranged according to declining size. For each cluster, the table depicts
the distribution of nucleotides for each position along the context sequence.

| | | | | | |
|---|---|---|---|---|---|
| | cytoplasmic vesicle (1.43, 2.2E−2, 5.1E−1); cytoskeleton (1.35, 3.6E−2, 5.0E−1); microtubule cytoskeleton (1.35, 4.9E−2, 5.8E−1); cellular physiological process (0.95, 2.2E−3, 6.6E−1); cellular process (0.95, 2.4E−3, 5.9E−1); intracellular non-membrane-bound organelle (0.83, 3.4E−2, 5.3E−1); non-membrane-bound organelle (0.83, 3.4E−2, 5.3E−1): | | | | |
| 213 | signal (2.88, 2.8E−7, 2.6E−4); glycoprotein (2.88, 2.1E−5, 9.6E−3); membrane (2.88, 1.1E−4, 3.3E−2); transmembrane (2.88, 2.2E−3, 3.9E−1); | | c | a | g |
| | | A % | 18.30 | 39.43 | 18.77 |
| | | T % | 11.73 | 15.49 | 6.103 |
| | | G % | 19.24 | 28.63 | 70.42 |
| | | C % | 50.70 | 16.43 | 4.694 |
| 84 | nucleotide-binding (1.14, 2.2E−4, 1.8E−1); atp-binding (1.14, 1.2E−3, 4.2E−1); | | a | c | c |
| | | A % | 66.66 | 2.380 | 5.952 |
| | | T % | 10.71 | 3.571 | 1.190 |
| | | G % | 3.571 | 44.04 | 19.04 |
| | | C % | 19.04 | 50 | 73.80 |
| 66 | membrane-bound organelle (1.11, 7.9E−3, 6.5E−1); | | g | g | a |
| | | A % | 21.21 | 13.63 | 68.18 |
| | | T % | 15.15 | 3.030 | 9.090 |
| | | G % | 33.33 | 43.93 | 22.72 |
| | | C % | 30.30 | 39.39 | 0 |
| 52 | nad (1.73, 1.2E−3, 6.7E−1); | | g | t | c |
| | | A % | 3.846 | 25 | 21.15 |
| | | T % | 7.692 | 40.38 | 7.692 |
| | | G % | 67.30 | 28.84 | 34.61 |
| | | C % | 21.15 | 5.769 | 36.53 |
| 33 | ribonucleoprotein complex (1.11, 1.2E−2, 6.7E−1); | | g | c | c |
| | | A % | 15.15 | 6.060 | 21.21 |
| | | T % | 0 | 0 | 15.15 |
| | | G % | 78.78 | 0 | 0 |
| | | C % | 6.060 | 93.93 | 63.63 |
| 32 | Cathelicidin (3.99, 8.6E−10, 2.5E−6); antibiotic (3.99, 2.6E−7, 2.4E−4); antimicrobial (3.99, 4.6E−7, 2.1E−4); pyrrolidone carboxylic acid (3.99, 1.1E−6, 3.4E−4); | | c | g | g |
| | | A % | 0 | 3.125 | 0 |
| | | T % | 0 | 31.25 | 6.25 |
| | | G % | 0 | 40.62 | 56.25 |
| | | C % | 100 | 25 | 37.5 |
| 30 | Lipid-binding serum glycoprotein (0.94, 2.5E−4, 5.2E−1); | | c | a | g |
| | | A % | 20 | 40 | 0 |
| | | T % | 3.333 | 30 | 0 |
| | | G % | 0 | 23.33 | 96.66 |
| | | C % | 76.66 | 6.666 | 3.333 |
| 29 | Cathelicidin (5.17, 1.6E−11, 4.6E−8); pyrrolidone carboxylic acid (5.17, 3.5E−9, 3.2E−6); antibiotic (5.17, 3.8E−8, 1.8E−5); antimicrobial (5.17, 7.9E−8, 2.4E−5); SF001637: cathelin (5.17, 2.3E−4, 2.1E−1); signal (5.17, 4.9E−4, 1.1E−1); | | c | t | c |
| | | A % | 6.896 | 0 | 0 |
| | | T % | 20.68 | 96.55 | 13.79 |
| | | G % | 3.448 | 3.448 | 41.37 |
| | | C % | 68.96 | 0 | 44.82 |

| Size of Cluster (number of genes) | Distribution of nucleotides per position along the context sequence (%) | | | | | |
|---|---|---|---|---|---|---|
| | −6 | −5 | −4 | −3 | −2 | −1 |
| 815 | g | c | c | a | c | c |
| | 7.361 | 9.202 | 15.70 | 66.01 | 24.66 | 3.190 |
| | 15.21 | 14.72 | 2.453 | 1.349 | 7.361 | 2.576 |
| | 51.77 | 32.51 | 21.10 | 30.06 | 32.63 | 46.38 |
| | 25.64 | 43.55 | 60.73 | 2.576 | 35.33 | 47.85 |
| 583 | g | c | c | g | c | c |
| | 9.777 | 4.459 | 27.78 | 26.07 | 3.945 | 1.715 |
| | 13.37 | 10.46 | 3.602 | 0.686 | 6.861 | 3.602 |
| | 65.00 | 21.09 | 10.97 | 70.32 | 1.886 | 8.747 |
| | 11.83 | 63.97 | 57.63 | 2.915 | 87.30 | 85.93 |
| 474 | gc | g | c | a | c | c |
| | 23.62 | 10.54 | 8.016 | 55.27 | 3.797 | 3.375 |
| | 11.81 | 15.82 | 8.438 | 3.797 | 2.531 | 4.008 |
| | 32.27 | 40.08 | 18.35 | 36.70 | 6.962 | 4.008 |
| | 32.27 | 33.54 | 65.18 | 4.219 | 86.70 | 88.60 |
| 463 | g | c | c | g | c | c |
| | 7.343 | 2.807 | 39.95 | 20.51 | 4.967 | 0.431 |
| | 3.239 | 3.671 | 1.943 | 0.863 | 5.615 | 1.295 |
| | 76.88 | 36.28 | 5.399 | 77.53 | 6.479 | 3.455 |
| | 12.52 | 57.23 | 52.69 | 1.079 | 82.93 | 94.81 |
| 300 | g | g | c | a | a | g |
| | 14.33 | 21 | 24 | 87 | 69.66 | 11.33 |

TABLE 4-continued

Emerging gene clusters which were identified by the clustering method pertaining Bos Tauros. The below clusters are arranged according to declining size. For each cluster, the table depicts the distribution of nucleotides for each position along the context sequence.

|  |  |  |  |  |  |  |
|---|---|---|---|---|---|---|
|  | 6.666 | 6.666 | 2 | 0.333 | 4 | 2 |
|  | 63.66 | 40 | 32.33 | 11.33 | 19.33 | 63.33 |
|  | 15.33 | 32.33 | 41.66 | 1.333 | 7 | 23.33 |
| 289 | a | g | a | a | a | c |
|  | 48.09 | 15.91 | 42.90 | 93.77 | 40.13 | 31.48 |
|  | 22.49 | 24.91 | 5.882 | 0.692 | 7.266 | 5.882 |
|  | 22.83 | 40.48 | 9.342 | 4.152 | 28.71 | 22.14 |
|  | 6.574 | 18.68 | 41.86 | 1.384 | 23.87 | 40.48 |
| 223 | g | c | c | a | g | g |
|  | 3.587 | 1.345 | 1.345 | 95.96 | 28.69 | 4.484 |
|  | 14.34 | 4.932 | 1.345 | 0.448 | 7.174 | 1.793 |
|  | 56.05 | 33.63 | 4.484 | 2.242 | 62.33 | 57.39 |
|  | 26.00 | 60.08 | 92.82 | 1.345 | 1.793 | 36.32 |
| 215 | g | c | c | g | c | c |
|  | 3.720 | 3.255 | 17.67 | 28.83 | 1.395 | 0.465 |
|  | 1.395 | 4.186 | 0 | 0 | 1.860 | 0.930 |
|  | 90.69 | 35.81 | 5.116 | 70.69 | 2.325 | 5.116 |
|  | 4.186 | 56.74 | 77.20 | 0.465 | 94.41 | 93.48 |
| 213 | g | a | c | a | g | c |
|  | 40.84 | 41.31 | 8.450 | 94.36 | 23.94 | 10.79 |
|  | 6.572 | 29.57 | 0.469 | 0.469 | 27.69 | 2.816 |
|  | 43.19 | 25.82 | 35.21 | 0.469 | 32.39 | 32.86 |
|  | 9.389 | 3.286 | 55.86 | 4.694 | 15.96 | 53.52 |
| 84 | a | g | c | a | c | c |
|  | 78.57 | 3.571 | 1.190 | 92.85 | 4.761 | 8.333 |
|  | 14.28 | 1.190 | 0 | 0 | 5.952 | 3.571 |
|  | 4.761 | 84.52 | 3.571 | 3.571 | 19.04 | 2.380 |
|  | 2.380 | 10.71 | 95.23 | 3.571 | 70.23 | 85.71 |
| 66 | g | g | g | a | a | g |
|  | 6.060 | 0 | 9.090 | 95.45 | 93.93 | 3.030 |
|  | 0 | 7.575 | 0 | 0 | 0 | 1.515 |
|  | 86.36 | 89.39 | 46.96 | 4.545 | 1.515 | 90.90 |
|  | 7.575 | 3.030 | 43.93 | 0 | 4.545 | 4.545 |
| 52 | c | c | a | g | c | c |
|  | 1.923 | 5.769 | 38.46 | 0 | 19.23 | 5.769 |
|  | 5.769 | 0 | 23.07 | 0 | 0 | 0 |
|  | 0 | 0 | 28.84 | 92.30 | 11.53 | 0 |
|  | 92.30 | 94.23 | 9.615 | 7.692 | 69.23 | 94.23 |
| 33 | g | c | c | a | g | c |
|  | 0 | 0 | 0 | 93.93 | 6.060 | 12.12 |
|  | 0 | 3.030 | 0 | 0 | 39.39 | 6.060 |
|  | 100 | 0 | 0 | 0 | 54.54 | 0 |
|  | 0 | 96.96 | 100 | 6.060 | 0 | 81.81 |
| 32 | g | g | g | g | c | c |
|  | 3.125 | 6.25 | 15.62 | 40.62 | 6.25 | 0 |
|  | 0 | 0 | 3.125 | 0 | 0 | 3.125 |
|  | 96.87 | 93.75 | 81.25 | 59.37 | 0 | 3.125 |
|  | 0 | 0 | 0 | 0 | 93.75 | 93.75 |
| 30 | g | a | gc | a | a | g |
|  | 30 | 86.66 | 0 | 100 | 96.66 | 0 |
|  | 3.333 | 10 | 0 | 0 | 0 | 0 |
|  | 66.66 | 0 | 50 | 0 | 3.333 | 100 |
|  | 0 | 3.333 | 50 | 0 | 0 | 0 |
| 29 | g | g | c | a | c | c |
|  | 6.896 | 3.448 | 24.13 | 96.55 | 3.448 | 3.448 |
|  | 0 | 0 | 0 | 0 | 0 | 0 |
|  | 93.10 | 93.10 | 24.13 | 0 | 3.448 | 0 |
|  | 0 | 3.448 | 51.72 | 3.448 | 93.10 | 96.55 |

REFERENCES

[1] Everitt. B., Cluster Analysis, Edward Arnold, London, 1993
[1] W. Thong, G. Altun, R. Harrison, P. C. Tai, and Y. Pan, Improved K-Means Clustering Algorithm for Exploring Local Protein Sequence Motifs, Representing. Common Structural Property, IEEE TRANSACTIONS ON NANO-BIOSCIENCE, VOL. 4, NO. 3, SEPTEMBER 2005.
[1] K. F. Han, D. Baker, Recurring local sequence motifs in proteins J. Mol. Biol., vol. 251(1), pages 176-187, 1995
[1] Heidecker G, Messing J: Structural analysis of plant genes. Annu. Rev. Plant Physiol. 37, 439-466 (1986)
[1] C. P. Joshi, An Inspection of the domain putative An inspection of the domain between putative TATA box and translation start site in 79 plant genes, Nucleic Acids Research, 1987, Vol. 15, No. 16 6643-6653.
[1] C. P. Joshi, H. Thou, X. Huang and V. L. Chiang, Context sequences of translation initiation codon in plants, Plant Molecular Biology 35: 993-1001, 1997; Q. Liu, Q. Xue, Comparative studies on sequence characteristics around translation initiation codon in four eukaryotes, Journal of Genetics, Vol. 84, No. 3, December 2005.
[1] M. Jaiswal, L. Rangan, Context Sequence For Transcription Factors Surrounding Start Codon in Model Crops, CURRENT SCIENCE, VOL. 93, NO. 2, 25 Jul. 2007.

[1] Kozak M. Nucleotide sequences of 5'-terminal ribosome-protected initiation regions from two reovirus messages. Nature. 1977 Sep. 29; 269(5627):391-4; Kozak M. Possible role of flanking nucleotides in recognition of the AUG initiator codon by eukaryotic ribosomes. Nucleic Acids Res. 1981 Oct. 24; 9(20):5233-52.; Kozak M. Sequences of ribosome binding sites from the large size class of reovirus mRNA. J. Virol. 1982 May; 42(2):467-73

[1] Compilation and analysis of sequences upstream from the translational start site in eukaryotic mRNAs. Nucleic Acids Res. 1984 Jan. 25; 12(2):857-72.; Kozak M: An analysis of 50-noncoding sequences from 699 vertebrate messenger RNAs. Nucl Acids Res 15, 8125-8148 (1987); Kozak M: At least six nucleotides preceding the AUG initiator codon enhance translation in mammalian cells. J Mol Biol 196: 947-950 (1987).

[1] Samir V. S., Pradhyumna K. S., Shiv K. G., Raju M. and Rakesh T, Conserved nucleotide sequences in highly expressed genes in plants, Journal of Genetics, Vol. 78, No. 2, August 1999 123.

[1] Taylor J L, Jones J D G, Sandler S, Mueller G M, Bedbrook J, Dunsmuir, Optimizing the Expression of Chimeric Genes in Plant Cells, Mol. Gen. Genet. (1987)210, pages 572-577.

[1] Sleat D. E., Gallie D. R, Jefferson R. A., Bevan M. W., Turner P. C., Wilson T. M. A., Characterization of the 50-leader Sequence of Tobacco Mosaic Virus RNA as a General Enhancer of Translation in vitro, Gene (1987) 217: 217-225.

[1] Chandrashekhar P. Joshi, Hao Zhou, Xiaoqiu Huang and Vincent L. Chiang, Context sequences of translation initiation codon in plants, Plant Molecular Biology 35: 993-1001, 1997, at p. 998 below.

[1] C. P. Joshi, H. Zhou, X. Huang and V. L. Chiang, Context sequences of translation initiation codon in plants, Plant Molecular Biology (1997)35: 993-1001, see Table 3 at p. 1000.

[1] See for example U.S. Pat. No. 7,253,342.

[1] D. Arthur, S. Vassilvitskii, How Slow is the k—Means Method?, 2006 (Stanford, yet unpublished). See www-.stanford.edu/~sergeiv/papers/ldVIeans-socg.pdf

[1] Thomas H. Cormen, Charles E. Leiserson, Ronald L. Rivest (1990): Introduction to algorithms. MIT Press/ McGraw-Hill.

[1] Dennis G Jr, Sherman B T, Hosack D A, Yang J, Gao W, Lane H C, Lempicki R A. DAVID: Database for Annotation, Visualization, and Integrated Discovery. Genome Biology 2003, 4(5).

[1] D. A Hosack, G. D. Jr, B. T Sherman, H C. Lane, R. A Lempicki. Identifying Biological Themes within Lists of Genes with EASE. Genome Biology 2003 4(6).

[1] Dennis G Jr, Sherman B T, Hosack D A, Yang J, Gao W, Lane H C, Lempicki R A. DAVID: Database for Annotation, Visualization, and Integrated Discovery. Genome Biology 2003, 4(5).

[1] D. A Hosack, G. D. Jr, B. T Sherman, H C. Lane, R. A Lempicki. Identifying Biological Themes within Lists of Genes with EASE. Genome Biology 2003 4(6).

[1] Chandrashekhar P. Joshi, Hao Zhou, Xiaoqiu Huang and Vincent L. Chiang, Context sequences of translation initiation codon in plants, Plant Molecular Biology 35: 993-1001, 1997.

[1] Chandrashekhar P. Joshi, Hao Thou, Xiaoqiu Huang and Vincent L. Chiang, Context sequences of translation initiation codon in plants, Plant Molecular Biology 35: 993-1001, 1997, at p. 999.

The invention claimed is:

1. A computer implemented method for identifying a sequence template as statistically associated with plant functional annotations of interest, the method implemented on a computer comprising a processor, and computer readable memory comprising RAM and secondary storage, the method comprising:
 (a) obtaining, using the processor, a first plant functional annotation set comprising at least one plant functional annotation from a user;
 (b) obtaining, using the processor, a data repository comprising polynucleotide plant mRNA sequences and storing the data repository in the computer readable memory; and
 (c) for each mRNA sequence, identifying, using the processor, the translation initiation codon and a corresponding context sequence comprising a stretch of nucleotides preceding the translation initiation codon;
 (d) transforming, using the processor, each of the context sequences into a sequence template;
 (e) allocating, in the computer readable memory, a multiple-tree-array data structure, the multiple-tree-array consisting of a root node and a plurality of heaps, at least one of the heaps being stored in the RAM and at least one of the heaps being stored in the secondary storage;
 (f) inserting, using the processor, data items into the multiple-tree-array, the data items comprising two sequence templates and a distance between the sequence templates;
 (g) clustering, using the processor, the sequence templates, wherein the clustering comprises retrieving data items from the multiple-tree-array, storing data items in the multiple-tree-array, and merging the sequence templates in a cluster into a common sequence template that represents all of the templates within the cluster;
 (h) selecting, using the processor, a cluster;
 (i) obtaining, using the processor, a list of plant functional annotations that are statistically overrepresented within said cluster; and
 (j) storing the sequence template and the functional annotations of said cluster in the computer readable memory.

2. The computer implemented method of claim 1, wherein the corresponding context sequence is a stretch of 9 or 10 nucleotides preceding the translation initiation codon.

3. The computer implemented method of claim 1, said attributes are selected from: the Gene Ontology Project (GO), Interpro annotation (European Molecular Biology Laboratory, EMBL), SMART (a Simple Modular Architecture Research Tool), UniProt Knowledgebase (SwissProt), OMIM (by NCBI) PROSITE (by the Swiss Institute of Bioinformatics), Protein Information Resource (PIR), GeneCards, and Kyoto Encyclopedia of Genes and Genomes (KEGG).

4. The computer implemented method of claim 1, wherein step (c) further includes the step of aligning the context sequences of the polynucleotide plant mRNA sequences.

5. The computer implemented method of claim 1, wherein the sequence template is a distribution matrix representing the distribution of each nucleotide for each nucleotide position which characterizes the corresponding context sequence.

6. The computer implemented method of claim 5, wherein the distribution matrix is paired to the first plant functional annotation set comprising at least one plant functional annotation.

7. The computer implemented method of claim 6, further comprising allocating a tabular memory structure comprising table rows, wherein the table rows comprise data including the distribution matrix representing the sequence template and the associated plant functional annotations and wherein a user interface provides for a user to enter a desired importance degree or confidence level associated with a particular function attribute.

8. The computer implemented method of claim 7, wherein the data repository is RefSeq.

9. The computer implemented method of claim 1, wherein the data repository comprising polynucleotide plant mRNA sequences is curated.

10. The computer implemented method of claim 1, wherein the retrieval of data items from the multiple-tree-array and storage of data items in the multiple-tree-array are managed through a common interface such that at least one of the heaps maintained in the RAM can be replaced with at least one heap maintained in the secondary storage.

\* \* \* \* \*